(12) United States Patent
Coe et al.

(10) Patent No.: US 7,442,694 B2
(45) Date of Patent: Oct. 28, 2008

(54) DIAZABICYCLIC COMPOUNDS USEFUL IN THE TREATMENT OF CNS AND OTHER DISORDERS

(75) Inventors: Jotham W. Coe, Niantic, CT (US); Christopher J. O'Donnell, Mystic, CT (US); Brian T. O'Neill, Old Saybrook, CT (US); Lawrence A. Vincent, Moosup, CT (US)

(73) Assignee: Pfizer Inc, New York, NY (US)

( * ) Notice: Subject to any disclaimer, the term of this patent is extended or adjusted under 35 U.S.C. 154(b) by 280 days.

(21) Appl. No.: 10/657,738

(22) Filed: Sep. 8, 2003

(65) Prior Publication Data

US 2004/0106603 A1 Jun. 3, 2004

Related U.S. Application Data

(60) Provisional application No. 60/409,694, filed on Sep. 10, 2002.

(51) Int. Cl.
*C07D 487/08* (2006.01)
*A61K 31/495* (2006.01)

(52) U.S. Cl. .................. 514/219; 514/221; 540/556

(58) Field of Classification Search ............ 540/556; 514/219, 221
See application file for complete search history.

(56) References Cited

U.S. PATENT DOCUMENTS

| 4,571,396 A | 2/1986 | Mich et al. |
| 4,775,668 A | 10/1988 | Martin |
| 6,407,095 B1 | 6/2002 | Jeunesse et al. |

FOREIGN PATENT DOCUMENTS

| EP | 0284935 | 10/1988 |
| EP | 0391132 | 10/1990 |
| EP | 0563734 | 10/1993 |
| WO | WO 8802627 | 4/1988 |
| WO | WO 9942465 | 8/1999 |
| WO | WO 0006575 | 2/2000 |
| WO | WO 0155150 | 8/2001 |

OTHER PUBLICATIONS

Damaj et al., Medline Abstract (Psychopharmacologia, vol. 120, Issue 4, pp. 483-490) Aug. 1995.*
Layzer, Degenerative Diseases of the Nervous System, Cecil Textbook of Medicine, 20th Edition, vol. 2, pp. 2050-2057, 1996.*
Damasio, Alzheimer's Disease and related dementias, Cecil Textbook of Medicine, 20th Edition, vol. 2, pp. 1992-1996, 1996.*
Marcus et al., PubMed Abstract (Intervirology, 45(4-6):260-6) 2002.*
Van Heeswijk, PubMed Abstract (Ther Drug Monit. 24(3):323-31), Jun. 2002.*
Court et al., PubMed Abstract (J Chem Neuroanat. 20(3-4):281-98), Dec. 2000.*
Terry et al., PubMed Abstract (Neuroscience, 101(2):357-68), 2000.*
Mirza et al., PubMed Abstract (Psychopharmacology (Berl). 148(3):243-50), Feb. 2000.*
Sonis, The Pathology of Mucositis, Nat Rev Cancer 44(4):277-284, 2004.*

* cited by examiner

*Primary Examiner*—Deepak Rao
(74) *Attorney, Agent, or Firm*—Steven T. Zelson; Garth Butterfield; Mary J. Hosley

(57) ABSTRACT

The present invention relates to a compounds of formula I:

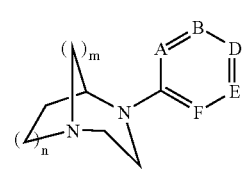

wherein A, B, D, E and F are defined herein; that are useful in treating central nervous system (CNS) diseases, disorders and conditions, such as but not limited to nicotine addiction, schizophrenia, depression, Alzheimer's disease, Parkinson's disease and ADHD. The present invention further comprises pharmaceutical compositions containing such compounds and methods of treatment comprising the use of such compounds.

12 Claims, No Drawings

DIAZABICYCLIC COMPOUNDS USEFUL IN THE TREATMENT OF CNS AND OTHER DISORDERS

This application claims the benefit of U.S. Ser. No. 60/409,694, filed Sep. 10, 2002, the contents of which are incorporated herein by reference.

BACKGROUND OF THE INVENTION

The present invention relates to diazabicyclic compounds useful in treating central nervous system (CNS) diseases, disorders and conditions, such as, but not limited to, nicotine addiction, schizophrenia, depression, Alzheimer's disease, Parkinson's disease and ADHD. The present invention further comprises pharmaceutical compositions containing such compounds and methods of treatment comprising the use of such compounds. The compounds of the invention bind to neuronal nicotinic acetylcholine specific receptor sites and are useful in modulating cholinergic function.

By the use of a CNS-penetrant nicotinic receptor modulating compounds of the present invention, it is possible to treat a number of central nervous system diseases, disorders and conditions, including addictions, in patients for whom conventional therapy is not wholly successful or where dependence upon the therapeutic drug is prevalent.

Copending applications U.S. Ser. No. 10/068,692 and U.S. Ser. No. 10/047,850 are drawn to 1,4-diazabicyclo[3.2.2]nonane-4-carboxyl or 4-thiocarboxyl compounds; and benzoxazole- and azabenzoxazole-diazabicyclic derivative compounds; respectively, and both are useful in the treatment of CNS disorders.

Other published references recite diazabicycloalkane compounds as having activity towards nicotinic receptors. Such compounds recited in the field are 1,4-diazabicyclo[3.2.2]nonane derivatives (WO 00/34279); 2,5-diazabicyclo[2.2.1]heptane derivatives (WO 00/34284); 1,4-diaza-bicyclo[3.2.2]nonane-4-carboxylate and carboxamide derivatives (WO 00/58311); 1,4-diazabicyclo[3.2.2]nonane-phenylisoxazoles (WO 01/92259);4-(2-phenylthiazol-5-yl)-1,4-diazabicyclo[3.2.2]nonanes (WO 01/92260); 1,4-diazabicyclo[3.2.2]nonabenzoxazole, -benzthiazole and benzimidazole derivatives (WO 01/92261); and 4-heteroaryl-1,4-diazabicyclo[3.2.2]nonane compounds (WO 01/55150). In addition, another reference, WO 00/45846, recites compositions containing nicotine or a nicotinic receptor ligand and an inhibitor of a monoamine oxidase for use in smoking cessation treatment.

SUMMARY OF THE INVENTION

The present invention relates to compounds of the formula I

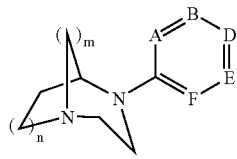

wherein:
A=$CR^1$ or N,
B=$CR^2$ or N,
D=$CR^3$ or N,
E=$CR^4$ or N and
F=$CR^5$ or N;

and the maximum number of nitrogen atoms amongst A, B, D, E, and F is two;

where m=1-3 and n=1-3 and excluding all compounds where m=n=2;

where each $R^1$, $R^2$, $R^3$, $R^4$ and $R^5$ is independently selected from F, Cl, Br, I, nitro, cyano, $CF_3$, —$NR^6R^7$, —$NR^6C(=O)R^7$, —$NR^6C(=O)NR^7R^8$, —$NR^6C(=O)OR^7$, —$NR^6S(=O)_2R^7$, —$NR^6S(=O)_2NR^7R^8$, —$OR^6$, —$OC(=O)R^6$, —$OC(=O)OR^6$, —$OC(=O)NR^6R^7$, —$OC(=O)SR^6$, —$C(=O)OR^6$, —$C(=O)R^6$, —$C(=O)NR^6R^7$, —$SR^6$, —$S(=O)R^6$, —$S(=O)_2R^6$, —$S(=O)_2NR^6R^7$, and a substituent from the definition of $R^6$;

each $R^6$, $R^7$, and $R^8$ is independently selected from H, straight chain or branched ($C_1$-$C_8$)alkyl, straight chain or branched ($C_2$-$C_8$)alkenyl, straight chain or branched ($C_2$-$C_8$)alkynyl, ($C_3$-$C_8$)cycloalkyl, ($C_4$-$C_8$)cycloalkenyl, 3-8 membered heterocycloalkyl, ($C_5$-$C_{11}$)bicycloalkyl, ($C_7$-$C_{11}$)bicycloalkenyl, 5-11 membered heterobicycloalkyl, 5-11 membered heterobicycloalkenyl, ($C_6$-$C_{11}$)aryl, and 5-12 membered heteroaryl; wherein each $R^6$, $R^7$, and $R^8$ is optionally substituted with from one to six substituents, independently selected from F, Cl, Br, I, nitro, cyano, $CF_3$, —$NR^9R^{10}$, —$NR^9C(=O)R^{10}$, —$NR^9C(=O)NR^{10}OR^{11}$, —$NR^9C(=O)OR^{10}$, —$NR^9S(=O)_2R^{10}$, —$NR^9S(=O)_2NR^{10}R^{11}$, —$OR^9$, —$OC(=O)R^9$, —$OC(=O)OR^9$, —$OC(=O)NR^9R^{10}$, —$OC(=O)SR^9$, —$C(=O)OR^9$, —$C(=O)R^9$, —$C(=O)NR^9R^{10}$, —$SR^9$, —$S(=O)R^9$, —$S(=O)_2R^9$, —$S(=O)_2NR^9R^{10}$ and $R^9$;

or $R^1$ and $R^2$, or $R^2$ and $R^3$, or $R^3$ and $R^4$, or $R^4$ and $R^5$, may form another 6-membered aromatic or heteroaromatic ring sharing A and B, or B and D, or D and E, or E and F, respectively, and may be optionally substituted with from one to four substituents independently selected from the group of radicals set forth in the definition of $R^6$, $R^7$ and $R^8$ above;

each $R^9$, $R^{10}$ and $R^{11}$ is independently selected from H, straight chain or branched ($C_1$-$C_8$)alkyl, straight chain or branched ($C_2$-$C_8$)alkenyl, straight chain or branched ($C_2$-$C_8$)alkynyl, ($C_3$-$C_8$)cycloalkyl, ($C_4$-$C_8$)cycloalkenyl, 3-8 membered heterocycloalkyl, ($C_5$-$C_{11}$)bicycloalkyl, ($C_7$-$C_{11}$)bicycloalkenyl, 5-11 membered heterobicycloalkyl, (5-11 membered) heterobicycloalkenyl, ($C_6$-$C_{11}$)aryl or 5-12 membered heteroaryl; wherein each $R^9$, $R^{10}$ and $R^{11}$ is optionally substituted with from one to six substituents independently selected from F, Cl, Br, I, nitro, cyano, $CF_3$, —$NR^{12}R^{13}$, —$NR^{12}C(=O)R^{13}$, —$NR^{12}C(=O)NR^{13}R^{14}$, —$NR^{12}C(=O)OR^{13}$, —$NR^{12}S(=O)_2R^{13}$, —$NR^{12}S(=O)_2NR^{13}R^{14}$, —$OR^{12}$, —$OC(=O)R^{12}$, —$OC(=O)OR^{12}$, —$OC(=O)NR^{12}R^{13}$, —$OC(=O)SR^{12}$, —$C(=O)OR^{12}$, —$C(=O)R^{12}$, —$C(=O)NR^{12}R^{13}$, —$SR^{12}$, —$S(=O)R^{12}$, —$S(=O)_2R^{12}$, —$S(=O)_2NR^{12}R^{13}$ and $R^{12}$;

each $R^{12}$, $R^{13}$, and $R^{14}$ is independently selected from H, straight chain or branched ($C_1$-$C_8$)alkyl, straight chain or branched ($C_2$-$C_8$)alkenyl, straight chain or branched ($C_2$-$C_8$)alkynyl, ($C_3$-$C_8$)cycloalkyl, ($C_4$-$C_8$)cycloalkenyl, 3-8 membered heterocycloalkyl, ($C_5$-$C_{11}$)bicycloalkyl, ($C_7$-$C_{11}$)bicycloalkenyl, 5-11 membered heterobicycloalkyl, 5-11 membered heterobicycloalkenyl, ($C_6$-$C_{11}$)aryl and (5-12 membered) heteroaryl;

and all enantiomeric, diastereomeric, and tautomeric isomers and pharmaceutically acceptable salts thereof.

Preferred compounds of the invention are those compounds of formula I wherein one or two of A, B, D or E is N.

Further, preferred compounds of the invention are those compounds of formula I wherein A and B are both N.

Further, preferred compounds of the invention are those compounds of formula I wherein A and E are both N.

Further, preferred compounds of the invention are those compounds of formula I wherein B and E are both N.

Further, preferred compounds of the invention are those compounds of formula I wherein one of A, B or E is N.

Further, preferred compounds of the invention are those compounds of formula I wherein one of A or B is N.

Preferred compounds of the invention are those compounds of formula I wherein each $R^1$, $R^2$, $R^3$, $R^4$ and $R^5$ is independently selected from H, halo, $(C_1-C_6)$alkyl, $(C_1-C_6)$alkoxy, $(C_1-C_6)$fluoroalkyl, cyano, $(C_1-C_6)$alkoxycarbonyl; phenyl substituted or unsubstituted with halo, $(C_1-C_6)$alkyl, $(C_1-C_6)$alkoxy, $(C_1-C_6)$fluoroalkyl; and heteroaryl. Further preferred is where any one of the $R^1$ and $R^2$, or $R^2$ and $R^3$, or $R^3$ and $R^4$, or $R^4$ and $R^5$ pairs located on adjacent carbon atoms join to form an unsaturated $(C_4)$alkylene bridge.

Preferred compounds of the invention are those compounds of formula I wherein m=1 and n=1.

Preferred compounds of the invention are those compounds of formula I wherein m=1 and n=2.

Preferred compounds of the invention are those compounds of formula I wherein m=1 and n=3.

Preferred compounds of the invention are those compounds of formula I wherein m=2 and n=3.

Preferred compounds of the invention are those compounds of formula I wherein m=3 and n=3.

Examples of specific compounds of this invention are the following compounds of the formula I and their pharmaceutically acceptable salts, hydrates, solvates and optical and other stereoisomers. Particular preferred compounds of the invention are those where n=2 and m=1 and are selected from the group consisting of:

4-(5-Bromo-pyridin-3-yl)-1,4-diaza-bicyclo[3.2.1]octane;
4-(5-Phenyl-pyridin-3-yl)-1,4-diaza-bicyclo[3.2.1]octane;
4-Pyridin-2-yl-1,4-diaza-bicyclo[3.2.1]octane;
4-Pyridin-3-yl-1,4-diaza-bicyclo[3.2.1]octane;
4-Pyridin-4-yl-1,4-diaza-bicyclo[3.2.1]octane;
4-(5-Phenyl-pyridazin-3-yl)-1,4-diaza-bicyclo[3.2.1]octane;
4-(5-Bromo-pyridin-2-yl)-1,4-diaza-bicyclo[3.2.1]octane;
4-(6-Phenyl-pyridazin-3-yl)-1,4-diaza-bicyclo[3.2.1]octane;
4-Pyrazin-2-yl-1,4-diaza-bicyclo[3.2.1]octane;
4-Pyrimidin-5-yl-1,4-diaza-bicyclo[3.2.1]octane;
4-(5-Chloro-pyridin-3-yl)-1,4-diaza-bicyclo[3.2.1]octane;
4-[5-(3-Trifluoromethyl-phenyl)-pyridin-3-yl]-1,4-diaza-bicyclo[3.2.1]octane;
4-(3-Bromo-phenyl)-1,4-diaza-bicyclo[3.2.1]octane;
5-(1,4-Diaza-bicyclo[3.2.1]oct-4-yl)-nicotinonitrile;
4-(5-Trifluoromethyl-pyridin-3-yl)-1,4-diaza-bicyclo[3.2.1]octane;
4-[5-(2-Trifluoromethyl-phenyl)-pyridin-3-yl]-1,4-diaza-bicyclo[3.2.1]octane;
4-[5-(4-Trifluoromethyl-phenyl)-pyridin-3-yl]-1,4-diaza-bicyclo[3.2.1]octane;
4-[5-(2-Fluoro-phenyl)-pyridin-3-yl]-1,4-diaza-bicyclo[3.2.1]octane;
4-[5-(4-Fluoro-phenyl)-pyridin-3-yl]-1,4-diaza-bicyclo[3.2.1]octane;
3-(1,4-Diaza-bicyclo[3.2.1]oct-4-yl)-quinoline;
4-(3-Trifluoromethyl-pyridin-2-yl)-1,4-diaza-bicyclo[3.2.1]octane;
4-(6-Methoxy-pyridin-2-yl)-1,4-diaza-bicyclo[3.2.1]octane;
4-[5-(2-Methoxy-phenyl)-pyridin-3-yl]-1,4-diaza-bicyclo[3.2.1]octane;
4-[5-(3-Methoxy-phenyl)-pyridin-3-yl]-1,4-diaza-bicyclo[3.2.1]octane;
4-(5-o-Tolyl-pyridin-3-yl)-1,4-diaza-bicyclo[3.2.1]octane;
5-(1,4-Diaza-bicyclo[3.2.1]oct-4-yl)-nicotinic acid ethyl ester;
4-(5-Chloro-pyridin-2-yl)-1,4-diaza-bicyclo[3.2.1]octane;
4-(6-Methyl-pyridin-3-yl)-1,4-diaza-bicyclo[3.2.1]octane;
4-[5-(3-Trifluoromethyl-phenyl)-pyridin-2-yl]-1,4-diaza-bicyclo[3.2.1]octane;
4-[5-(4-Chloro-phenyl)-pyridin-2-yl]-1,4-diaza-bicyclo[3.2.1]octane;
4-(5-o-Tolyl-pyridin-2-yl)-1,4-diaza-bicyclo[3.2.1]octane;
4-[5-(3-Chloro-phenyl)-pyridin-2-yl]-1,4-diaza-bicyclo[3.2.1]octane;
4-[5-(3-Fluoro-phenyl)-pyridin-2-yl]-1,4-diaza-bicyclo[3.2.1]octane;
4-[5-(4-Chloro-phenyl)-pyridin-3-yl]-1,4-diaza-bicyclo[3.2.1]octane;
4-[5-(2,4-Dichloro-phenyl)-pyridin-3-yl]-1,4-diaza-bicyclo[3.2.1]octane;
4-[5-(3-Chloro-phenyl)-pyridin-3-yl]-1,4-diaza-bicyclo[3.2.1]octane;
4-(5-p-Tolyl-pyridin-3-yl)-1,4-diaza-bicyclo[3.2.1]octane;
4-[5-(4-Methoxy-phenyl)-pyridin-3-yl]-1,4-diaza-bicyclo[3.2.1]octane;
4-(5-Methoxy-pyridin-3-yl)-1,4-diaza-bicyclo[3.2.1]octane;
5-(1,4-Diaza-bicyclo[3.2.1]oct-4-yl)-[3,4']bipyridinyl; and
4-(2-Methyl-5-trifluoromethyl-pyridin-3-yl)-1,4-diaza-bicyclo[3.2.1]octane.

Further preferred compounds of the invention are:
(+)-4-(5-Bromo-pyridin-3-yl)-1,4-diaza-bicyclo[3.2.1]octane;
(+)-4-(5-Phenyl-pyridin-3-yl)-1,4-diaza-bicyclo[3.2.1]octane;
(+)-4-Pyridin-2-yl-1,4-diaza-bicyclo[3.2.1]octane;
(+)-4-Pyridin-3-yl-1,4-diaza-bicyclo[3.2.1]octane;
(+)-4-Pyridin-4-yl-1,4-diaza-bicyclo[3.2.1]octane;
(+)-4-(5-Phenyl-pyridazin-3-yl)-1,4-diaza-bicyclo[3.2.1]octane;
(+)-4-(5-Bromo-pyridin-2-yl)-1,4-diaza-bicyclo[3.2.1]octane;
(+)-4-(6-Phenyl-pyridazin-3-yl)-1,4-diaza-bicyclo[3.2.1]octane;
(+)-4-Pyrazin-2-yl-1,4-diaza-bicyclo[3.2.1]octane;
(+)-4-Pyrimidin-5-yl-1,4-diaza-bicyclo[3.2.1]octane;
(+)-4-(5-Chloro-pyridin-3-yl)-1,4-diaza-bicyclo[3.2.1]octane;
(+)-4-[5-(3-Trifluoromethyl-phenyl)-pyridin-3-yl]-1,4-diaza-bicyclo[3.2.1]octane;
(+)-4-(3-Bromo-phenyl)-1,4-diaza-bicyclo[3.2.1]octane;
(+)-5-(1,4-Diaza-bicyclo[3.2.1]oct-4-yl)-nicotinonitrile;
(+)-4-(5-Trifluoromethyl-pyridin-3-yl)-1,4-diaza-bicyclo[3.2.1]octane;
(+)-4-[5-(2-Trifluoromethyl-phenyl)-pyridin-3-yl]-1,4-diaza-bicyclo[3.2.1]octane;
(+)-4-[5-(4-Trifluoromethyl-phenyl)-pyridin-3-yl]-1,4-diaza-bicyclo[3.2.1]octane;
(+)-4-[5-(2-Fluoro-phenyl)-pyridin-3-yl]-1,4-diaza-bicyclo[3.2.1]octane;
(+)-4-[5-(4-Fluoro-phenyl)-pyridin-3-yl]-1,4-diaza-bicyclo[3.2.1]octane;
(+)-3-(1,4-Diaza-bicyclo[3.2.1]oct-4-yl)-quinoline;
(+)-4-(3-Trifluoromethyl-pyridin-2-yl)-1,4-diaza-bicyclo[3.2.1]octane;
(+)-4-(3-Methoxy-pyridin-2-yl)-1,4-diaza-bicyclo[3.2.1]octane;

(+)-4-[5-(2-Methoxy-phenyl)-pyridin-3-yl]-1,4-diaza-bicyclo[3.2.1]octane;
(+)-4-[5-(3-Methoxy-phenyl)-pyridin-3-yl]-1,4-diaza-bicyclo[3.2.1]octane;
(+)-4-(5-o-Tolyl-pyridin-3-yl)-1,4-diaza-bicyclo[3.2.1]octane;
(+)-5-(1,4-Diaza-bicyclo[3.2.1]oct-4-yl)-nicotinic acid ethyl ester;
(+)-4-(5-Chloro-pyridin-2-yl)-1,4-diaza-bicyclo[3.2.1]octane;
(+)-4-(6-Methyl-pyridin-3-yl)-1,4-diaza-bicyclo[3.2.1]octane;
(+)-4-[5-(3-Trifluoromethyl-phenyl)-pyridin-2-yl]-1,4-diaza-bicyclo[3.2.1]octane;
(+)-4-[5-(4-Chloro-phenyl)-pyridin-2-yl]-1,4-diaza-bicyclo[3.2.1]octane;
(+)-4-(5-o-Tolyl-pyridin-2-yl)-1,4-diaza-bicyclo[3.2.1]octane;
(+)-4-[5-(3-Chloro-phenyl)-pyridin-2-yl]-1,4-diaza-bicyclo[3.2.1]octane;
(+)-4-[5-(3-Fluoro-phenyl)-pyridin-2-yl]-1,4-diaza-bicyclo[3.2.1]octane;
(+)-4-[5-(4-Chloro-phenyl)-pyridin-3-yl]-1,4-diaza-bicyclo[3.2.1]octane;
(+)-4-[5-(2,4-Dichloro-phenyl)-pyridin-3-yl]-1,4-diaza-bicyclo[3.2.1]octane;
(+)-4-[5-(3-Chloro-phenyl)-pyridin-3-yl]-1,4-diaza-bicyclo[3.2.1]octane;
(+)-4-(5-p-Tolyl-pyridin-3-yl)-1,4-diaza-bicyclo[3.2.1]octane;
(+)-4-[5-(4-Methoxy-phenyl)-pyridin-3-yl]-1,4-diaza-bicyclo[3.2.1]octane;
(+)-4-(5-Methoxy-pyridin-3-yl)-1,4-diaza-bicyclo[3.2.1]octane;
(+)-5-(1,4-Diaza-bicyclo[3.2.1]oct-4-yl)-[3,4']bipyridinyl; and
(+)-4-(2-Methyl-5-trifluoromethyl-pyridin-3-yl)-1,4-diaza-bicyclo[3.2.1]octane.

Further preferred compounds of the invention are:
(−)-4-(5-Bromo-pyridin-3-yl)-1,4-diaza-bicyclo[3.2.1]octane;
(−)-4-(5-Phenyl-pyridin-3-yl)-1,4-diaza-bicyclo[3.2.1]octane;
(−)-4-Pyridin-2-yl-1,4-diaza-bicyclo[3.2.1]octane;
(−)-4-Pyridin-3-yl-1,4-diaza-bicyclo[3.2.1]octane;
(−)-4-Pyridin-4-yl-1,4-diaza-bicyclo[3.2.1]octane;
(−)-4-(5-Phenyl-pyridazin-3-yl)-1,4-diaza-bicyclo[3.2.1]octane;
(−)-4-(5-Bromo-pyridin-2-yl)-1,4-diaza-bicyclo[3.2.1]octane;
(−)-4-(6-Phenyl-pyridazin-3-yl)-1,4-diaza-bicyclo[3.2.1]octane;
(−)-4-Pyrazin-2-yl-1,4-diaza-bicyclo[3.2.1]octane;
(−)-4-Pyrimidin-5-yl-1,4-diaza-bicyclo[3.2.1]octane;
(−)-4-(5-Chloro-pyridin-3-yl)-1,4-diaza-bicyclo[3.2.1]octane;
(−)-4-[5-(3-Trifluoromethyl-phenyl)-pyridin-3-yl]-1,4-diaza-bicyclo[3.2.1]octane;
(−)-4-(3-Bromo-phenyl)-1,4-diaza-bicyclo[3.2.1]octane;
(−)-5-(1,4-Diaza-bicyclo[3.2.1]oct-4-yl)-nicotinonitrile;
(−)-4-(5-Trifluoromethyl-pyridin-3-yl)-1,4-diaza-bicyclo[3.2.1]octane;
(−)-4-[5-(2-Trifluoromethyl-phenyl)-pyridin-3-yl]-1,4-diaza-bicyclo[3.2.1]octane;
(−)-4-[5-(4-Trifluoromethyl-phenyl)-pyridin-3-yl]-1,4-diaza-bicyclo[3.2.1]octane;
(−)-4-[5-(2-Fluoro-phenyl)-pyridin-3-yl]-1,4-diaza-bicyclo[3.2.1]octane;
(−)-4-[5-(4-Fluoro-phenyl)-pyridin-3-yl]-1,4-diaza-bicyclo[3.2.1]octane;
(−)-3-(1,4-Diaza-bicyclo[3.2.1]oct-4-yl)-quinoline;
(−)-4-(3-Trifluoromethyl-pyridin-2-yl)-1,4-diaza-bicyclo[3.2.1]octane;
(−)-4-(6-Methoxy-pyridin-2-yl)-1,4-diaza-bicyclo[3.2.1]octane;
(−)-4-[5-(2-Methoxy-phenyl)-pyridin-3-yl]-1,4-diaza-bicyclo[3.2.1]octane;
(−)-4-[5-(3-Methoxy-phenyl)-pyridin-3-yl]-1,4-diaza-bicyclo[3.2.1]octane;
(−)-4-(5-o-Tolyl-pyridin-3-yl)-1,4-diaza-bicyclo[3.2.1]octane;
(−)-5-(1,4-Diaza-bicyclo[3.2.1]oct-4-yl)-nicotinic acid ethyl ester;
(−)-4-(5-Chloro-pyridin-2-yl)-1,4-diaza-bicyclo[3.2.1]octane;
(−)-4-(6-Methyl-pyridin-3-yl)-1,4-diaza-bicyclo[3.2.1]octane;
(−)-4-[5-(3-Trifluoromethyl-phenyl)-pyridin-2-yl]-1,4-diaza-bicyclo[3.2.1]octane;
(−)-4-[5-(4-Chloro-phenyl)-pyridin-2-yl]-1,4-diaza-bicyclo[3.2.1]octane;
(−)-4-(5-o-Tolyl-pyridin-2-yl)-1,4-diaza-bicyclo[3.2.1]octane;
(−)-4-[5-(3-Chloro-phenyl)-pyridin-2-yl]-1,4-diaza-bicyclo[3.2.1]octane;
(−)-4-[5-(3-Fluoro-phenyl)-pyridin-2-yl]-1,4-diaza-bicyclo[3.2.1]octane;
(−)-4-[5-(4-Chloro-phenyl)-pyridin-3-yl]-1,4-diaza-bicyclo[3.2.1]octane;
(−)-4-[5-(2,4-Dichloro-phenyl)-pyridin-3-yl]-1,4-diaza-bicyclo[3.2.1]octane;
(−)-4-[5-(3-Chloro-phenyl)-pyridin-3-yl]-1,4-diaza-bicyclo[3.2.1]octane;
(−)-4-(5-p-Tolyl-pyridin-3-yl)-1,4-diaza-bicyclo[3.2.1]octane;
(−)-4-[5-(4-Methoxy-phenyl)-pyridin-3-yl]-1,4-diaza-bicyclo[3.2.1]octane;
(−)-4-(5-Methoxy-pyridin-3-yl)-1,4-diaza-bicyclo[3.2.1]octane;
(−)-5-(1,4-Diaza-bicyclo[3.2.1]oct-4-yl)-[3,4']bipyridinyl; and
(−)-4-(2-Methyl-5-trifluoromethyl-pyridin-3-yl)-1,4-diaza-bicyclo[3.2.1]octane.

Further preferred compounds of the invention are those where n=1 and m=1 and are selected from the group consisting of:
4-(5-Bromo-pyridin-3-yl)-1,4-diaza-bicyclo[3.1.1]heptane;
4-(5-Phenyl-pyridin-3-yl)-1,4-diaza-bicyclo[3.1.1]heptane;
4-Pyridin-2-yl-1,4-diaza-bicyclo[3.1.1]heptane;
4-Pyridin-3-yl-1,4-diaza-bicyclo[3.1.1]heptane;
4-Pyridin-4-yl-1,4-diaza-bicyclo[3.1.1]heptane;
4-(5-Phenyl-pyridazin-3-yl)-1,4-diaza-bicyclo[3.1.1]heptane;
4-(5-Bromo-pyridin-2-yl)-1,4-diaza-bicyclo[3.1.1]heptane;
4-(6-Phenyl-pyridazin-3-yl)-1,4-diaza-bicyclo[3.1.1]heptane;
4-Pyrazin-2-yl-1,4-diaza-bicyclo[3.1.1]heptane;
4-Pyrimidin-5-yl-1,4-diaza-bicyclo[3.1.1]heptane;
4-(5-Chloro-pyridin-3-yl)-1,4-diaza-bicyclo[3.1.1]heptane;
4-[5-(3-Trifluoromethyl-phenyl)-pyridin-3-yl]-1,4-diaza-bicyclo[3.1.1]heptane;
4-(3-Bromo-phenyl)-1,4-diaza-bicyclo[3.1.1]heptane;
5-(1,4-Diaza-bicyclo[3.1.1]hept-4-yl)-nicotinonitrile;

4-(5-Trifluoromethyl-pyridin-3-yl)-1,4-diaza-bicyclo[3.1.1]heptane;
4-[5-(2-Trifluoromethyl-phenyl)-pyridin-3-yl]-1,4-diaza-bicyclo[3.1.1]heptane;
4-[5-(4-Trifluoromethyl-phenyl)-pyridin-3-yl]-1,4-diaza-bicyclo[3.1.1]heptane;
4-[5-(2-Fluoro-phenyl)-pyridin-3-yl]-1,4-diaza-bicyclo[3.1.1]heptane;
4-[5-(4-Fluoro-phenyl)-pyridin-3-yl]-1,4-diaza-bicyclo[3.1.1]heptane;
3-(1,4-Diaza-bicyclo[3.1.1]hept-4-yl)-quinoline;
4-(3-Trifluoromethyl-pyridin-2-yl)-1,4-diaza-bicyclo[3.1.1]heptane;
4-(6-Methoxy-pyridin-2-yl)-1,4-diaza-bicyclo[3.1.1]heptane;
4-[5-(2-Methoxy-phenyl)-pyridin-3-yl]-1,4-diaza-bicyclo[3.1.1]heptane;
4-[5-(3-Methoxy-phenyl)-pyridin-3-yl]-1,4-diaza-bicyclo[3.1.1]heptane;
4-(5-o-Tolyl-pyridin-3-yl)-1,4-diaza-bicyclo[3.1.1]heptane;
5-(1,4-Diaza-bicyclo[3.1.1]hept-4-yl)-nicotinic acid ethyl ester;
4-(5-Chloro-pyridin-2-yl)-1,4-diaza-bicyclo[3.1.1]heptane;
4-(6-Methyl-pyridin-3-yl)-1,4-diaza-bicyclo[3.1.1]heptane;
4-[5-(3-Trifluoromethyl-phenyl)-pyridin-2-yl]-1,4-diaza-bicyclo[3.1.1]heptane;
4-[5-(4-Chloro-phenyl)-pyridin-2-yl]-1,4-diaza-bicyclo[3.1.1]heptane;
4-(5-o-Tolyl-pyridin-2-yl)-1,4-diaza-bicyclo[3.1.1]heptane;
4-[5-(3-Chloro-phenyl)-pyridin-2-yl]-1,4-diaza-bicyclo[3.1.1]heptane;
4-[5-(3-Fluoro-phenyl)-pyridin-2-yl]-1,4-diaza-bicyclo[3.1.1]heptane;
4-[5-(4-Chloro-phenyl)-pyridin-3-yl]-1,4-diaza-bicyclo[3.1.1]heptane;
4-[5-(2,4-Dichloro-phenyl)-pyridin-3-yl]-1,4-diaza-bicyclo[3.1.1]heptane;
4-[5-(3-Chloro-phenyl)-pyridin-3-yl]-1,4-diaza-bicyclo[3.1.1]heptane;
4-(5-p-Tolyl-pyridin-3-yl)-1,4-diaza-bicyclo[3.1.1]heptane;
4-[5-(4-Methoxy-phenyl)-pyridin-3-yl]-1,4-diaza-bicyclo[3.1.1]heptane;
4-(5-Methoxy-pyridin-3-yl)-1,4-diaza-bicyclo[3.1.1]heptane;
5-(1,4-Diaza-bicyclo[3.1.1]hept-4-yl)-[3,4']bipyridinyl; and
4-(2-Methyl-5-trifluoromethyl-pyridin-3-yl)-1,4-diaza-bicyclo[3.1.1]heptane.

Further preferred compounds of the invention are those where n=3 and m=selected from the group consisting of:
4-(5-Bromo-pyridin-3-yl)-1,4-diaza-bicyclo[3.3.1]nonane;
4-(5-Phenyl-pyridin-3-yl)-1,4-diaza-bicyclo[3.3.1]nonane;
4-Pyridin-2-yl-1,4-diaza-bicyclo[3.3.1]nonane;
4-Pyridin-3-yl-1,4-diaza-bicyclo[3.3.1]nonane;
4-Pyridin-4-yl-1,4-diaza-bicyclo[3.3.1]nonane;
4-(5-Phenyl-pyridazin-3-yl)-1,4-diaza-bicyclo[3.3.1]nonane;
4-(5-Bromo-pyridin-2-yl)-1,4-diaza-bicyclo[3.3.1]nonane;
4-(6-Phenyl-pyridazin-3-yl)-1,4-diaza-bicyclo[3.3.1]nonane;
4-Pyrazin-2-yl-1,4-diaza-bicyclo[3.3.1]nonane;
4-Pyrimidin-5-yl-1,4-diaza-bicyclo[3.3.1]nonane;
4-(5-Chloro-pyridin-3-yl)-1,4-diaza-bicyclo[3.3.1]nonane;
4-[5-(3-Trifluoromethyl-phenyl)-pyridin-3-yl]-1,4-diaza-bicyclo[3.3.1]nonane;
4-(3-Bromo-phenyl)-1,4-diaza-bicyclo[3.3.1]nonane;
5-(1,4-Diaza-bicyclo[3.3.1]non-4-yl)-nicotinonitrile;
4-(5-Trifluoromethyl-pyridin-3-yl)-1,4-diaza-bicyclo[3.3.1]nonane;
4-[5-(2-Trifluoromethyl-phenyl)-pyridin-3-yl]-1,4-diaza-bicyclo[3.3.1]nonane;
4-[5-(4-Trifluoromethyl-phenyl)-pyridin-3-yl]-1,4-diaza-bicyclo[3.3.1]nonane;
4-[5-(2-Fluoro-phenyl)-pyridin-3-yl]-1,4-diaza-bicyclo[3.3.1]nonane;
4-[5-(4-Fluoro-phenyl)-pyridin-3-yl]-1,4-diaza-bicyclo[3.3.1]nonane;
3-(1,4-Diaza-bicyclo[3.3.1]non-4-yl)-quinoline;
4-(3-Trifluoromethyl-pyridin-2-yl)-1,4-diaza-bicyclo[3.3.1]nonane;
4-(6-Methoxy-pyridin-2-yl)-1,4-diaza-bicyclo[3.3.1]nonane;
4-[5-(2-Methoxy-phenyl)-pyridin-3-yl]-1,4-diaza-bicyclo[3.3.1]nonane;
4-[5-(3-Methoxy-phenyl)-pyridin-3-yl]-1,4-diaza-bicyclo[3.3.1]nonane;
4-(5-o-Tolyl-pyridin-3-yl)-1,4-diaza-bicyclo[3.3.1]nonane;
5-(1,4-Diaza-bicyclo[3.3.1]non-4-yl)-nicotinic acid ethyl ester;
4-(5-Chloro-pyridin-2-yl)-1,4-diaza-bicyclo[3.3.1]nonane;
4-(6-Methyl-pyridin-3-yl)-1,4-diaza-bicyclo[3.3.1]nonane;
4-[5-(3-Trifluoromethyl-phenyl)-pyridin-2-yl]-1,4-diaza-bicyclo[3.3.1]nonane;
4-[5-(4-Chloro-phenyl)-pyridin-2-yl]-1,4-diaza-bicyclo[3.3.1]nonane;
4-(5-o-Tolyl-pyridin-2-yl)-1,4-diaza-bicyclo[3.3.1]nonane;
4-[5-(3-Chloro-phenyl)-pyridin-2-yl]-1,4-diaza-bicyclo[3.3.1]nonane;
4-[5-(3-Fluoro-phenyl)-pyridin-2-yl]-1,4-diaza-bicyclo[3.3.1]nonane;
4-[5-(4-Chloro-phenyl)-pyridin-3-yl]-1,4-diaza-bicyclo[3.3.1]nonane;
4-[5-(2,4-Dichloro-phenyl)-pyridin-3-yl]-1,4-diaza-bicyclo[3.3.1]nonane;
4-[5-(3-Chloro-phenyl)-pyridin-3-yl]-1,4-diaza-bicyclo[3.3.1]nonane;
4-(5-p-Tolyl-pyridin-3-yl)-1,4-diaza-bicyclo[3.3.1]nonane;
4-[5-(4-Methoxy-phenyl)-pyridin-3-yl]-1,4-diaza-bicyclo[3.3.1]nonane;
4-(5-Methoxy-pyridin-3-yl)-1,4-diaza-bicyclo[3.3.1]nonane;
5-(1,4-Diaza-bicyclo[3.3.1]non-4-yl)-[3,4']bipyridinyl; and
4-(2-Methyl-5-trifluoromethyl-pyridin-3-yl)-1,4-diaza-bicyclo[3.3.1]nonane.

Further preferred compounds of the invention are selected from:
(+)-4-(5-Bromo-pyridin-3-yl)-1,4-diaza-bicyclo[3.3.1]nonane;
(+)-4-(5-Phenyl-pyridin-3-yl)-1,4-diaza-bicyclo[3.3.1]nonane;
(+)-4-Pyridin-2-yl-1,4-diaza-bicyclo[3.3.1]nonane;
(+)-4-Pyridin-3-yl-1,4-diaza-bicyclo[3.3.1]nonane;
(+)-4-Pyridin-4-yl-1,4-diaza-bicyclo[3.3.1]nonane;
(+)-4-(5-Phenyl-pyridazin-3-yl)-1,4-diaza-bicyclo[3.3.1]nonane;
(+)-4-(5-Bromo-pyridin-2-yl)-1,4-diaza-bicyclo[3.3.1]nonane;
(+)-4-(6-Phenyl-pyridazin-3-yl)-1,4-diaza-bicyclo[3.3.1]nonane;
(+)-4-Pyrazin-2-yl-1,4-diaza-bicyclo[3.3.1]nonane;
(+)-4-Pyrimidin-5-yl-1,4-diaza-bicyclo[3.3.1]nonane;
(+)-4-(5-Chloro-pyridin-3-yl)-1,4-diaza-bicyclo[3.3.1]nonane;

(+)-4-[5-(3-Trifluoromethyl-phenyl)-pyridin-3-yl]-1,4-diaza-bicyclo[3.3.1]nonane;
(+)-4-(3-Bromo-phenyl)-1,4-diaza-bicyclo[3.3.1]nonane;
(+)-5-(1,4-Diaza-bicyclo[3.3.1]non-4-yl)-nicotinonitrile;
(+)-4-(5-Trifluoromethyl-pyridin-3-yl)-1,4-diaza-bicyclo[3.3.1]nonane;
(+)-4-[5-(2-Trifluoromethyl-phenyl)-pyridin-3-yl]-1,4-diaza-bicyclo[3.3.1]nonane;
(+)-4-[5-(4-Trifluoromethyl-phenyl)-pyridin-3-yl]-1,4-diaza-bicyclo[3.3.1]nonane;
(+)-4-[5-(2-Fluoro-phenyl)-pyridin-3-yl]-1,4-diaza-bicyclo[3.3.1]nonane;
(+)-4-[5-(4-Fluoro-phenyl)-pyridin-3-yl]-1,4-diaza-bicyclo[3.3.1]nonane;
(+)-3-(1,4-Diaza-bicyclo[3.3.1]non-4-yl)-quinoline;
(+)-4-(3-Trifluoromethyl-pyridin-2-yl)-1,4-diaza-bicyclo[3.3.1]nonane;
(+)-4-(6-Methoxy-pyridin-2-yl)-1,4-diaza-bicyclo[3.3.1]nonane;
(+)-4-[5-(2-Methoxy-phenyl)-pyridin-3-yl]-1,4-diaza-bicyclo[3.3.1]nonane;
(+)-4-[5-(3-Methoxy-phenyl)-pyridin-3-yl]-1,4-diaza-bicyclo[3.3.1]nonane;
(+)-4-(5-o-Tolyl-pyridin-3-yl)-1,4-diaza-bicyclo[3.3.1]nonane;
(+)-5-(1,4-Diaza-bicyclo[3.3.1]non-4-yl)-nicotinic acid ethyl ester;
(+)-4-(5-Chloro-pyridin-2-yl)-1,4-diaza-bicyclo[3.3.1]nonane;
(+)-4-(6-Methyl-pyridin-3-yl)-1,4-diaza-bicyclo[3.3.1]nonane;
(+)-4-[5-(3-Trifluoromethyl-phenyl)-pyridin-2-yl]-1,4-diaza-bicyclo[3.3.1]nonane;
(+)-4-[5-(4-Chloro-phenyl)-pyridin-2-yl]-1,4-diaza-bicyclo[3.3.1]nonane;
(+)-4-(5-o-Tolyl-pyridin-2-yl)-1,4-diaza-bicyclo[3.3.1]nonane;
(+)-4-[5-(3-Chloro-phenyl)-pyridin-2-yl]-1,4-diaza-bicyclo[3.3.1]nonane;
(+)-4-[5-(3-Fluoro-phenyl)-pyridin-2-yl]-1,4-diaza-bicyclo[3.3.1]nonane;
(+)-4-[5-(4-Chloro-phenyl)-pyridin-3-yl]-1,4-diaza-bicyclo[3.3.1]nonane;
(+)-4-[5-(2,4-Dichloro-phenyl)-pyridin-3-yl]-1,4-diaza-bicyclo[3.3.1]nonane;
(+)-4-[5-(3-Chloro-phenyl)-pyridin-3-yl]-1,4-diaza-bicyclo[3.3.1]nonane;
(+)-4-(5-p-Tolyl-pyridin-3-yl)-1,4-diaza-bicyclo[3.3.1]nonane;
(+)-4-[5-(4-Methoxy-phenyl)-pyridin-3-yl]-1,4-diaza-bicyclo[3.3.1]nonane;
(+)-4-(5-Methoxy-pyridin-3-yl)-1,4-diaza-bicyclo[3.3.1]nonane;
(+)-5-(1,4-Diaza-bicyclo[3.3.1]non-4-yl)-[3,4']bipyridinyl; and
(+)-4-(2-Methyl-5-trifluoromethyl-pyridin-3-yl)-1,4-diaza-bicyclo[3.3.1]nonane.

Further preferred compounds of the invention are selected from the group consisting of:
(−)-4-(5-Bromo-pyridin-3-yl)-1,4-diaza-bicyclo[3.3.1]nonane;
(−)-4-(5-Phenyl-pyridin-3-yl)-1,4-diaza-bicyclo[3.3.1]nonane;
(−)-4-Pyridin-2-yl-1,4-diaza-bicyclo[3.3.1]nonane;
(−)-4-Pyridin-3-yl-1,4-diaza-bicyclo[3.3.1]nonane;
(−)-4-Pyridin-4-yl-1,4-diaza-bicyclo[3.3.1]nonane;
(−)-4-(5-Phenyl-pyridazin-3-yl)-1,4-diaza-bicyclo[3.3.1]nonane;
(−)-4-(5-Bromo-pyridin-2-yl)-1,4-diaza-bicyclo[3.3.1]nonane;
(−)-4-(6-Phenyl-pyridazin-3-yl)-1,4-diaza-bicyclo[3.3.1]nonane;
(−)-4-Pyrazin-2-yl-1,4-diaza-bicyclo[3.3.1]nonane;
(−)-4-Pyrimidin-5-yl-1,4-diaza-bicyclo[3.3.1]nonane;
(−)-4-(5-Chloro-pyridin-3-yl)-1,4-diaza-bicyclo[3.3.1]nonane;
(−)-4-[5-(3-Trifluoromethyl-phenyl)-pyridin-3-yl]-1,4-diaza-bicyclo[3.3.1]nonane;
(−)-4-(3-Bromo-phenyl)-1,4-diaza-bicyclo[3.3.1]nonane;
(−)-5-(1,4-Diaza-bicyclo[3.3.1]non-4-yl)-nicotinonitrile;
(−)-4-(5-Trifluoromethyl-pyridin-3-yl)-1,4-diaza-bicyclo[3.3.1]nonane;
(−)-4-[5-(2-Trifluoromethyl-phenyl)-pyridin-3-yl]-1,4-diaza-bicyclo[3.3.1]nonane;
(−)-4-[5-(4-Trifluoromethyl-phenyl)-pyridin-3-yl]-1,4-diaza-bicyclo[3.3.1]nonane;
(−)-4-[5-(2-Fluoro-phenyl)-pyridin-3-yl]-1,4-diaza-bicyclo[3.3.1]nonane;
(−)-4-[5-(4-Fluoro-phenyl)-pyridin-3-yl]-1,4-diaza-bicyclo[3.3.1]nonane;
(−)-3-(1,4-Diaza-bicyclo[3.3.1]non-4-yl)-quinoline;
(−)-4-(3-Trifluoromethyl-pyridin-2-yl)-1,4-diaza-bicyclo[3.3.1]nonane;
(−)-4-(6-Methoxy-pyridin-2-yl)-1,4-diaza-bicyclo[3.3.1]nonane;
(−)-4-[5-(2-Methoxy-phenyl)-pyridin-3-yl]-1,4-diaza-bicyclo[3.3.1]nonane;
(−)-4-[5-(3-Methoxy-phenyl)-pyridin-3-yl]-1,4-diaza-bicyclo[3.3.1]nonane;
(−)-4-(5-o-Tolyl-pyridin-3-yl)-1,4-diaza-bicyclo[3.3.1]nonane;
(−)-5-(1,4-Diaza-bicyclo[3.3.1]non-4-yl)-nicotinic acid ethyl ester;
(−)-4-(5-Chloro-pyridin-2-yl)-1,4-diaza-bicyclo[3.3.1]nonane;
(−)-4-(6-Methyl-pyridin-3-yl)-1,4-diaza-bicyclo[3.3.1]nonane;
(−)-4-[5-(3-Trifluoromethyl-phenyl)-pyridin-2-yl]-1,4-diaza-bicyclo[3.3.1]nonane;
(−)-4-[5-(4-Chloro-phenyl)-pyridin-2-yl]-1,4-diaza-bicyclo[3.3.1]nonane;
(−)-4-(5-o-Tolyl-pyridin-2-yl)-1,4-diaza-bicyclo[3.3.1]nonane;
(−)-4-[5-(3-Chloro-phenyl)-pyridin-2-yl]-1,4-diaza-bicyclo[3.3.1]nonane;
(−)-4-[(5-(3-Fluoro-phenyl)-pyridin-2-yl]-1,4-diaza-bicyclo[3.3.1]nonane;
(−)-4-[5-(4-Chloro-phenyl)-pyridin-3-yl]-1,4-diaza-bicyclo[3.3.1]nonane;
(−)-4-[5-(2,4-Dichloro-phenyl)-pyridin-3-yl]-1,4-diaza-bicyclo[3.3.1]nonane;
(−)-4-[5-(3-Chloro-phenyl)-pyridin-3-yl]-1,4-diaza-bicyclo[3.3.1]nonane;
(−)-4-(5-p-Tolyl-pyridin-3-yl)-1,4-diaza-bicyclo[3.3.1]nonane;
(−)-4-[5-(4-Methoxy-phenyl)-pyridin-3-yl]-1,4-diaza-bicyclo[3.3.1]nonane;
(−)-4-(5-Methoxy-pyridin-3-yl)-1,4-diaza-bicyclo[3.3.1]nonane;
(−)-5-(1,4-Diaza-bicyclo[3.3.1]non-4-yl)-[3,4']bipyridinyl; and
(−)-4-(2-Methyl-5-trifluoromethyl-pyridin-3-yl)-1,4-diaza-bicyclo[3.3.1]nonane.

Further preferred compounds of the invention are those where n=3 and m=2 selected from the group consisting of:

4-(5-Bromo-pyridin-3-yl)-1,4-diaza-bicyclo[3.3.2]decane;
4-(5-Phenyl-pyridin-3-yl)-1,4-diaza-bicyclo[3.3.2]decane;
4-Pyridin-2-yl-1,4-diaza-bicyclo[3.3.2]decane;
4-Pyridin-3-yl-1,4-diaza-bicyclo[3.3.2]decane;
4-Pyridin-4-yl-1,4-diaza-bicyclo[3.3.2]decane;
4-(5-Phenyl-pyridazin-3-yl)-1,4-diaza-bicyclo[3.3.2]decane;
4-(5-Bromo-pyridin-2-yl)-1,4-diaza-bicyclo[3.3.2]decane;
4-(6-Phenyl-pyridazin-3-yl)-1,4-diaza-bicyclo[3.3.2]decane;
4-Pyrazin-2-yl-1,4-diaza-bicyclo[3.3.2]decane;
4-Pyrimidin-5-yl-1,4-diaza-bicyclo[3.3.2]decane;
4-(5-Chloro-pyridin-3-yl)-1,4-diaza-bicyclo[3.3.2]decane;
4-[5-(3-Trifluoromethyl-phenyl)-pyridin-3-yl]-1,4-diaza-bicyclo[3.3.2]decane;
4-(3-Bromo-phenyl)-1,4-diaza-bicyclo[3.3.2]decane;
5-(1,4-Diaza-bicyclo[3.3.2]dec-4-yl)-nicotinonitrile;
4-(5-Trifluoromethyl-pyridin-3-yl)-1,4-diaza-bicyclo[3.3.2]decane;
4-[5-(2-Trifluoromethyl-phenyl)-pyridin-3-yl]-1,4-diaza-bicyclo[3.3.2]decane;
4-[5-(4-Trifluoromethyl-phenyl)-pyridin-3-yl]-1,4-diaza-bicyclo[3.3.2]decane;
4-[5-(2-Fluoro-phenyl)-pyridin-3-yl]-1,4-diaza-bicyclo[3.3.2]decane;
4-[5-(4-Fluoro-phenyl)-pyridin-3-yl]-1,4-diaza-bicyclo[3.3.2]decane;
3-(1,4-Diaza-bicyclo[3.3.2]dec-4-yl)-quinoline;
4-(3-Trifluoromethyl-pyridin-2-yl)-1,4-diaza-bicyclo[3.3.2]decane;
4-(6-Methoxy-pyridin-2-yl)-1,4-diaza-bicyclo[3.3.2]decane;
4-[5-(2-Methoxy-phenyl)-pyridin-3-yl]-1,4-diaza-bicyclo[3.3.2]decane;
4-[5-(3-Methoxy-phenyl)-pyridin-3-yl]-1,4-diaza-bicyclo[3.3.2]decane;
4-(5-o-Tolyl-pyridin-3-yl)-1,4-diaza-bicyclo[3.3.2]decane;
5-(1,4-Diaza-bicyclo[3.3.2]dec-4-yl)-nicotinic acid ethyl ester;
4-(5-Chloro-pyridin-2-yl)-1,4-diaza-bicyclo[3.3.2]decane;
4-(6-Methyl-pyridin-3-yl)-1,4-diaza-bicyclo[3.3.2]decane;
4-[5-(3-Trifluoromethyl-phenyl)-pyridin-2-yl]-1,4-diaza-bicyclo[3.3.2]decane;
4-[5-(4-Chloro-phenyl)-pyridin-2-yl]-1,4-diaza-bicyclo[3.3.2]decane;
4-(5-o-Tolyl-pyridin-2-yl)-1,4-diaza-bicyclo[3.3.2]decane;
4-[5-(3-Chloro-phenyl)-pyridin-2-yl]-1,4-diaza-bicyclo[3.3.2]decane;
4-[5-(3-Fluoro-phenyl)-pyridin-2-yl]-1,4-diaza-bicyclo[3.3.2]decane;
4-[5-(4-Chloro-phenyl)-pyridin-3-yl]-1,4-diaza-bicyclo[3.3.2]decane;
4-[5-(2,4-Dichloro-phenyl)-pyridin-3-yl]-1,4-diaza-bicyclo[3.3.2]decane;
4-[5-(3-Chloro-phenyl)-pyridin-3-yl]-1,4-diaza-bicyclo[3.3.2]decane;
4-(5-p-Tolyl-pyridin-3-yl)-1,4-diaza-bicyclo[3.3.2]decane;
4-[5-(4-Methoxy-phenyl)-pyridin-3-yl]-1,4-diaza-bicyclo[3.3.2]decane;
4-(5-Methoxy-pyridin-3-yl)-1,4-diaza-bicyclo[3.3.2]decane;
5-(1,4-Diaza-bicyclo[3.3.2]dec-4-yl)-[3,4']bipyridinyl; and
4-(2-Methyl-5-trifluoromethyl-pyridin-3-yl)-1,4-diaza-bicyclo[3.3.2]decane.

Further preferred compounds of the invention are selected from the group consisting of:

(+)-4-(5-Bromo-pyridin-3-yl)-1,4-diaza-bicyclo[3.3.2]decane;
(+)-4-(5-Phenyl-pyridin-3-yl)-1,4-diaza-bicyclo[3.3.2]decane;
(+)-4-Pyridin-2-yl-1,4-diaza-bicyclo[3.3.2]decane;
(+)-4-Pyridin-3-yl-1,4-diaza-bicyclo[3.3.2]decane;
(+)-4-Pyridin-4-yl-1,4-diaza-bicyclo[3.3.2]decane;
(+)-4-(5-Phenyl-pyridazin-3-yl)-1,4-diaza-bicyclo[3.3.2]decane;
(+)-4-(5-Bromo-pyridin-2-yl)-1,4-diaza-bicyclo[3.3.2]decane;
(+)-4-(6-Phenyl-pyridazin-3-yl)-1,4-diaza-bicyclo[3.3.2]decane;
(+)-4-Pyrazin-2-yl-1,4-diaza-bicyclo[3.3.2]decane;
(+)-4-Pyrimidin-5-yl-1,4-diaza-bicyclo[3.3.2]decane;
(+)-4-(5-Chloro-pyridin-3-yl)-1,4-diaza-bicyclo[3.3.2]decane;
(+)-4-[5-(3-Trifluoromethyl-phenyl)-pyridin-3-yl]-1,4-diaza-bicyclo[3.3.2]decane;
(+)-4-(3-Bromo-phenyl)-1,4-diaza-bicyclo[3.3.2]decane;
(+)-5-(1,4-Diaza-bicyclo[3.3.2]dec-4-yl)-nicotinonitrile;
(+)-4-(5-Trifluoromethyl-pyridin-3-yl)-1,4-diaza-bicyclo[3.3.2]decane;
(+)-4-[5-(2-Trifluoromethyl-phenyl)-pyridin-3-yl]-1,4-diaza-bicyclo[3.3.2]decane;
(+)-4-[5-(4-Trifluoromethyl-phenyl)-pyridin-3-yl]-1,4-diaza-bicyclo[3.3.2]decane;
(+)-4-[5-(2-Fluoro-phenyl)-pyridin-3-yl]-1,4-diaza-bicyclo[3.3.2]decane;
(+)-4-[5-(4-Fluoro-phenyl)-pyridin-3-yl]-1,4-diaza-bicyclo[3.3.2]decane;
(+)-3-(1,4-Diaza-bicyclo[3.3.2]dec-4-yl)-quinoline;
(+)-4-(3-Trifluoromethyl-pyridin-2-yl)-1,4-diaza-bicyclo[3.3.2]decane;
(+)-4-(6-Methoxy-pyridin-2-yl)-1,4-diaza-bicyclo[3.3.2]decane;
(+)-4-[5-(2-Methoxy-phenyl)-pyridin-3-yl]-1,4-diaza-bicyclo[3.3.2]decane;
(+)-4-[5-(3-Methoxy-phenyl)-pyridin-3-yl]-1,4-diaza-bicyclo[3.3.2]decane;
(+)-4-(5-o-Tolyl-pyridin-3-yl)-1,4-diaza-bicyclo[3.3.2]decane;
(+)-5-(1,4-Diaza-bicyclo[3.3.2]dec-4-yl)-nicotinic acid ethyl ester;
(+)-4-(5-Chloro-pyridin-2-yl)-1,4-diaza-bicyclo[3.3.2]decane;
(+)-4-(6-Methyl-pyridin-3-yl)-1,4-diaza-bicyclo[3.3.2]decane;
(+)-4-[5-(3-Trifluoromethyl-phenyl)-pyridin-2-yl]-1,4-diaza-bicyclo[3.3.2]decane;
(+)-4-[5-(4-Chloro-phenyl)-pyridin-2-yl]-1,4-diaza-bicyclo[3.3.2]decane;
(+)-4-(5-o-Tolyl-pyridin-2-yl)-1,4-diaza-bicyclo[3.3.2]decane;
(+)-4-[5-(3-Chloro-phenyl)-pyridin-2-yl]-1,4-diaza-bicyclo[3.3.2]decane;
(+)-4-[5-(3-Fluoro-phenyl)-pyridin-2-yl]-1,4-diaza-bicyclo[3.3.2]decane;
(+)-4-[5-(4-Chloro-phenyl)-pyridin-3-yl]-1,4-diaza-bicyclo[3.3.2]decane;
(+)-4-[5-(2,4-Dichloro-phenyl)-pyridin-3-yl]-1,4-diaza-bicyclo[3.3.2]decane;
(+)-4-[5-(3-Chloro-phenyl)-pyridin-3-yl]-1,4-diaza-bicyclo[3.3.2]decane;

(+)-4-(5-p-Tolyl-pyridin-3-yl)-1,4-diaza-bicyclo[3.3.2]decane;
(+)-4-[5-(4-Methoxy-phenyl)-pyridin-3-yl]-1,4-diaza-bicyclo[3.3.2]decane;
(+)-4-(5-Methoxy-pyridin-3-yl)-1,4-diaza-bicyclo[3.3.2]decane;
(+)-5-(1,4-Diaza-bicyclo[3.3.2]dec-4-yl)-[3,4']bipyridinyl; and
(+)-4-(2-Methyl-5-trifluoromethyl-pyridin-3-yl)-1,4-diaza-bicyclo[3.3.2]decane.

Further preferred compounds of the invention are selected from the group consisting of:
(−)-4-(5-Bromo-pyridin-3-yl)-1,4-diaza-bicyclo[3.3.2]decane;
(−)-4-(5-Phenyl-pyridin-3-yl)-1,4-diaza-bicyclo[3.3.2]decane;
(−)-4-Pyridin-2-yl-1,4-diaza-bicyclo[3.3.2]decane;
(−)-4-Pyridin-3-yl-1,4-diaza-bicyclo[3.3.2]decane;
(−)-4-Pyridin-4-yl-1,4-diaza-bicyclo[3.3.2]decane;
(−)-4-(5-Phenyl-pyridazin-3-yl)-1,4-diaza-bicyclo[3.3.2]decane;
(−)-4-(5-Bromo-pyridin-2-yl)-1,4-diaza-bicyclo[3.3.2]decane;
(−)-4-(6-Phenyl-pyridazin-3-yl)-1,4-diaza-bicyclo[3.3.2]decane;
(−)-4-Pyrazin-2-yl-1,4-diaza-bicyclo[3.3.2]decane;
(−)-4-Pyrimidin-5-yl-1,4-diaza-bicyclo[3.3.2]decane;
(−)-4-(5-Chloro-pyridin-3-yl)-1,4-diaza-bicyclo[3.3.2]decane;
(−)-4-[5-(3-Trifluoromethyl-phenyl)-pyridin-3-yl]-1,4-diaza-bicyclo[3.3.2]decane;
(−)-4-(3-Bromo-phenyl)-1,4-diaza-bicyclo[3.3.2]decane;
(−)-5-(1,4-Diaza-bicyclo[3.3.2]dec-4-yl)-nicotinonitrile;
(−)-4-(5-Trifluoromethyl-pyridin-3-yl)-1,4-diaza-bicyclo[3.3.2]decane;
(−)-4-[5-(2-Trifluoromethyl-phenyl)-pyridin-3-yl]-1,4-diaza-bicyclo[3.3.2]decane;
(−)-4-[5-(4-Trifluoromethyl-phenyl)-pyridin-3-yl]-1,4-diaza-bicyclo[3.3.2]decane;
(−)-4-[5-(2-Fluoro-phenyl)-pyridin-3-yl]-1,4-diaza-bicyclo[3.3.2]decane;
(−)-4-[5-(4-Fluoro-phenyl)-pyridin-3-yl]-1,4-diaza-bicyclo[3.3.2]decane;
(−)-3-(1,4-Diaza-bicyclo[3.3.2]dec-4-yl)-quinoline;
(−)-4-(3-Trifluoromethyl-pyridin-2-yl)-1,4-diaza-bicyclo[3.3.2]decane;
(−)-4-(6-Methoxy-pyridin-2-yl)-1,4-diaza-bicyclo[3.3.2]decane;
(−)-4-[5-(2-Methoxy-phenyl)-pyridin-3-yl]-1,4-diaza-bicyclo[3.3.2]decane;
(−)-4-[5-(3-Methoxy-phenyl)-pyridin-3-yl]-1,4-diaza-bicyclo[3.3.2]decane;
(−)-4-(5-o-Tolyl-pyridin-3-yl)-1,4-diaza-bicyclo[3.3.2]decane;
(−)-5-(1,4-Diaza-bicyclo[3.3.2]dec-4-yl)-nicotinic acid ethyl ester;
(−)-4-(5-Chloro-pyridin-2-yl)-1,4-diaza-bicyclo[3.3.2]decane;
(−)-4-(6-Methyl-pyridin-3-yl)-1,4-diaza-bicyclo[3.3.2]decane;
(−)-4-[5-(3-Trifluoromethyl-phenyl)-pyridin-2-yl]-1,4-diaza-bicyclo[3.3.2]decane;
(−)-4-[5-(4-Chloro-phenyl)-pyridin-2-yl]-1,4-diaza-bicyclo[3.3.2]decane;
(−)-4-(5-o-Tolyl-pyridin-2-yl)-1,4-diaza-bicyclo[3.3.2]decane;
(−)-4-[5-(3-Chloro-phenyl)-pyridin-2-yl]-1,4-diaza-bicyclo[3.3.2]decane;
(−)-4-[5-(3-Fluoro-phenyl)-pyridin-2-yl]-1,4-diaza-bicyclo[3.3.2]decane;
(−)-4-[5-(4-Chloro-phenyl)-pyridin-3-yl]-1,4-diaza-bicyclo[3.3.2]decane;
(−)-4-[5-(2,4-Dichloro-phenyl)-pyridin-3-yl]-1,4-diaza-bicyclo[3.3.2]decane;
(−)-4-[5-(3-Chloro-phenyl)-pyridin-3-yl]-1,4-diaza-bicyclo[3.3.2]decane;
(−)-4-(5-p-Tolyl-pyridin-3-yl)-1,4-diaza-bicyclo[3.3.2]decane;
(−)-4-[5-(4-Methoxy-phenyl)-pyridin-3-yl]-1,4-diaza-bicyclo[3.3.2]decane;
(−)-4-(5-Methoxy-pyridin-3-yl)-1,4-diaza-bicyclo[3.3.2]decane;
(−)-5-(1,4-Diaza-bicyclo[3.3.2]dec-4-yl)-[3,4']bipyridinyl; and
(−)-4-(2-Methyl-5-trifluoromethyl-pyridin-3-yl)-1,4-diaza-bicyclo[3.3.2]decane.

Further preferred compounds of the invention are those where n=3 and m=3 selected from the group consisting of:
4-(5-Bromo-pyridin-3-yl)-1,4-diaza-bicyclo[3.3.3]undecane;
4-(5-Phenyl-pyridin-3-yl)-1,4-diaza-bicyclo[3.3.3]undecane;
4-Pyridin-2-yl-1,4-diaza-bicyclo[3.3.3]undecane;
4-Pyridin-3-yl-1,4-diaza-bicyclo[3.3.3]undecane;
4-Pyridin-4-yl-1,4-diaza-bicyclo[3.3.3]undecane;
4-(5-Phenyl-pyridazin-3-yl)-1,4-diaza-bicyclo[3.3.3]undecane;
4-(5-Bromo-pyridin-2-yl)-1,4-diaza-bicyclo[3.3.3]undecane;
4-(6-Phenyl-pyridazin-3-yl)-1,4-diaza-bicyclo[3.3.3]undecane;
4-Pyrazin-2-yl-1,4-diaza-bicyclo[3.3.3]undecane;
4-Pyrimidin-5-yl-1,4-diaza-bicyclo[3.3.3]undecane;
4-(5-Chloro-pyridin-3-yl)-1,4-diaza-bicyclo[3.3.3]undecane;
4-[5-(3-Trifluoromethyl-phenyl)-pyridin-3-yl]-1,4-diaza-bicyclo[3.3.3]undecane;
4-(3-Bromo-phenyl)-1,4-diaza-bicyclo[3.3.3]undecane;
5-(1,4-Diaza-bicyclo[3.3.3]undec-4-yl)-nicotinonitrile;
4-(5-Trifluoromethyl-pyridin-3-yl)-1,4-diaza-bicyclo[3.3.3]undecane;
4-[5-(2-Trifluoromethyl-phenyl)-pyridin-3-yl]-1,4-diaza-bicyclo[3.3.3]undecane;
4-[5-(4-Trifluoromethyl-phenyl)-pyridin-3-yl]-1,4-diaza-bicyclo[3.3.3]undecane;
4-[5-(2-Fluoro-phenyl)-pyridin-3-yl]-1,4-diaza-bicyclo[3.3.3]undecane;
4-[5-(4-Fluoro-phenyl)-pyridin-3-yl]-1,4-diaza-bicyclo[3.3.3]undecane;
3-(1,4-Diaza-bicyclo[3.3.3]undec-4-yl)-quinoline;
4-(3-Trifluoromethyl-pyridin-2-yl)-1,4-diaza-bicyclo[3.3.3]undecane;
4-(6-Methoxy-pyridin-2-yl)-1,4-diaza-bicyclo[3.3.3]undecane;
4-[5-(2-Methoxy-phenyl)-pyridin-3-yl]-1,4-diaza-bicyclo[3.3.3]undecane;
4-[5-(3-Methoxy-phenyl)-pyridin-3-yl]-1,4-diaza-bicyclo[3.3.3]undecane;
4-(5-o-Tolyl-pyridin-3-yl)-1,4-diaza-bicyclo[3.3.3]undecane;
5-(1,4-Diaza-bicyclo[3.3.3]undec-4-yl)-nicotinic acid ethyl ester;

4-(5-Chloro-pyridin-2-yl)-1,4-diaza-bicyclo[3.3.3]undecane;
4-(6-Methyl-pyridin-3-yl)-1,4-diaza-bicyclo[3.3.3]undecane;
4-[5-(3-Trifluoromethyl-phenyl)-pyridin-2-yl]-1,4-diaza-bicyclo[3.3.3]undecane;
4-[5-(4-Chloro-phenyl)-pyridin-2-yl]-1,4-diaza-bicyclo[3.3.3]undecane;
4-(5-o-Tolyl-pyridin-2-yl)-1,4-diaza-bicyclo[3.3.3]undecane;
4-[5-(3-Chloro-phenyl)-pyridin-2-yl]-1,4-diaza-bicyclo[3.3.3]undecane;
4-[5-(3-Fluoro-phenyl)-pyridin-2-yl]-1,4-diaza-bicyclo[3.3.3]undecane;
4-[5-(4-Chloro-phenyl)-pyridin-3-yl]-1,4-diaza-bicyclo[3.3.3]undecane;
4-[5-(2,4-Dichloro-phenyl)-pyridin-3-yl]-1,4-diaza-bicyclo[3.3.3]undecane;
4-[5-(3-Chloro-phenyl)-pyridin-3-yl]-1,4-diaza-bicyclo[3.3.3]undecane;
4-(5-p-Tolyl-pyridin-3-yl)-1,4-diaza-bicyclo[3.3.3]undecane;
4-[5-(4-Methoxy-phenyl)-pyridin-3-yl]-1,4-diaza-bicyclo[3.3.3]undecane;
4-(5-Methoxy-pyridin-3-yl)-1,4-diaza-bicyclo[3.3.3]undecane;
5-(1,4-Diaza-bicyclo[3.3.3]undec-4-yl)-[3,4']bipyridinyl; and
4-(2-Methyl-5-trifluoromethyl-pyridin-3-yl)-1,4-diaza-bicyclo[3.3.3]undecane.

The term "alkyl", as used herein, unless otherwise indicated, includes saturated monovalent hydrocarbon radicals having straight or branched moieties. Examples of alkyl groups include, but are not limited to, methyl, ethyl, propyl, isopropyl, and t-butyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings. Examples of bicycloalkyl groups include, but are not limited to, bicyclo-[2.2.2]-octyl and norbornyl. The term "cycloalkenyl" and "bicycloalkenyl" refer to non-aromatic carbocyclic cycloalkyl and bicycloalkyl moieties as defined above, except comprising of one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclohexenyl. A non-limiting example of a bicycloalkenyl group is norborenyl. Cycloalkyl, cycloalkenyl, bicycloalkyl, and bicycloalkenyl groups also include groups similar to those described above for each of these respective categories, but which are substituted with one or more oxo moieties. Examples of such groups with oxo moieties include, but are not limited to oxocyclopentyl, oxocyclobutyl, oxocyclopentenyl, and norcamphoryl.

The term "aryl", as used herein, unless otherwise indicated, includes an organic radical derived from an aromatic hydrocarbon by removal of one hydrogen atom. Examples of aryl groups include, but are not limited to phenyl and naphthyl.

The terms "heterocyclic" and "heterocycloalkyl", as used herein, refer to non-aromatic cyclic groups containing one or more heteroatoms, preferably from one to four heteroatoms, each selected from O, S and N. "Heterobicycloalkyl" groups are non-aromatic two-ringed cyclic groups, wherein at least one of the rings contains a heteroatom (O, S, or N). The heterocyclic groups of this invention can also include ring systems substituted with one or more oxo moieties. Examples of non-aromatic heterocyclic groups include, but are not limited to, aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydropyranyl, tetrahydrothienyl, tetrahydrothiopyranyl, piperidino, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinuclidinyl and quinolizinyl.

The term "heteroaryl", as used herein, refers to aromatic groups containing one or more heteroatoms (O, S, or N). A multicyclic group containing one or more heteroatoms wherein at least one ring of the group is aromatic is a "heteroaryl" group. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl, heterocyclic and heterocycloalkyl groups may be C-attached or N-attached (where such is possible). For instance, a group derived from pyrrole may be pyrrol-1-yl (N-attached) or pyrrol-3-yl (C-attached).

Unless otherwise indicated, the term "one or more substituents", as used herein, refers to from one to the maximum number of substituents possible based on the number of available bonding sites.

The term "treatment", as used herein, refers to reversing, alleviating, inhibiting the progress of, or preventing the disorder or condition to which such term applies, or one or more symptoms of such condition or disorder. The term "treatment", as used herein, refers to the act of treating, as "treating" is defined immediately above.

Compounds of formula I may contain chiral centers and therefore may exist in different enantiomeric and diastereomeric forms. Individual isomers can be obtained by known methods, such as optical resolution, optically selective reaction, or chromatographic separation in the preparation of the final product or its intermediate. This invention relates to all optical isomers and all stereoisomers of compounds of the formula I, both as racemic mixtures and as individual enantiomers and diastereomers of such compounds, and mixtures thereof, and to all pharmaceutical compositions and methods of treatment defined above that contain or employ them, respectively.

In so far as the compounds of formula I of this invention are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the base compounds of this invention are readily prepared by treating the base compound with a substantially equivalent amount of the chosen mineral or organic acid in an aqueous solvent or in a suitable organic solvent, such as methanol or ethanol. Upon careful evaporation of the solvent, the desired solid salt is readily obtained. The acids which are used to prepare the pharmaceutically acceptable acid addition salts of the aforementioned base compounds of this invention are those which form non-toxic acid addition salts, i.e., salts containing pharmaceutically acceptable anions, such as the hydrochloride, hydrobromide, hydroiodide, nitrate, sulfate or bisulfate, phosphate or acid phosphate, acetate, lactate, citrate or acid citrate, tartrate or bi-tartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate))salts.

The present invention also includes isotopically labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the present invention include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples below, by substituting a readily available isotopically labeled reagent for a non-isotopically labeled reagent.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), Tourette's Syndrome, particularly, nicotine dependency, addiction and withdrawal; including use in smoking cessation therapy in a mammal, comprising an amount of a compound of the formula I, or a pharmaceutically acceptable salt thereof, that is effective in treating such disorder or condition and a pharmaceutically acceptable carrier.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), Tourette's Syndrome, particularly, nicotine dependency, addiction and withdrawal; including use in smoking cessation therapy in a mammal, comprising administering to a mammal in need of such treatment an amount of a compound of the formula I, or a pharmaceutically acceptable salt thereof, that is effective in treating such disorder or condition.

The present invention also relates to a pharmaceutical composition for treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), Tourette's Syndrome, particularly, nicotine dependency, addiction and withdrawal; including use in smoking cessation therapy in a mammal, comprising an nicotinic receptor modulating amount of a compound of the formula I, or a pharmaceutically acceptable salt thereof, and a pharmaceutically acceptable carrier.

The present invention also relates to a method of treating a disorder or condition selected from inflammatory bowel disease (including but not limited to ulcerative colitis, pyoderma gangrenosum and Crohn's disease), irritable bowel syndrome, spastic dystonia, chronic pain, acute pain, celiac sprue, pouchitis, vasoconstriction, anxiety, panic disorder, depression, bipolar disorder, autism, sleep disorders, jet lag, amyotrophic lateral sclerosis (ALS), cognitive dysfunction, drug/toxin-induced cognitive impairment (e.g., from alcohol, barbiturates, vitamin deficiencies, recreational drugs, lead, arsenic, mercury), disease-induced cognitive impairment (e.g., arising from Alzheimer's disease (senile dementia), vascular dementia, Parkinson's disease, multiple sclerosis, AIDS, encephalitis, trauma, renal and hepatic encephalopathy, hypothyroidism, Pick's disease, Korsakoff's syndrome and frontal and subcortical dementia), hypertension, bulimia, anorexia, obesity, cardiac arrhythmias, gastric acid hypersecretion, ulcers, pheochromocytoma, progressive supramuscular palsy, chemical dependencies and addictions (e.g., dependencies on, or addictions to nicotine (and/or tobacco products), alcohol, benzodiazepines, barbiturates, opioids or cocaine), headache, migraine, stroke, traumatic brain injury (TBI), obsessive-compulsive disorder (OCD), psychosis, Huntington's chorea, tardive dyskinesia, hyperkinesia, dyslexia, schizophrenia, multi-infarct dementia, age-related cognitive decline, epilepsy, including petit mal absence epilepsy, attention deficit hyperactivity disorder (ADHD), Tourette's Syndrome, particularly, nicotine dependency, addiction and withdrawal; including use in smoking cessation therapy in a mammal, comprising administering to a mammal in need of such treatment a nicotinic receptor modulating amount of a compound of the formula I, or a pharmaceutically acceptable salt thereof.

DETAILED DESCRIPTION OF THE INVENTION

Compounds of the formula I can be readily prepared according to the methods described below. In the reaction schemes and discussion that follow, A, B, D, E, and F, unless otherwise indicated, are defined as they are above in the definition of compounds of the formula I.

As used herein, the expression "inert reaction solvent" refers to a solvent system in which the components do not interact with starting materials, reagents, or intermediates or products in a manner which adversely affects the yield of the desired product.

During any of the following synthetic sequences it may be necessary and/or desirable to protect sensitive or reactive groups on any of the molecules concerned. This may be achieved by means of conventional protecting groups, such as those described in T. W. Greene and P. G. M. Wuts, Protective Groups in Organic Synthesis, John Wiley & Sons, 1999.

Referring to Scheme I, a compound of formula I can be prepared by the coupling of a compound of formula II to a compound of formula II, wherein X is a leaving group or a group that has the ability to undergo oxidative addition (e.g., fluoride, chloride, bromide, iodide, triflate, methyl sulfide, alkyl sulfide, aryl sulfide, alkyl sulfoxide, or aryl sulfoxide) in the presence or absence of base. This coupling can be facilitated by the use of an organometallic reagent such as palladium, nickel or copper and the preferred method is that of Buchwald as described in: Wolfe, J. P.; Buchwald, S. L. *J. Org. Chem.* 2000, 65, 1144-1157; Wolfe et al *J. Org. Chem.* 2000, 65, 1158-1174; Wolfe, J. P.; Buchwald, S. L. *J. Org. Chem.* 1997, 62, 6066-6068.

In this coupling process, the palladium catalyst may be formed from the combination of a palladium compound selected from, but not limited to, the group consisting of palladium(II) acetate, palladium(II) chloride, bis-acetonitrile palladium(II) chloride, bis-benzonitrile palladium(II) chloride, palladium(II) bromide, tris(dibenzylideneacetone)dipalladium(0), tris(dibenzylideneacetone)dipalladium(0) chloroform adduct, palladium (0) tetrakis(triphenylphosphine), allyl palladium chloride dimer, dichloro[1,1'-bis(diphenylphosphino)ferrocene]palladium (II) dichloromethane adduct; more preferably tris(dibenzylideneacetone)dipalladium(0); and a phosphine ligand selected from, but not limited to, 1,1'-bis(diphenylphosphino)ferrocene, 1,2-bis(diphenylphosphino)ethane, 1,3-bis(diphenylphosphino)propane, 2,2'-bis(diphenylphosphino)-1,1'-binaphthyl, dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)-biphenyl, 2-(di-tert-butylphosphino)-biphenyl, 2-dicyclohexylphosphino-2'-(N,N-dimethylamino)biphenyl, or 2-di-tert-butylphosphino-2'-(N,N-dimethylamino)biphenyl; more preferably 2,2'-bis(diphenylphosphino)-1,1'-binaphthyl.

This step is conducted in the presence or absence of a base selected from, but not limited to, triethylamine, diisopropylamine, pyridine, 2,6-lutidine, sodium or potassium hydroxide, lithium or sodium or potassium or cesium carbonate, cesium fluoride, sodium or potassium tert-butoxide, sodium or potassium or cesium acetate, diisopropylethylamine, and 1,8-diazabicyclo[5.4.0]undec-7-ene; more preferably sodium tert-butoxide.

The reaction may be carried out in the presence or absence of an inert reaction solvent such as water, methanol, ethanol, isopropanol, acetonitrile, methylene chloride, chloroform, 1,2-dichloroethane, tetrahydrofuran, diethylether, dioxane, 1,2-dimethoxyethane, benzene, toluene, dimethylformamide, or dimethylsulfoxide, more preferably toluene. The aforesaid process of Scheme I can normally be carried out at a temperature between from about −10° C. to about 150° C., preferably near 110° C.

Scheme I

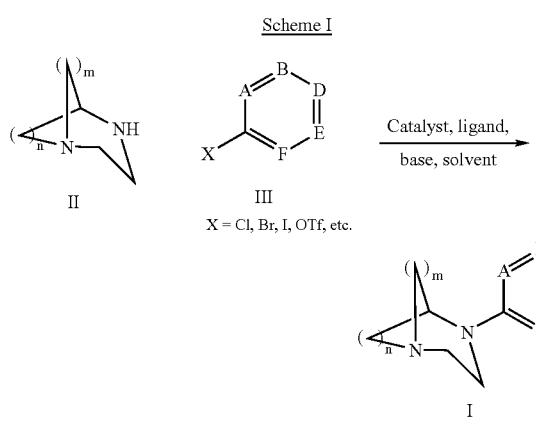

X = Cl, Br, I, OTf, etc.

A compound of formula II can be prepared by methods known in the literature or through other means by those skilled in the art. In the compound of formula III, X is defined as a functional group that has leaving group ability and/or the ability to undergo oxidative addition such as, but not limited to, F, Cl, Br, I, triflate, methyl sulfide, alkyl sulfide, aryl sulfide, alkyl sulfoxide, or aryl sulfoxide.

A compound of formula II where m=1 and n=1 can be prepare by two different procedures which are shown in Scheme II and III. Referring to Scheme II, (4-benzyl-piperazin-2-yl)-methanol, IV, was made by the procedure of Naylor, et al. *J. Med. Chem.* 1993, 36, 2075, and the secondary amine functional group was protected as the trifluoroacetamide giving a compound of formula V according to the procedures described in T. W. Greene and P. G. M. Wuts, Protective Groups in Organic Synthesis, John Wiley & Sons, 1999. The procedure using trifluoroacetic anhydride and pyridine with dichloromethane as a solvent from 0° C. to ambient temperature is preferred. The benzyl group in V is removed according to the procedures described in T. W. Greene and P. G. M. Wuts, Protective Groups in Organic Synthesis, John Wiley & Sons, 1999, to provide a compound of formula VI. The procedure using hydrogen gas at 50 psi and 10% palladium on carbon as a catalyst and ethanol/concentrated HCl as the solvent at ambient temperature is preferred. Treatment of a compound of formula VI with diethyl azodicarboxylate or diisopropyl azodicarboxylate, where diethyl azodicarboxylate is preferred and a phosphine reagent such as, but not limited to, dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)-biphenyl, 2-(di-tert-butylphosphino)-biphenyl, 2-dicyclohexylphosphino-2'-(N,N-dimethylamino)biphenyl, 2-di-tert-butylphosphino-2'-(N,N-dimethylamino)biphenyl or polymer supported triphenylphosphine; more preferably triphenylphosphine in an inert reaction solvent such as water, methanol, ethanol, isopropanol, acetonitrile, methylene chloride, chloroform, 1,2-dichloroethane, tetrahydrofuran, diethylether, 1,4-dioxane, 1,2-dimethoxyethane, benzene, toluene, dimethylformamide, or dimethylsulfoxide, more preferably tetrahydrofuran at 0° C. to 100° C., where 20° C. is preferred results in a diazabicycle compound of formula VII. Alternative methods for this conversion would include converting the primary alcohol functional group of VI in to a good leaving group such as, but not limited to, Cl, Br, I, tosylate, mesylate followed by cyclization to the desired bicycle VII under thermal conditions with or without the addition of a base. The trifluoroacetamide group in VII is removed according to the procedures described in T. W. Greene and P. G. M. Wuts, Protective Groups in Organic Synthesis, John Wiley & Sons, 1999, where the procedure using sodium carbonate in a methanol/water reaction solvent at 60° C. is preferred to form a compound of formula II, where m=1 and n=1.

Scheme II

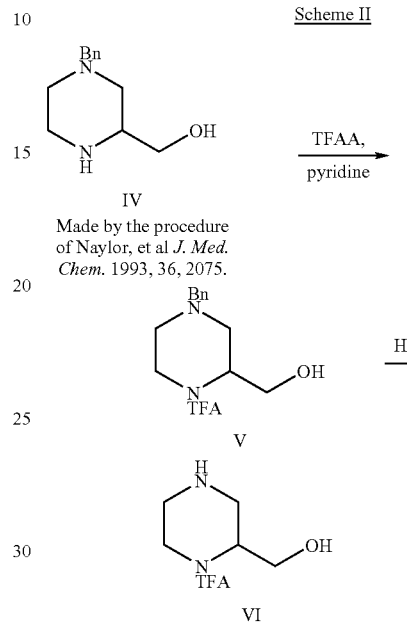

IV
Made by the procedure of Naylor, et al *J. Med. Chem.* 1993, 36, 2075.

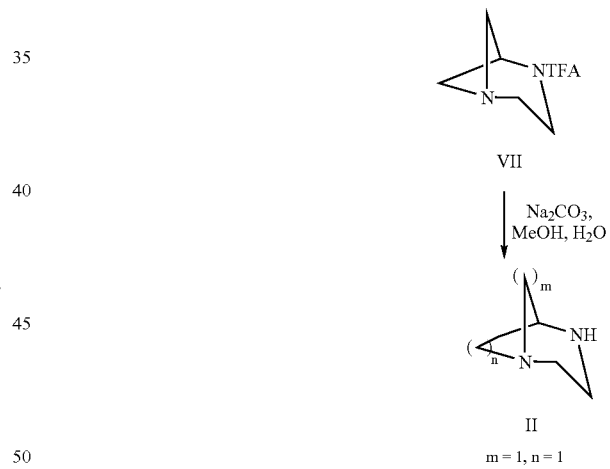

m = 1, n = 1

The second method for preparing a compound of formula II where m=1 and n=1 is described in Scheme III. Referring to Scheme III, commercially available N-benzhydrylazetidine-3-ol was converted to a compound of formula VIII using the procedure of Sum, F. W. and Hu, B. in WO 02/06221. The amine of compound VIII is acylated with bromoacetyl bromide or bromoacetyl chloride in a suitable inert solvent or mixture of solvents such as, but not limited to, toluene, benzene, methylene chloride, 1,2-dichloroethane, 1,4-dioxane or water in the presence of a suitable base such as, but not limited to, triethylamine, diisopropyethylamine, pyridine, 2,6-lutidine, 1,8-diazabicyclo[5.4.0]undec-7-ene, sodium or potassium carbonate, sodium or potassium bicarbonate, sodium or potassium hydroxide. The most preferred conditions use bromoacetyl bromide in a mixture of toluene and saturated aqueous sodium bicarbonate solution to give a compound of formula IX. The compound of formula IX is heated under reflux in an inert solvent such as, but not limited to toluene, tetrahydrofuran, methylene chloride, 1,2-dichloroethane, dimethylformamide, dimethylsulfoxide, 1,2-dimethoxyethane or 1,4-dioxane, with the more preferred solvent being toluene, to form a compound of formula X. The benzhydryl protecting group of compound X is removed according to the procedures described in T. W. Greene and P. G. M. Wuts, Protective Groups in Organic Synthesis, John Wiley & Sons, 1999, to provide a compound of formula XI. The procedure using hydrogen gas at 50 psi and 10% palladium on carbon as a catalyst and ethanol is preferred. Lactam XI is reduced with a suitable reducing agent such as, but not limited to, lithium aluminum hydride, borane, alane, or di-isobutyl aluminum hydride, where lithium aluminum hydride is preferred in an inert solvent such as ether, THF, 1,2-dimethoxyethane, or 1,4-dioxane, where THF is preferred at 0° C. to 150° C., where 50° C. is preferred to form the compound of formula XII. The benzyl group in XII is removed according to the procedures described in T. W. Greene and P. G. M. Wuts, Protective Groups in Organic Synthesis, John Wiley & Sons, 1999. The procedure using hydrogen gas at 50 psi and 10% palladium on carbon as a catalyst and ethanol/concentrated HCl as the solvent at ambient temperature is preferred providing a compound of formula II where m=1 and n=1.

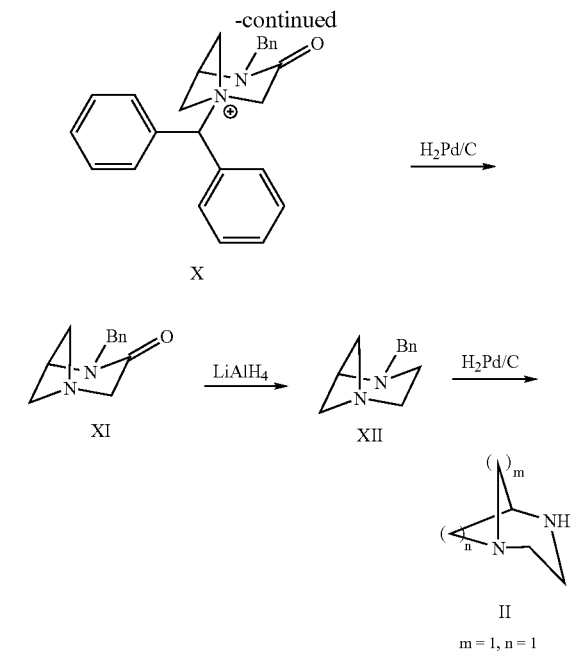

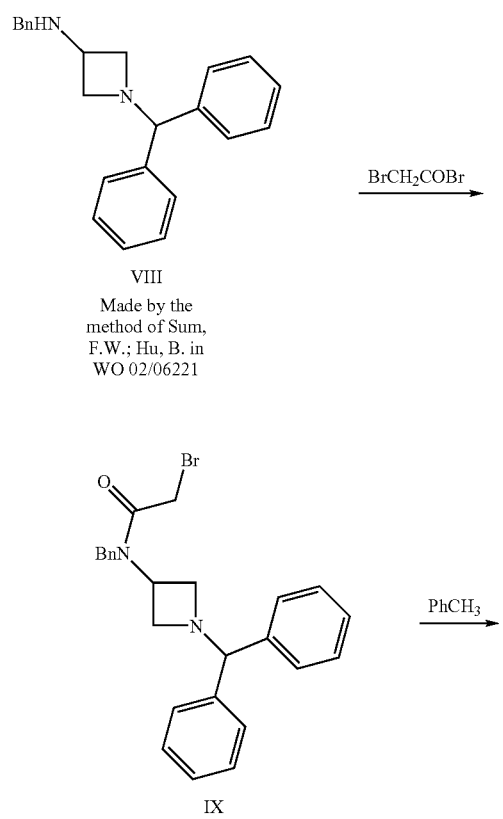

A compound of formula II where m=1 and n=2 can be prepared by three different procedures. The first method is according to the procedures described by Strum; et al. *J. Med. Chem.*, 1977, 20, 1333-7. The second and third methods are shown in the following Schemes IV and V. Referring to Scheme IV, azabicyclo[2.2.1]alkan-3-one of formula XIII was prepared according to the procedures described by Saunders; et al., *J. Chem. Soc., Chem. Commun.*, 1988, 1618-9. The compound of formula XIII is converted to the corresponding oxime compound of formula XIV upon treatment with hydroxylamine hydrochloride in the presence of a base such as, but not limited to, lithium or sodium or potassium or cesium carbonate, lithium or sodium or potassium hydroxide, sodium or potassium acetate, sodium or potassium t-butoxide, where sodium carbonate is preferred. This reaction is carried out in an inert reaction solvent such as methanol, ethanol, n- or i-propanol, dimethylsulfoxide, dimethylformamide, dimethoxyethane, where methanol is preferred from 0° C. to 150° C., where 70° C. is preferred. The oxime compound XIV undergoes ring expansion via the Beckmann Rearrangment upon treatment with a suitable acid such as, but not limited to, sulfuric acid, nitric acid, hydrochloric acid, acetic acid, phosphoric acid, formic acid, or polyphosphoric acid at 0° C. to 150° C. Alternatively, the oxime XIV can be treated with phosphorus tri-chloride or phosphorus tri-bromide in an inert reaction solvent such as dichloromethane, 1,2-dichloroethane or chloroform. Preferably, the oxime XIV was dissolved in concentrated sulfuric acid and heated to 100° C. to form the lactam compound of formula XV. Lactam XV is reduced with a suitable reducing agent such as, but not limited to, lithium aluminum hydride, borane, alane, or di-isobutyl aluminum hydride, where lithium aluminum hydride is preferred in an inert solvent such as ether, THF, 1,2-dimethoxyethane, or 1,4-dioxane, where THF is preferred at 0° C. to 150° C., where 50° C. is preferred to form the compound of formula II where m=1 and n=2.

Scheme IV

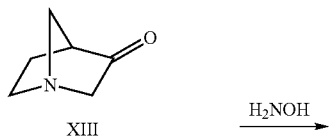

XIII
Made by the procedure of Saunders, et al. *J. Chem. Soc., Chem. Commun.* 1988, 1618–9.

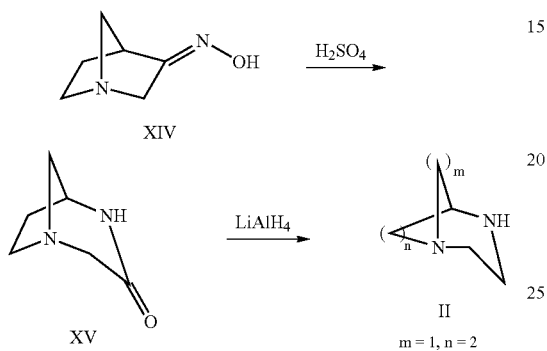

The third method for preparing a compound of formula II where m=1 and n=2 is described in Scheme V. Referring to Scheme V, the commercially available piperazine compound of formula XVI is protected as the benzyl amine compound XVII according to the procedures described in T. W. Greene and P. G. M. Wuts, Protective Groups in Organic Synthesis, John Wiley & Sons, 1999, where the procedure using benzyl bromide in ethanol at 60° C. is preferred. A compound of formula XVII is reduced using a suitable reducing agent such as, but not limited to, lithium aluminum hydride, borane, alane, or di-isobutyl aluminum hydride, where lithium aluminum hydride is preferred in an inert solvent such as ether, THF, 1,2-dimethoxyethane, hexanes or 1,4-dioxane where THF is preferred at 0° C. to 100° C., where 0° C. to ambient temperature is preferred to form 2-(piperazinyl)-ethanol compound of formula XVIII. Reaction of a compound of formula XVIII with diethyl azodicarboxylate or diisopropyl azodicarboxylate, where diethyl azodicarboxylate is preferred and a phosphine reagent such as but not limited to dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)-biphenyl, 2-(di-tert-butylphosphino)-biphenyl, 2-dicyclohexylphosphino-2'-(N,N-dimethylamino)biphenyl, 2-di-tert-butylphosphino-2'-(N,N-dimethylamino)biphenyl or polymer supported triphenylphosphine; more preferably triphenylphosphine in an inert reaction solvent such as water, methanol, ethanol, isopropanol, acetonitrile, methylene chloride, chloroform, 1,2-dichloroethane, tetrahydrofuran, diethylether, dioxane, 1,2-dimethoxyethane, benzene, toluene, dimethylformamide, or dimethylsulfoxide, more preferably tetrahydrofuran at 0° C. to 100° C., where 20° C. is preferred produces a diazabicycle compound of formula XIX. Alternative methods for this conversion would include converting the primary alcohol functional group of XVII in to a good leaving group such as, but not limited to, Cl, Br, I, tosylate, mesylate followed by cyclization to the desired bicycle XIX under thermal conditions with or without the addition of a base. Removal of the benzyl protecting group in XIX to afford 1,4-diazabicyclo[3.2.1]octane (a compound of formula II, where m=1 and n=2) is accomplished by a variety of conditions as detailed in in T. W. Greene and P. G. M. Wuts, Protective Groups in Organic Synthesis, John Wiley & Sons, 1999, with the preferred conditions being hydrogenation at 50 psi $H_2$, using palladium on carbon as a catalyst and EtOH and HCl as solvent at room temperature.

Scheme V

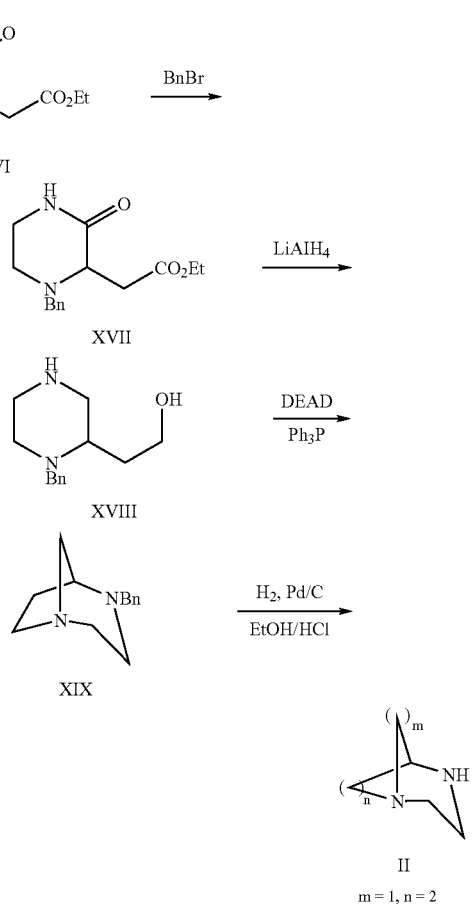

A compound of formula II where m=1 and n=3 is prepared according to two methods. The first method is according to the procedures described by Rubstov, M. V.; et al. *Zh. Obshch. Khim.* 1964, 61, 9481. The second method is according to the procedures described in Scheme VI. Referring to Scheme VI, 3-(4-benzyl-piperazin-2-yl)-propionic acid methyl ester (XX) was made according to the procedure of Van den Branden, S.; et al. *J. Chem. Soc. Perkin Trans.* 1 1992, 1035. A compound of formula XX was reduced by reaction with lithium aluminum hydride, RED-AL, or alane, in an inert reaction solvent such as ether, THF, 1,4-dioxane, 1,2-dimethoxyethane, hexane, benzene or toluene at 0° C. to the solvent reflux temperature with lithium aluminum hydride in THF at 0° C. to ambient temperature being preferred to give a compound of formula XXI. The compound of formula XXI was protected as the trifluoroacetamide giving a compound of formula XXII according to the procedures described in T. W. Greene and P. G. M. Wuts, Protective Groups in Organic Synthesis, John Wiley & Sons, 1999, where the procedure using trifluoroacetic anhydride and pyridine with dichloromethane as a solvent from 0° C. to ambient temperature is preferred. The benzyl group in XXII is removed according to the procedures described in T. W. Greene and P. G. M. Wuts, Protective Groups in Organic Synthesis, John Wiley & Sons, 1999, where the procedure using hydrogen gas at 50 psi and 10% palladium on carbon as a catalyst and ethanol/concentrated HCl as the solvent at ambient temperature is preferred to give a compound of formula XXIII. Treatment of a compound of formula XXIII with diethyl azodicarboxylate or diisopropyl azodicarboxylate, where diethyl azodicarboxylate is preferred and a phosphine reagent such as but not limited to dicyclohexylphenylphosphine, tricyclohexylphosphine, tri-tert-butylphosphine, tri-isopropylphosphine, tri-n-propylphosphine, tri-isobutylphosphine, tri-n-butylphosphine, tri-o-tolylphosphine, triphenylphosphine, 2-(dicyclohexylphosphino)-biphenyl, 2-(di-tert-butylphosphino)-biphenyl, 2-dicyclohexylphosphino-2'-(N,N-dimethylamino)biphenyl, 2-di-tert-butylphosphino-2'-(N,N-dimethylamino)biphenyl or polymer supported triphenylphosphine; more preferably triphenylphosphine in an inert reaction solvent such as water, methanol, ethanol, isopropanol, acetonitrile, methylene chloride, chloroform, 1,2-dichloroethane, tetrahydrofuran, diethylether, 1,4-dioxane, 1,2-dimethoxyethane, benzene, toluene, dimethylformamide, or dimethylsulfoxide, more preferably tetrahydrofuran at 0° C. to 100° C., where 20° C. is preferred produces a diazabicycle compound of formula XXIV. Alternative methods for this conversion would include converting the primary alcohol functional group of XXIII in to a good leaving group such as, but not limited to, Cl, Br, I, tosylate, mesylate followed by cyclization to the desired bicycle XXIV under thermal conditions with or without the addition of a base. The trifluoroacetamide group in XXIV is removed according to the procedures described in T. W. Greene and P. G. M. Wuts, Protective Groups in Organic Synthesis, John Wiley & Sons, 1999, where the procedure using sodium carbonate in a methanol/water reaction solvent at 60° C. is preferred to form a compound of formula II, where m 1 and n=3.

Scheme VI

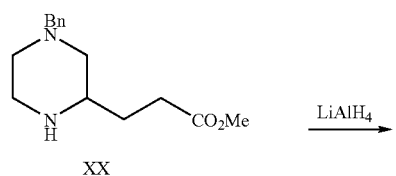

Van den Branden, S.; et al *J. Chem. Soc. Perkin Trans 1* 1992, 1035

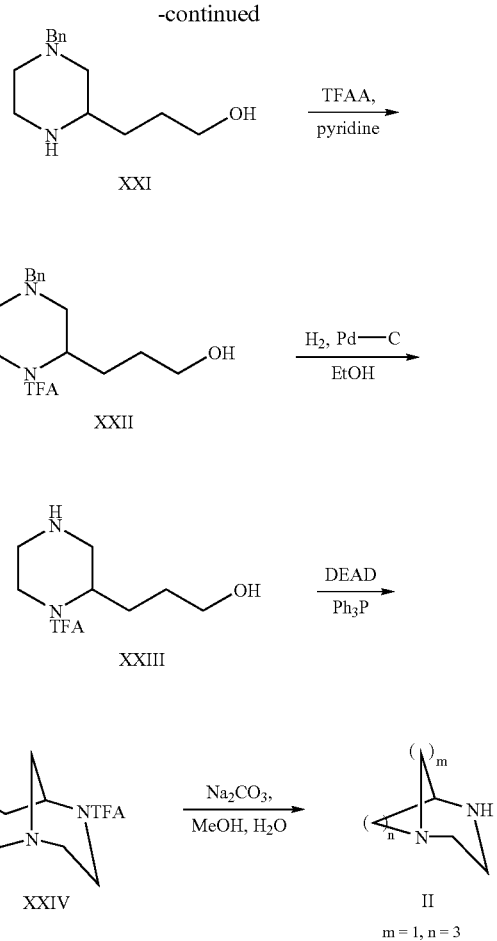

m = 1, n = 3

A compound of formula II where m=2 and n=3 is prepared according to the procedures outlined in Scheme VII. Referring to Scheme VII, 1-aza-bicyclo[3.2.2]nonan-6-one (XXV), made by the procedure of Lowe; et al. *Bioorg. & Med. Chem. Lett.* 1993, 3(5), 921-924, was converted to the oxime compound of formula XXVI upon treatment with hydroxylamine hydrochloride in the presence of a base such as, but not limited to, lithium or sodium or potassium or cesium carbonate, lithium or sodium or potassium hydroxide, sodium or potassium acetate, sodium or potassium t-butoxide, where sodium carbonate is preferred. This reaction is carried out in an inert reaction solvent such as methanol, ethanol, n- or i-propanol, dimethylsulfoxide, dimethylformamide, 1,2-dimethoxyethane, where methanol is preferred from 0° C. to 150° C., where 70° C. is preferred. The oxime compound XXVI undergoes ring expansion via the Beckmann Rearrangment upon treatment with a suitable acid such as, but not limited to, sulfuric acid, nitric acid, hydrochloric acid, acetic acid, phosphoric acid, formic acid, or polyphosphoric acid at 0° C. to 150° C. Alternatively, the oxime XXVI can be treated with phosphorus tri-chloride or phosphorus tri-bromide in an inert reaction solvent such as dichloromethane, 1,2-dichloroethane or chloroform. Preferably, the oxime XXVI was dissolved in concentrated sulfuric acid and heated to 100° C. to form the lactam compound of formula XXVII. Lactam XXVII is reduced with a suitable reducing agent such as, but not limited to, lithium aluminum hydride, borane, alane, or di-isobutyl aluminum hydride, where lithium aluminum hydride is preferred in an inert solvent such as ether, THF, 1,2-dimethoxyethane, or 1,4-dioxane, where THF is preferred at 0° C. to 150° C., where 50° C. is preferred to form the compound of formula II where m=2 and n=3.

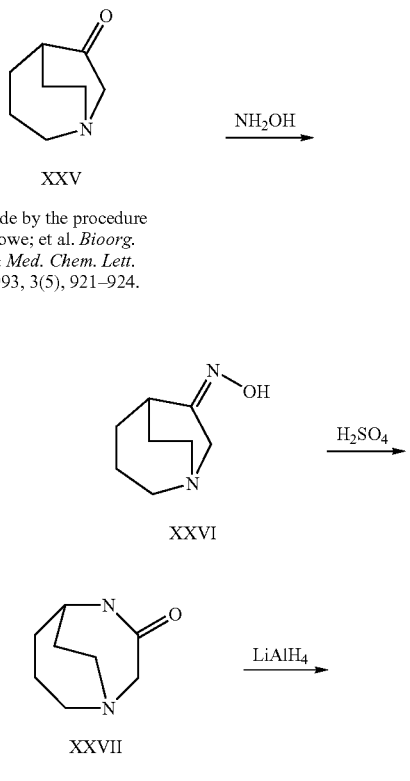

Scheme VII

XXV

Made by the procedure Lowe; et al. *Bioorg. & Med. Chem. Lett.* 1993, 3(5), 921–924.

XXVI

XXVII

II
m = 2, n = 3

A compound of formula II where m=3 and n=3 is prepared according to the procedures outlined in Scheme VIII. 5-Oxo-azocane-1-carboxylic acid methyl ester (XXVIII) was made by the procedure of Miyano; et al. *Heterocycles* 1986, 24(8), 2121-2125, and was reacted with tosylmethylisocyanide (tosmic) in the presence of a base such as, but not limited to, lithium or sodium or potassium or cesium carbonate, lithium or sodium or potassium hydroxide, sodium or potassium methoxide, sodium or potassium ethoxide, sodium or potassium acetate, sodium or potassium t-butoxide, where potassium t-butoxide is preferred, in an inert reaction solvent such as, but not limited to, ether, tetrhydrofuran, 1,2-dimethoxyethane, and 1,4-dioxane, more preferable 1,2-dimethoxyethane at ambient temperature to the solvent reflux temperature where 60° C. is preferred to give a compound of formula XXIX. The compound of formula XXIX was refluxed with aqueous acid such as, but not limited to, sulfuric acid, nitric acid, hydrochloric acid, acetic acid, phosphoric acid, or formic acid, more preferably hydrochloric acid and then with methanol or ethanol, preferably methanol, saturated with gaseous HCl to give a compound of formula XXX. The resulting amine compound of formula XXX was refluxed with methyl bromoacetate and a base such as, but not limited to, triethy-lamine, diisopropylethylamine, pyridine, 2,6-lutidine, and 1,8-diazabicyclo[5.4.0]undec-7-ene; more preferable triethylamine, in an inert reaction solvent such as dichlormethane, 1,2-dichloroethane, 1,4-dioxane, toluene or tetrahydrofuran, more preferable dichloromethane at ambient temperature to the reflux temperature of the solvent, more preferable ambient temperature, to give a compound of formula XXXI. The diester compound of formula XXXI was reacted with a strong base such as, but not limited to, sodium or potassium methoxide, sodium or potassium ethoxide, or sodium or potassium t-butoxide; more preferable potassium ethoxide in a mixture of alcohol and hydrocarbon solvent; more preferable ethanol/toluene at ambient temperature up to the reflux point of the solvent; more preferably the reflux temperature followed by treatment with refluxing aqueous hydrochloric or sulfuric acid to give a compound of formula XXXII. The compound of formula XXXII was converted to the oxime compound of formula XXXIII upon treatment with hydroxylamine hydrochloride in the presence of a base such as, but not limited to, lithium or sodium or potassium or cesium carbonate, lithium or sodium or potassium hydroxide, sodium or potassium acetate, sodium or potassium t-butoxide, where sodium carbonate is preferred. This reaction is carried out in an inert reaction solvent such as methanol, ethanol, n- or i-propanol, dimethylsulfoxide, dimethylformamide, 1,2-dimethoxyethane, where methanol is preferred from 0° C. to 150° C., where 70° C. is preferred. The oxime compound XXXIII undergoes ring expansion via the Beckmann Rearrangment upon treatment with a suitable acid such as, but not limited to, sulfuric acid, nitric acid, hydrochloric acid, acetic acid, phosphoric acid, formic acid, or polyphosphoric acid at 0° C. to 150° C. Alternatively, the oxime XXXIII can be treated with phosphorus tri-chloride or phosphorus tri-bromide in an inert reaction solvent such as dichloromethane, 1,2-dichloroethane or chloroform. Preferably, the oxime XXXIII was dissolved in concentrated sulfuric acid and heated to 100° C. to form the lactam compound of formula XXXIV. Lactam XXXIV is reduced with a suitable reducing agent such as, but not limited to, lithium aluminum hydride, borane, alane, or di-isobutyl aluminum hydride, where lithium aluminum hydride is preferred in an inert solvent such as ether, THF, 1,2-dimethoxyethane, or 1,4-dioxane, where THF is preferred at 0° C. to 150° C., where 50° C. is preferred to form the compound of formula II where m=3 and n=3.

Schem VIII

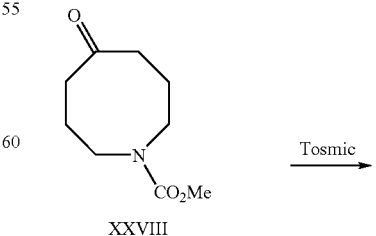

XXVIII

Made by the procedure of Miyano; et al. *Heterocycles* 1986, 24(8), 2121–2125.

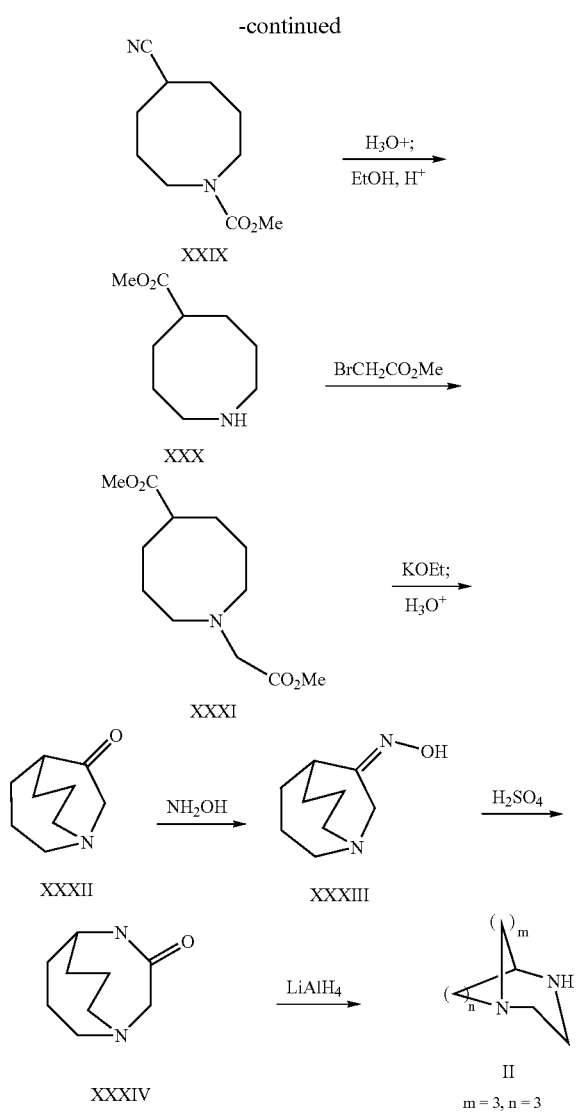

Compounds of formula III, namely substituted phenyl, pyridine, pyrazine, pyrimidine and pyridazine compounds, can be purchased or prepared by methods well known to those of skill in the art.

Compounds of formula IIIA wherein one of the groups defined by A, B, D, E, or F is substituted with a $(C_6-C_{11})$aryl or 5-12 membered hetero aryl group, $R^6$ as defined above, are prepared according to the methods detailed in Scheme IX. Referring to Scheme IX, the synthesis is initiated from a compound of formula III wherein one of the groups defined by A, B, D, E, or F above contains a C-Z group. The functional group Z is defined as a group with the ability to undergo oxidative addition, such as but not limited to Cl, Br, I, OTf, by an organometallic reagent. These compounds of formula III are commercially available or are prepared according to procedures described in the literature and can be prepared easily by one skilled in the art of organic synthesis. Preferred organometallic reagents contain metal such as palladium, nickel or copper with palladium being the most preferred. Referring to Scheme IX, treatment of a compound of the formula III wherein Z is chloro, bromo, iodo or triflate (OTf) with bis (pinacolato)diboron and a palladium catalyst such as palladium (0) tetrakis(triphenylphosphine), palladium (II) acetate, allyl palladium chloride dimer, tris(dibenzylideneacetone)dipalladium (0), tris(dibenzylidene-acetone)dipalladium (0) chloroform adduct, palladium (II) chloride or dichloro[1,1'-bis(diphenylphosphino)ferrocene]palladium (II) dichloromethane adduct, preferably dichloro[1,1'-bis(diphenylphosphino)-ferrocene]palladium (II) dichloromethane adduct, in the presence or absence of a phosphine ligand such as 1,1'-bis(diphenylphosphino)ferrocene, triphenylphosphine, tri-o-tolylphosphine, tri-tert-butylphosphine, 1,2-bis (diphenylphosphino)ethane, 1,3-bis(diphenylphosphino)-propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably 1,1'-bis(diphenylphosphino)ferrocene, and in the presence or absence of a base such as potassium acetate, sodium acetate, cesium acetate, sodium carbonate, lithium carbonate, potassium carbonate, cesium carbonate or cesium fluoride, preferably potassium acetate, yields a compound of the formula XXXV wherein the Z group has been replaced with M, wherein M=borane pinacol ester. Generally, this reaction is carried out in a reaction inert solvent such as 1,4-dioxane, acetonitrile, methyl sulfoxide, tetrahydrofuran, ethanol, methanol, 2-propanol, toluene, preferably methyl sulfoxide, at a temperature from about from 0° C. to about 200° C., preferably from about 80° C. to about 120° C.

Other methods of converting a compound of the formula III with the Z group mentioned above into a compound of the formula XXXV wherein the Z group is replaced with M, wherein M is boronic acid, boronic acid ester or trialkylstannane, are known in the art. For instance, treatment of a compound of the formula III, wherein Z is Br or I, with an alkyl lithium reagent such as, but not limited to n-butyl lithium, sec butyl lithium or tert-butyl lithium, in a solvent such as diethyl ether, tetrahydrofuran, dimethoxyethane, hexane, toluene, dioxane or a similar reaction inert solvent, at a temperature from about −100° C. to about 25° C. affords the corresponding compound of the formula XXXV wherein Z is Li. Treatment of a solution of this material with a suitable boronic ester such as trimethoxyborane, triethoxyborane or triisopropylborane, followed by a standard aqueous work-up with acid will afford the corresponding compound of the formula XXXV wherein M is boronic acid.

Alternatively, treating a mixture of a compound of the formula III wherein Z is Br or I and a boronic ester with an alkyl lithium reagent, as described above, followed by a standard aqueous work-up with acid will afford the corresponding compound of formula XXXV wherein M is boronic acid. Alternatively, treating a compound of the formula III wherein Z is Br or I with an alkyl lithium reagent such as, but not limited to n-butyl lithium, sec butyl lithium or tert-butyl lithium, in a solvent such as diethyl ether, tetrahydrofuran, dimethoxyethane, hexane, toluene, dioxane or a similar reaction inert solvent, at a temperature from about −100° C. to about 25° C. will afford the corresponding compound of the formula XXXV wherein M is Li. Treatment of a solution of this material with a suitable trialkylstannyl halide such as, but not limited to trimethylstannyl chloride or bromide or tributylstannyl chloride or bromide, followed by a standard aqueous work-up will afford the corresponding compound of the formula XXXV wherein M is trimethyl or tributylstannane.

Treatment of a compound of the formula XXXV wherein M is a boronic acid, boronic ester, or trialkylstannane group, with an aryl or heteroaryl chloride, aryl or heteroaryl bromide, aryl or heteroaryl iodide, or aryl or heteroaryl triflate of the formula XXXVI, preferably an aryl or heteroaryl bromide, with a palladium catalyst such as palladium (0) tetrakis(triphenylphosphine), palladium (II) acetate, allyl palladium chloride dimer, tris(dibenzylideneacetone)dipalladium (0), tris(dibenzylideneacetone)dipalladium (0) chloroform adduct, palladium (II) chloride or dichloro[1,1'-bis (diphenylphosphino)ferrocene]palladium (II) dichloromethane adduct, preferably palladium (0) tetrakis(triphenylphosphine), in the presence or absence of a phosphine ligand such as 1,1'-bis(diphenylphosphino)ferrocene, triphenylphosphine, tri-o-tolylphosphine, tri-tert-butylphosphine, 1,2-bis(diphenylphosphino)ethane, 1,3-bis(diphenylphosphino)propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably triphenylphosphine, and in the presence or absence of a base such as potassium phosphate, potassium acetate, sodium acetate, cesium acetate, sodium carbonate, lithium carbonate, potassium carbonate, cesium fluoride or cesium carbonate, preferably potassium phosphate, affords a compound of formula IIIA. This reaction is typically carried out in a reaction inert solvent such as 1,4-dioxane, acetonitrile, methyl sulfoxide, tetrahydrofuran, ethanol, methanol, 2-propanol, or toluene, preferably 1,4-dioxane, in the presence or absence of from about 1%-about 10% water, preferably about 5% water, at a temperature from about 0° C. to about 200° C., preferably from about 60° C. to about 100° C.

Alternatively, referring to Scheme IX, a compound of the formula III can be reacted with a compound of the formula XXXVII, wherein M is a boronic acid, boronic acid ester, borane pinacol ester or trialkylstannane group, preferably an aryl or heteroaryl boronic acid or boronic acid ester, with a palladium catalyst such as palladium (0) tetrakis(triphenylphosphine), palladium (II) acetate, allyl palladium chloride dimer, tris(dibenzylideneacetone)dipalladium (0), tris(dibenzylideneacetone)dipalladium (0) chloroform adduct, palladium (II) chloride or dichloro[1,1'-bis (diphenylphosphino)ferrocene]palladium (II) dichloromethane adduct, preferably palladium (0) tetrakis(triphenylphosphine), in the presence or absence of a phosphine ligand such as 1,1'-bis(diphenylphosphino)ferrocene, triphenylphosphine, tri-o-tolylphosphine, tri-tert-butylphosphine, 1,2-bis(diphenylphosphino)ethane, 1,3-bis(diphenylphosphino)-propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably triphenylphosphine, and in the presence or absence of a base such as potassium phosphate, potassium acetate, sodium acetate, cesium acetate, sodium carbonate, lithium carbonate, potassium carbonate, cesium fluoride or cesium carbonate, preferably sodium carbonate, affording a compound of formula IIIA. This reaction is typically carried out in a reaction inert solvent such as 1,4-dioxane, acetonitrile, methyl sulfoxide, tetrahydrofuran, ethanol, methanol, 2-propanol, or toluene, preferably ethanol, in the presence or absence of from 0%-10% water, preferably about 0% water, at a temperature from about 0° C. to about 200° C., preferably from about 60° C. to about 100° C.

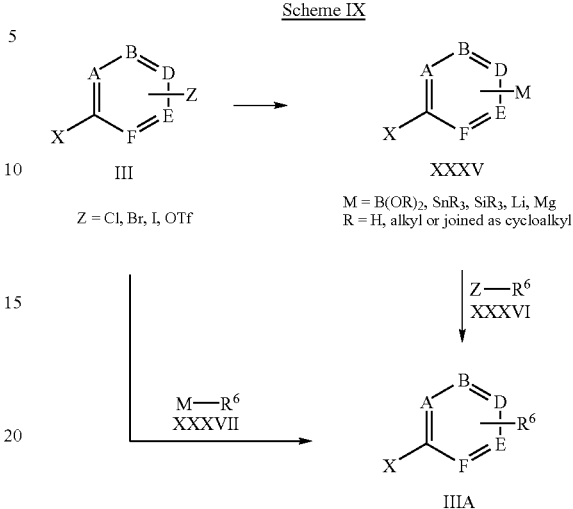

Scheme IX $M = B(OR)_2, SnR_3, SiR_3, Li, Mg$
$R = H$, alkyl or joined as cycloalkyl Compounds of formula IA wherein one of the groups defined by A, B, D, E, or F is substituted with a $(C_6-C_{11})$aryl or 5-12 membered hetero aryl group, $R^6$ as defined above, are prepared according to the methods detailed in Scheme I using a compound of formula IIIA as described above. Alternatively, compounds of formula IA can be prepared according to the methods detailed in Scheme X. Referring to Scheme X, the synthesis is initiated from a compound of formula I wherein one of the groups defined by A, B, D, E, or F above contains a C-Z group. The functional group Z is defined as a group with the ability to undergo oxidative addition, such as but not limited, to Cl, Br, I, OTf, by an organometallic reagent. These compounds of formula I are prepared according to procedures described in Scheme I. Preferred organometallic reagents contain metal such as palladium, nickel or copper with palladium being the most preferred. Referring to Scheme X, treatment of a compound of the formula I wherein Z is chloro, bromo, iodo or triflate (OTf) with bis(pinacolato)diboron and a palladium catalyst such as palladium (0) tetrakis(triphenylphosphine), palladium (II) acetate, allyl palladium chloride dimer, tris(dibenzylideneacetone)dipalladium (0), tris(dibenzylidene-acetone)dipalladium (0) chloroform adduct, palladium (II) chloride or dichloro[1,1'-bis(diphenylphosphino)ferrocene]palladium (II) dichloromethane adduct, preferably dichloro[1,1'-bis(diphenylphosphino)-ferrocene]palladium (II) dichloromethane adduct, in the presence or absence of a phosphine ligand such as 1,1'-bis(diphenylphosphino)ferrocene, triphenylphosphine, tri-o-tolylphosphine, tri-tert-butylphosphine, 1,2-bis(diphenylphosphino)ethane, 1,3-bis(diphenylphosphino)propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably 1,1'-bis(diphenylphosphino)ferrocene, and in the presence or absence of a base such as potassium acetate, sodium acetate, cesium acetate, sodium carbonate, lithium carbonate, potassium carbonate, cesium carbonate or cesium fluoride, preferably potassium acetate, yields a compound of the formula XXXVIII wherein the Z group has been replaced with M, wherein M=borane pinacol ester. Generally, this reaction is carried out in a reaction inert solvent such as 1,4-dioxane, acetonitrile, methyl sulfoxide, tetrahydrofuran, ethanol, methanol, 2-propanol, toluene, preferably methyl sulfoxide, at a temperature from about from 0° C. to about 200° C., preferably from about 80° C. to about 120° C.

Other methods of converting a compound of the formula I with the Z group mentioned above into a compound of the formula XXXVIII wherein the Z group is replaced with M, wherein M is boronic acid, boronic acid ester or trialkylstannane, are known in the art. For instance, treatment of a compound of the formula I, wherein Z is Br or I, with an alkyl lithium reagent such as, but not limited to n-butyl lithium, sec butyl lithium or tert-butyl lithium, in a solvent such as diethyl ether, tetrahydrofuran, dimethoxyethane, hexane, toluene, dioxane or a similar reaction inert solvent, at a temperature from about −100° C. to about 25° C. affords the corresponding compound of the formula XXXVIII wherein Z is Li. Treatment of a solution of this material with a suitable boronic ester such as trimethoxyborane, triethoxyborane or triisopropylborane, followed by a standard aqueous work-up with acid will afford the corresponding compound of the formula XXXVIII wherein M is boronic acid.

Alternatively, treating a mixture of a compound of the formula I wherein Z is Br or I and a boronic ester with an alkyl lithium reagent, as described above, followed by a standard aqueous work-up with acid will afford the corresponding compound of formula XXXVIII wherein M is boronic acid. Alternatively, treating a compound of the formula I wherein Z is Br or I with an alkyl lithium reagent such as, but not limited to n-butyl lithium, sec butyl lithium or tert-butyl lithium, in a solvent such as diethyl ether, tetrahydrofuran, dimethoxyethane, hexane, toluene, dioxane or a similar reaction inert solvent, at a temperature from about −100° C. to about 25° C. will afford the corresponding compound of the formula XXXVIII wherein M is Li. Treatment of a solution of this material with a suitable trialkylstannyl halide such as, but not limited to trimethylstannyl chloride or bromide or tributylstannyl chloride or bromide, followed by a standard aqueous work-up will afford the corresponding compound of the formula XXXVIII wherein M is trimethyl or tributylstannane.

Treatment of a compound of the formula XXXVIII wherein M is a boronic acid, boronic ester, or trialkylstannane group, with an aryl or heteroaryl chloride, aryl or heteroaryl bromide, aryl or heteroaryl iodide, or aryl or heteroaryl triflate of the formula XXXIX, preferably an aryl or heteroaryl bromide, with a palladium catalyst such as palladium (0) tetrakis(triphenylphosphine), palladium (II) acetate, allyl palladium chloride dimer, tris(dibenzylideneacetone)dipalladium (0), tris(dibenzylideneacetone)dipalladium (0) chloroform adduct, palladium (II) chloride or dichloro(1,1'-bis(diphenylphosphino)ferrocene]palladium (II) dichloromethane adduct, preferably palladium (0) tetrakis(triphenylphosphine), in the presence or absence of a phosphine ligand such as 1,1'-bis(diphenylphosphino)ferrocene, triphenylphosphine, tri-o-tolylphosphine, tri-tert-butylphosphine, 1,2-bis(diphenylphosphino)ethane, 1,3-bis(diphenylphosphino)-propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably triphenylphosphine, and in the presence or absence of a base such as potassium phosphate, potassium acetate, sodium acetate, cesium acetate, sodium carbonate, lithium carbonate, potassium carbonate, cesium fluoride or cesium carbonate, preferably sodium carbonate, affords a compound of formula IA. This reaction is typically carried out in a reaction inert solvent such as 1,4-dioxane, acetonitrile, methyl sulfoxide, tetrahydrofuran, ethanol, methanol, 2-propanol, or toluene, preferably ethanol, in the presence or absence of from about 0%-about 10% water, preferably about 0% water, at a temperature from about 0° C. to about 200° C., preferably from about 60° C. to about 100° C.

Alternatively, referring to Scheme X, a compound of the formula I can be reacted with a compound of the formula XL, wherein M is a boronic acid, boronic acid ester, borane pinacol ester or trialkylstannane group, preferably an aryl or heteroaryl boronic acid or boronic acid ester, with a palladium catalyst such as palladium (0) tetrakis(triphenylphosphine), palladium (II) acetate, allyl palladium chloride dimer, tris(dibenzylideneacetone)dipalladium (0), tris(dibenzylideneacetone)dipalladium (0) chloroform adduct, palladium (II) chloride or dichloro[1,1'-bis(diphenylphosphino)ferrocene]palladium (II) dichloromethane adduct, preferably palladium (0) tetrakis(triphenylphosphine), in the presence or absence of a phosphine ligand such as 1,1'-bis(diphenylphosphino)ferrocene, triphenylphosphine, tri-o-tolylphosphine, tri-tert-butylphosphine, 1,2-bis(diphenylphosphino)ethane, 1,3-bis(diphenylphosphino)-propane, BINAP, 2-biphenyl dicyclohexylphosphine, 2-biphenyl-di-tert-butylphosphine, 2-(N,N-dimethylamino)-2'-di-tert-butylphosphino-biphenyl or 2-(N,N-dimethylamino)-2'-dicyclohexylphosphinobiphenyl, preferably triphenylphosphine, and in the presence or absence of a base such as potassium phosphate, potassium acetate, sodium acetate, cesium acetate, sodium carbonate, lithium carbonate, potassium carbonate, cesium fluoride or cesium carbonate, preferably sodium carbonate, affording a compound of formula IA. This reaction is typically carried out in a reaction inert solvent such as 1,4-dioxane, acetonitrile, methyl sulfoxide, tetrahydrofuran, ethanol, methanol, 2-propanol, or toluene, preferably ethanol, in the presence or absence of from 0%-10% water, preferably about 0% water, at a temperature from about 0° C. to about 200° C., preferably from about 60° C. to about 100° C.

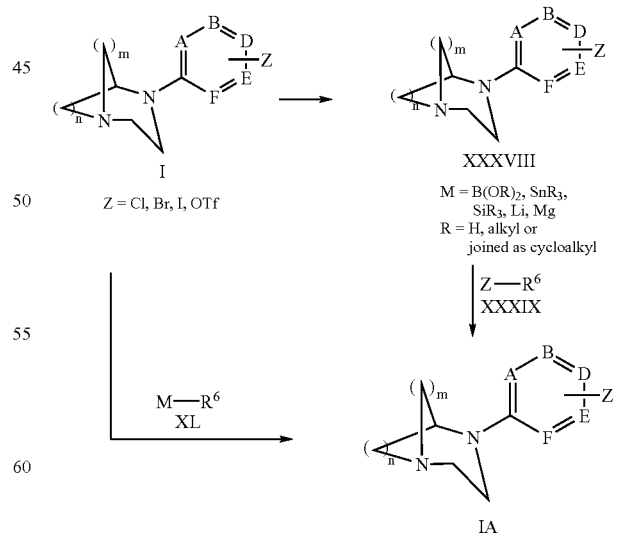

Scheme X

Isolation and purification of the products can be accomplished by standard procedures that are known to a chemist of ordinary skill. In each of the reactions discussed above, or illustrated in Schemes above, pressure is not critical unless otherwise indicated. Pressures from about 0.5 atmospheres to about 5 atmospheres are generally acceptable, with ambient pressure, i.e., about 1 atmosphere, being preferred as a matter of convenience.

The compounds of the formula I and their pharmaceutically acceptable salts (hereafter "the active compounds") can be administered via either the oral, transdermal (e.g., through the use of a patch), intranasal, sublingual, rectal, parenteral or topical routes. Transdermal and oral administration are preferred. These compounds are, most desirably, administered in dosages ranging from about 0.25 mg up to about 1500 mg per day, preferably from about 0.25 to about 300 mg per day in single or divided doses, although variations will necessarily occur depending upon the weight and condition of the subject being treated and the particular route of administration chosen. However, a dosage level that is in the range of about 0.01 mg to about 10 mg per kg of body weight per day is most desirably employed. Variations may nevertheless occur depending upon the weight and condition of the persons being treated and their individual responses to said medicament, as well as on the type of pharmaceutical formulation chosen and the time period and interval during which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds can be administered alone or in combination with pharmaceutically acceptable carriers or diluents by any of the several routes previously indicated. More particularly, the active compounds can be administered in a wide variety of different dosage forms, e.g., they may be combined with various pharmaceutically acceptable inert carriers in the form of tablets, capsules, transdermal patches, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. In addition, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc can be used for tabletting purposes. Solid compositions of a similar type may also be employed as fillers in gelatin capsules; preferred materials in this connection also include lactose or milk sugar, as well as high molecular weight polyethylene glycols. When aqueous suspensions and/or elixirs are desired for oral administration the active ingredient may be combined with various sweetening or flavoring agents, coloring matter and, if so desired, emulsifying and/or suspending agents, together with such diluents as water, ethanol, propylene glycol, glycerin and various combinations thereof.

For parenteral administration, a solution of an active compound in either sesame or peanut oil or in aqueous propylene glycol can be employed. The aqueous solutions should be suitably buffered (preferably pH greater than 8), if necessary, and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the active compounds topically and this can be done by way of creams, a patch, jellies, gels, pastes, ointments and the like, in accordance with standard pharmaceutical practice.

The effectiveness of the active compounds in suppressing nicotine binding to specific receptor sites can be determined by the following procedure, which is a modification of the methods of Lippiello, P. M. and Fernandes, K. G. (in "The Binding of L-[$^3$H]Nicotine To A Single Class of High-Affinity Sites in Rat Brain Membranes", *Molecular Pharm.*, 29, 448-54, (1986)) and Anderson, D. J. and Arneric, S. P. (in "Nicotinic Receptor Binding of $^3$H-Cytisine, $^3$H-Nicotine and $^3$H-Methylcarmbamylcholine In Rat Brain", *European J. Pharm.*, 253, 261-67 (1994)). Male Sprague-Dawley rats (200-300 g) from Charles River were housed in groups in hanging stainless steel wire cages and were maintained on a 12 hour light/dark cycle (7 a.m.-7 p.m. light period). They received standard Purina Rat Chow and water ad libitum. The rats were killed by decapitation. Brains were removed immediately following decapitation. Membranes were prepared from brain tissue according to the methods of Lippiello and Fernandez (*Molec. Pharmacol.*, 29, 448-454, (1986)) with some modifications. Whole brains were removed, rinsed with ice-cold buffer, and homogenized at 0° in 10 volumes of buffer (w/v) using a Brinkmann Polytron™ (Brinkmann Instruments Inc., Westbury, N.Y.), setting 6, for 30 seconds. The buffer consisted of 50 mM Tris HCl at a pH of 7.5 at room temperature. The homogenate was sedimented by centrifugation (10 minutes; 50,000×g; 0° to 4° C.). The supernatant was poured off and the membranes were gently resuspended with the Polytron and centrifuged again (10 minutes; 50,000×g; 0° C. to 4° C.). After the second centrifugation, the membranes were resuspended in assay buffer at a concentration of 1.0 g/100 mL. The composition of the standard assay buffer was 50 mM Tris HCl, 120 mM NaCl, 5 mM KCl, 2 mM MgCl$_2$, 2 mM CaCl$_2$ and had a pH of 7.4 at room temperature.

Routine assays were performed in borosilicate glass test tubes. The assay mixture typically consisted of 0.9 mg of membrane protein in a final incubation volume of 1.0 mL. Three sets of tubes were prepared wherein the tubes in each set contained 50 μL of vehicle, blank, or test compound solution, respectively. To each tube was added 200 μL of [$^3$H]-nicotine in assay buffer followed by 750 μL of the membrane suspension. The final concentration of nicotine in each tube was 0.9 nM. The final concentration of cytisine in the blank was 1 μM. The vehicle consisted of deionized water containing 30 μL of 1 N acetic acid per 50 mL of water. The test compounds and cytisine were dissolved in vehicle. Assays were initiated by vortexing after addition of the membrane suspension to the tube. The samples were incubated at 0° to 4° C. in an iced shaking water bath. Incubations were terminated by rapid filtration under vacuum through Whatman GF/B™ glass fiber filters (Brandel Biomedical Research & Development Laboratories, Inc., Gaithersburg, Md.) using a Brandel™ multi-manifold tissue harvester (Brandel Biomedical Research & Development Laboratories, Inc., Gaithersburg, Md.). Following the initial filtration of the assay mixture, filters were washed two times with ice-cold assay buffer (5 ml each). The filters were then placed in counting vials and mixed vigorously with 20 ml of Ready Safe™ (Beckman, Fullerton, Calif.) before quantification of radioactivity. Samples were counted in a LKB Wallac Rackbeta™ liquid scintillation counter (Wallac Inc., Gaithersburg, Md.) at 40-50% efficiency. All determinations were in triplicate.

Calculations: Specific binding (C) to the membrane is the difference between total binding in the samples containing vehicle only and membrane (A) and non-specific binding in the samples containing the membrane and cytisine (B), i.e., Specific binding=$(C)=(A)-(B)$.

Specific binding in the presence of the test compound (E) is the difference between the total binding in the presence of the test compound (D) and non-specific binding (B), i.e., $(E)=(D)-(B)$.

% Inhibition=$(1-((E)/(C))$times 100.

The compounds of the invention that were tested in the above assay exhibited $IC_{50}$ values of less than 100 µM.

[$^{125}$I]-Bungarotoxin binding to nicotinic receptors in $GH_4Cl$ cells: Membrane preparations were made for nicotinic receptors expressed in $GH_4Cl$ cell line. Briefly, one gram of cells by wet weight were homogenized with a polytron in 25 mls of buffer containing 20 mM Hepes, 118 mM NaCl, 4.5 mM KCl, 2.5 mM $CaCl_2$, 1.2 mM $MgSO_4$, pH 7.5. The homogenate was centrifuged at 40,000×g for 10 min at 4° C., the resulting pellet was homogenized and centrifuged again as described above. The final pellet was resuspended in 20 mls of the same buffer. Radioligand binding was carried out with [$^{125}$I] alpha-bungarotoxin from New England Nuclear, specific activity about 16 uCi/ug, used at 0.4 nM final concentration in a 96 well microtiter plate. The plates were incubated at 37° C. for 2 hours with 25 µl drugs or vehicle for total binding, 100 µl [$^{125}$I] Bungarotoxin and 125 µl tissue preparation. Nonspecific binding was determined in the presence of methyllycaconitine at 1 µM final concentration. The reaction was terminated by filtration using 0.5% Polyethylene imine treated Whatman GF/B™ glass fiberfilters (Brandel Biomedical Research & Development Laboratories, Inc., Gaithersburg, Md.) on a Skatron cell harvester (Molecular Devices Corporation, Sunnyvale, Calif.) with ice-cold buffer, filters were dried overnight, and counted on a Beta plate counter using Betaplate Scint. (Wallac Inc., Gaithersburg, Md.). Data are expressed as IC50's (concentration that inhibits 50% of the specific binding) or as an apparent Ki, IC50/1((+))[L]/KD. [L]=ligand concentration, KD=affinity constant for [$^{125}$I] ligand determined in separate experiment.

The compounds of the invention that were tested in the above assay exhibited $IC_{50}$ values of less than 10 µM.

[$^{125}$I]-Bungarotoxin binding to alpha1 nicotinic receptors in Torpedo electroplax membranes: Frozen Torpedo electroplax membranes (100 µl) were resuspended in 213 mls of buffer containing 20 mM Hepes, 118 mM NaCl, 4.5 mM KCl, 2.5 mM $CaCl_2$, 1.2 mM $MgSO_4$, pH 7.5 with 2 mg/ml BSA. Radioligand binding was carried out with [$^{125}$I] alpha-bungarotoxin from New England Nuclear, specific activity about 16 uCi/ug, used at 0.4 nM final concentration in a 96 well microtiter plate. The plates were incubated at 37° C. for 3 hours with 25 µl drugs or vehicle for total binding, 100 µl [$^{125}$I] Bungarotoxin and 125 µl tissue preparation. Nonspecific binding was determined in the presence of alpha-bungarotoxin at 1 µM final concentration. The reaction was terminated by filtration using 0.5% Polyethylene imine treated GF/B filters on a Brandel cell harvester with ice-cold buffer, filters were dried overnight, and counted on a Beta plate counter using Betaplate Scint. Data are expressed as IC50's (concentration that inhibits 50% of the specific binding) or as an apparent Ki, IC50/1+[L]/KD. [L]=ligand concentration, KD=affinity constant for [125] ligand determined in separate experiment.

The compounds of the invention that were tested in the above assay exhibited $IC_{50}$ values of less than 100 µM.

EXAMPLES

The following examples illustrate the methods and compounds of the present invention. It will be understood, however, that the invention is not limited to the specific Examples. In the examples, commercial reagents were used without further purification. Purification by chromatography was done on prepacked silica columns from Biotage (Dyax Corp, Biotage Division, Charlottesville, Va.). Melting points (mp) were obtained using a Mettler Toledo FP62 melting point apparatus (Mettler-Toledo, Inc., Worthington, Ohio) with a temperature ramp rate of 10° C./min and are uncorrected. Proton nuclear magnetic resonance ($^1$H NMR) spectra were recorded in deuterated solvents on a Varian INOVA400 (400 MHz) spectrometer (Varian NMR Systems, Palo Alto, Calif.). Chemical shifts are reported in parts per million (ppm, δ) relative to $Me_4Si$ (δ 0.00). Proton NMR splitting patterns are designated as singlet(s), doublet (d), triplet (t), quartet (q), quintet (quin), sextet (sex), septet (sep), multiplet (m) apparent (ap) and broad (br). Coupling constants are reported in hertz (Hz). Carbon-13 nuclear magnetic resonance ($^{13}$C NMR) spectra were recorded on a Varian INOVA400 (100 MHz). Chemical shifts are reported in ppm (δ) relative to the central line of the 1:1:1 triplet of deuterochloroform (δ 77.00), the center line of deuteromethanol (δ 49.0) or deuterodimethylsulfoxide (δ 39.7). The number of carbon resonance's reported may not match the actual number of carbons in some molecules due to magnetically and chemically equivalent carbons and may exceed the number of actual carbons due to conformational isomers. Mass spectra (MS) were obtained using a Waters ZMD mass spectrometer using flow injection atmospheric pressure chemical ionization (APCI) (Waters Corporation, Milford, Mass). Gas chromatography with mass detection (GCMS) were obtained using a Hewlett Packard HP 6890 series GC system with a HP 5973 mass selective detector and a HP-1 (crosslinked methyl siloxane) column (Agilent Technologies, Wilmington, Del.). HPLC spectra were recorded on a Hewlett Packard 1100 series HPLC system with a Zorbax SB-C8, 5 µm, 4.6×150 mm column (Agilent Technologies, Wilmington, Del.) at 25° C. using gradient elution. Solvent A is water, Solvent B is acetonitrile, Solvent C is 1% trifluoroacetic acid in water. A linear gradient over four minutes was used starting at 80% A, 10% B, 10% C and ending at 0% A, 90% B, 10% C. The eluent remained at 0% A, 90% B, 10% C for three minutes. A linear gradient over one minute was used to return the eluent to 80% A, 10% B, 10% C and it was held at this until the run time equaled ten minutes. Room temperature (RT) refers to 20-25° C.

Example 1

4-(5-Bromo-pyridin-3-yl)-1,4-diaza-bicyclo[3.2.1] octane dihydrochloride

A) (1-Benzyl-3-oxo-piperazin-2-yl)-acetic acid ethyl ester

Benzyl bromide (7.7 mL, 77 mmol) was added to a solution of ethyl-2-piperazine-3-one acetate (13 g, 70 mmol, May-bridge) in ethanol (100 mL). The mixture was heated at 60° C. for 6 hrs. Additional benzyl bromide (0.7 mL, 7 mmol) was added and the mixture was heated at 60° C. for 8 hrs. The solvent was removed in vacuo and the residue was dissolved in a mixture of water (100 mL) and ethyl acetate (100 mL) (note, pH=1.5). Partition and extract with ethyl acetate (3×100 mL). Wash the combined extracts with saturated NaHCO$_3$, dry over Na$_2$SO$_4$, filter and concentrate to a solid. The solid was triturated with hexanes and the remaining solid was collected to yield 11 g (58%) of the title compound: $^1$H NMR (CDCl$_3$, 400 MHz) δ 7.33-7.24 (m, 5H), 6.60 (br s, 1H), 4.23-4.10 (m, 2H), 3.69 (2H, AB, J$_{AB}$=13.3 Hz), 3.50 (br s, 1H), 3.33-3.22 (m, 2H), 3.09-3.04 (m, 1H), 2.98-2.88 (m, 2H), 2.51-2.44 (m, 1H), 1.25 (t, 3H, J=7.3 Hz); APCI MS m/z 277.1 (M+1).

B) 2-(1-Benzyl-piperazin-2-yl)-ethanol

Lithium aluminum hydride (4.6 grams, 120 mmol) was slowly added to a solution of (1-benzyl-3-oxo-piperazin-2-yl)-acetic acid ethyl ester (11 g, 40 mmol) in THF (150 mL) at 0° C. The mixture was allowed to stir for 18 h while warming to RT. The mixture was placed in and ice/water bath and additional lithium aluminum hydride (3.0 g, 80 mmol) was added. The mixture was allowed to stir for 20 h while warming to RT. 1 N NaOH was added until all of the LAH was consumed resulting in a white solid. The mixture was filtered through a pad of celite, washing with additional THF (50 mL). The filtrate was concentrated in vacuo to give 8 g (90%) of the title compound as an oil: APCI MS m/z 221.2 (M+1).

C) 4-Benzyl-1,4-diaza-bicyclo[3.2.1]octane

Diethyl azodicarboxylate (15.8 mL, 100 mmol) was slowly added to a solution of triphenylphosphine (26.2 g, 100 mmol) in THF (200 mL) while maintaining the reaction temperature below 20° C. After stirring this mixture for 30 min at RT, a solution of 2-(1-benzyl-piperazine-2-yl)-ethanol (11 g, 50 mmol) in THF (100 mL) was added while maintaining the reaction temperature below 20° C. The reaction mixture became turbid and the solvent was removed in vacuo after a period of 1 h. The residue was partitioned between water (20 mL) and ethyl acetate (50 mL) and the pH was adjusted to 2 with 6 N HCl. The phases were separated and the aqueous phase was extracted with EtOAc (50 mL) at pH 3.0, 4.5 and 10 (4×). The pH 10 extracts were combined, dried (Na$_2$SO$_4$), filtered and concentrated to an oil. The oil was triturated three times with hot hexanes (100 mL) to remove any remaining triphenylphosphine and triphenylphosphine oxide and the hexanes were decanted. The remaining oil was dried resulting in 7.5 g (74%) of the title compound: APCI MS m/z 203.2 (M+1).

D) 1,4-Diaza-bicyclo[3.2.1]octane dihydrochloride

A mixture of 4-benzyl-1,4-diaza-bicyclo[3.2.1]octane (7.5 g, 37 mmol), 5% palladium on carbon (0.75 g, wet), concentrated HCl (7.5 mL) in EtOH (150 mL) was shaken under hydrogen (50 psi) for a period of 20 h at RT. The product precipitated out of the mixture and water was added in order to dissolve the product. The mixture was filtered through a pad of celite and washed with EtOH. The filtrate was concentrated in vacuo to a solid that was azeotroped with EtOH (3×50 mL). The resulting solid was triturated with hot isopropanol and stirred 18 h at RT. The resulting solid was collected by filtration giving 5.6 g (80%) of the title compound: $^1$H NMR (d6-DMSO, 400 MHz) δ 4.26 (br s, 1H), 3.72 (d, 1H, J=12 Hz), 3.60-3.53 (m, 1H), 3.48-3.35 (m, 7H), 2.33-2.27 (m, 2H); GCMS m/z 112

E) 4-(5-Bromo-pyridin-3-yl)-1,4-diaza-bicyclo[3.2.1]octane dihydrochoride

A solution of NaOMe (0.48 mL, 2.2 mmol, 4.6 M in MeOH) was added to a solution of 1,4-diaza-bicyclo[3.2.1]octane dihydrochloride (0.2 g, 1.1 mmol) in MeOH (15 mL) at 50° C. The solvent was removed in vacuo and the resulting residue was triturated with toluene (5 mL). The toluene solution was added to a flask containing 3,5-dibromopyridine (0.26 g, 1.1 mmol), 2,2'-bis(diphenylphosphino)-1,1'-binaphthyl (0.2 g, 0.33 mmol), tris(dibenzylideneacetone)dipalladium (0) (0.1 g, 0.11 mmol), and NaOtBu (0.15 g, 1.5 mmol) under and atmosphere of nitrogen. The resulting mixture was heated at 80° C. for 20 h. The mixture was cooled to RT, diluted with CHCl$_3$ (10 mL) and washed with water (10 mL). The organic layer was concentrated and purified by chromatography using a gradient elution (20/1 CHCl$_3$/MeOH to 10/1 CHCl$_3$/MeOH) to give 90 mg (30%) of the title compound as its free base. This material was dissolved in EtOH and treated with concentrated HCl (0.2 mL). The solvent was removed in vacuo and the EtOH was added and the solvent was once again removed in vacuo. This procedure was repeated until concentration resulted in a solid (3× total). The resulting solid was triturated with iPrOH and the resulting solid was collected to give 82 mg (22%) of the title compound: (data for free base) $^1$H NMR (CDCl$_3$, 400 MHz) δ 8.13 (d, 1H, J=2.9 Hz), 8.06 (d, 1H, J=2.1 Hz), 7.21-7.19 (m, 1H), 4.20-4.17 (m, 1H), 3.15-3.08 (m, 3H), 3.04-2.80 (m, 4H), 2.66-2.62 (m, 1H), 1.87-1.72 (m, 2H); $^{13}$C NMR (CDCl$_3$, 100 MHz) δ 147.0, 140.5, 136.4, 124.2, 121.1, 59.9, 57.0, 52.9, 50.7, 41.7, 29.9; APCI MS m/z 270.1, 268.1 (M+1).

Example 2

4-(5-Phenyl-pyridin-3-yl)-1,4-diaza-bicyclo[3.2.1]octane dihydrochloride 4-(5-Bromo-pyridin-3-yl)-1,4-diaza-bicyclo[3.2.1]octane dihydrochoride (50 mg, 0.15 mmol) was added to a mixture of phenylboronic acid (25 mg, 0.20 mmol), tetrakis(triphenylphosphine)palladium(0) (7 mg, 0.006 mmol), sodium carbonate (63 mg, 0.60 mmol) in EtOH (5 mL) and water (5 mL). The reaction mixture was placed in an oil bath at 80° C. for 3 h, and then 60° C. for 18 h. The mixture was cooled to RT, diluted with water (10 mL) and extracted with EtOAc (3×15 mL). The combined organic extracts were dried (Na$_2$SO$_4$), filtered and concentrated. The residue was dissolved in EtOH (10 mL) and conc. HCl (0.2 mL) was added. The mixture was concentrated and EtOH (10 mL) was added and the solution was concentrated. This procedure was repeated three times and the resulting solid was triturated in EtOAc. The remaining solids were collected via filtration to give 40 mg (78%) of the title compound: (data for free base) $^1$H NMR (CD$_3$OD, 400 MHz) δ 8.55 (br s, 1H), 8.50 (br s, 1H), 8.33 (br s, 1H), 7.83-7.81 (m, 2H), 7.60-7.53 (m, 3H), 5.12 (br s, 1H), 4.06-4.04 (m, 1H), 3.70-3.59 (m, 5H), 3.54-3.51 (m, 2H), 2.51-2.47 (m, 1H), 2.26-2.23 (m, 1H); APCI MS m/z 266.2 (M+1).

Example 3

4-Pyridin-2-yl-1,4-diaza-bicyclo[3.2.1]octane dihydrochloride

The title compound was prepared by the methods described in Example 1E starting with 2-bromopyridine: (data for free base) $^1$H NMR (CDCl$_3$, 400 MHz) δ 8.14 (dd, 1H, J=5.0, 1.7 Hz), 7.44-7.40 (m, 1H), 6.56 (dd, 1H, J=7.0, 5.0 Hz), 7.51 (d, 1H, J=8.7 Hz), 4.94 (dd, 1H, J=5.8, 3.3 Hz), 3.51-3.47 (m, 1H), 3.07-2.90 (m, 5H), 2.79-2.75 (m, 1H), 2.62-2.58 (m, 1H), 1.91-1.84 (m, 1H), 1.76-1.71 (m, 1H); $^{13}$C (CDCl$_3$, 100 MHz) δ 159.1, 148.2, 137.6, 113.3, 107.4, 60.0, 53.8, 53.2, 50.8, 40.0, 31.1; APCI MS m/z 190.2 (M+1).

Example 4

4-Pyridin-3-yl-1,4-diaza-bicyclo[3.2.1]octane dihydrochloride

The title compound was prepared by the methods described in Example 1E starting with 3-bromopyridine: (data for free base) $^{13}$C NMR (CDCl$_3$, 100 MHz) δ 146.2, 140.3, 138.5, 123.7, 122.2, 60.0, 57.1, 53.0, 50.8, 41.9, 29.4; APCI MS m/z 190.2 (M+1).

Example 5

4-Pyridin-4-yl-1,4-diaza-bicyclo[3.2.1]octane dihydrochloride

The title compound was prepared by the methods described in Example 1E starting with 4-bromopyridine: (data for free base) $^{13}$C NMR (CDCl$_3$, 100 MHz) δ 153.2, 150.3, 108.5, 59.7, 55.0, 53.0, 50.8, 40.6, 30.8; APCI MS m/z 190.2 (M+1).

Example 6

4-(5-Bromo-pyridin-2-yl)-1,4-diaza-bicyclo[3.2.1]octane dihydrochloride

The title compound was prepared by the methods described in Example 1E starting with 2,5-dibromopyridine: (data for free base) $^{13}$C NMR (CDCl$_3$, 100 MHz) δ 157.3, 148.7, 139.9, 108.7, 107.6, 59.8, 53.8, 53.1, 50.8, 40.0, 31.2; APCI MS m/z 270.1, 268.1 (M+1).

Example 7

4-(5-Phenyl-pyridazin-3-yl)-1,4-diaza-bicyclo[3.2.1]octane dihydrochloride

The title compound was prepared by the methods described in Example 1E starting with 3-chloro-5-phenylpyridazine (Rival, Y.; Hoffmann, R.; Didier, B.; Rybaltchenko, V.; Bourguignon, J.-J.; Wermuth, C. G. *J. Med. Chem.* 1998, 41, 311): (data for free base) $^{13}$C NMR (CDCl$_3$, 100 MHz) δ 160.0, 142.5, 140.0, 136.2, 129.8, 129.5, 127.3, 109.6, 59.9, 54.0, 53.2, 50.8, 39.8, 31.5; APCI MS m/z 267.2 (M+1).

Example 8

4-(6-Phenyl-pyridazin-3-yl)-1,4-diaza-bicyclo[3.2.1]octane dihydrochloride

The title compound was prepared by the methods described in Example 1E starting with 3-chloro-6-phenylpyridazine: (data for free base) $^1$H NMR (CDCl$_3$, 400 MHz) δ 8.00 (d, 2H, J=7.1 Hz), 7.66 (d, 1H, J=9.5 Hz), 7.49-7.40 (m, 4H), 6.94 (d, 1H, J=9.5 Hz), 5.11 (dd, 1H, J=5.4, 3.3 Hz), 3.80 (dd, 1H, J=12.9, 5.4 Hz), 3.28-3.04 (m, 5H), 2.94-2.91 (m, 1H), 2.77-2.74 (m, 1H), 2.09-2.01 (m, 1H), 1.94-1.89 (m, 1H); APCI MS m/z 267.1 (M+1).

Example 9

4-Pyrazin-2-yl-1,4-diaza-bicyclo[3.2.1]octane dihydrochloride

The title compound was prepared by the methods described in Example 1E starting with 2-chloropyrazine: (data for free base) $^{13}$C NMR (CDCl$_3$, 100 MHz) δ 142.0, 133.1, 131.4, 59.8, 53.2, 53.0, 50.7, 39.4, 31.4; APCI MS m/z 191.1 (M+1).

Example 10

4-Pyrimidin-5-yl-1,4-diaza-bicyclo[3.2.1]octane dihydrochloride

The title compound was prepared by the methods described in Example 1E starting with 5-bromopyrimidine: (data for free base) $^{13}$C NMR (CDCl$_3$, 100 MHz) δ 149.5, 143.7, 59.8, 56.3, 52.8, 50.7, 41.2, 29.8; APCI MS m/z 191.1 (M+1).

Example 11

4-(5-Chloro-pyridin-3-yl)-1,4-diaza-bicyclo[3.2.1]octane dihydrochloride

The title compound was prepared by the methods described in Example 1E starting with 3,5-dichloropyridine: (data for free base) $^{13}$C NMR (CDCl$_3$, 100 MHz) δ 146.8, 138.3, 136.0, 132.3, 121.4, 59.9, 57.0, 52.9, 50.8, 41.8, 29.9; APCI MS m/z 224.1 (M+1).

Example 12

4-[5-(3-Trifluoromethyl-phenyl)-pyridin-3-yl]-1,4-diaza-bicyclo[3.2.1]octane dihydrochloride

A) 3-Bromo-5-(3-trifluoromethyl-phenyl)-pyridine

A mixture of 3,5-dibromopyridine (1.2 g, 5 mmol), 3-trifluoromethylphenyl boronic acid (0.95 g, 5 mmol), tetrakis(triphenylphosphine)palladium (0) (0.23 g, 0.2 mmol), and sodium carbonate (1.1 g, 10 mmol) in EtOH (10 mL) and water (1 mL) were heated in an oil bath at 70° C. for 3 days. The mixture was cooled to RT and diluted with EtOAc (20 mL) and water (10 mL). The layers were partitioned and the organic layer was dried (Na$_2$SO$_4$), filtered and concentrated. Purification by chromatography (eluting with 10:1 hexanes/EtOAc) resulted in 0.4 g (26%) of the title compound: $^1$H NMR (CDCl$_3$, 400 MHz) δ 8.76 (d, 1H, J=2.1 Hz), 8.71 (d, 1H, J=2.1 Hz), 8.06 (dd, 1H, J=2.1, 2.1 Hz), 7.80 (s, 1H), 7.74-7.61 (m, 3H); APCI MS m/z 304.0, 302.0 (M+1).

B) 4-[5-(3-Trifluoromethyl-phenyl)-pyridin-3-yl]-1, 4-diaza-bicyclo[3.2.1]octane dihydrochloride The title compound was prepared by the methods described in Example 1E starting with 3,5-dichloropyridine: (data for free base) $^{13}$C NMR (CDCl$_3$, 100 MHz) δ 146.2, 139.6, 138.7, 137.9, 135.6, 130.8, 129.7, 124.9, 124.8, 124.3, 124.2, 120.6, 60.1, 57.2, 53.1, 50.8, 42.0, 29.7; APCI MS m/z 344.1 (M+1).

Example 13

4-(3-Bromo-phenyl)-1,4-diaza-bicyclo[3.2.1]octane dihydrochloride

The title compound was prepared by the methods described in Example 1E starting with 1,3-dibromobenzene: (data for free base) $^{13}$C NMR (CDCl$_3$, 100 MHz) δ 151.7, 130.6, 123.6, 121.9, 118.6, 114.3, 60.1, 57.5, 53.1, 50.9, 42.2, 29.6; APCI MS m/z 269.0, 267.0 (M+1).

Example 14

5-(1,4-Diaza-bicyclo[3.2.1]oct-4-yl)-nicotinonitrile dihydrochloride

The title compound was prepared by the methods described in Example 1E starting with 3-bromo-5-cyanopyridine: (data for free base) $^{13}$C NMR (CDCl$_3$, 100 MHz) δ 145.4, 141.5, 141.4, 123.3, 117.4, 109.9, 59.8, 56.6, 52.8, 50.7, 41.5, 30.1; APCI MS m/z 215.1 (M+1).

Example 15

4-(5-Trifluoromethyl-pyridin-3-yl)-1,4-diaza-bicyclo[3.2.1]octane dihydrochloride The title compound was prepared by the methods described in Example 1E starting with 3-chloro-5-trifluoromethylpyridine: (data for free base) $^{13}$C NMR (CDCl$_3$, 100 MHz) δ 145.6, 141.0, 136.0, 135.9, 117.84, 117.81, 59.9, 56.9, 52.9, 50.7, 41.6, 29.9; APCI MS m/z 258.1 (M+1).

Example 16

4-[5-(2-Trifluoromethyl-phenyl)-pyridin-3-yl]-1,4-diaza-bicyclo[3.2.1]octane dihydrochloride A) 3-Bromo-5-(2-trifluoromethyl-phenyl)-pyridine The title compound was prepared by the methods described in Example 12A starting with 2-trifluoromethylphenylboronic acid: $^1$H NMR (CDCl$_3$, 400 MHz) δ 8.70 (d, 1H, J=2.1 Hz), 8.49 (d, 1H, J=1.7 Hz), 7.82-7.77 (m, 2H), 7.63-7.53 (m, 2H), 7.30 (d, 1H, J=7.5 Hz); APCI MS m/z 304.0, 302.0 (M+1).

B) 4-[5-(2-Trifluoromethyl-phenyl)-pyridin-3-yl]-1, 4-diaza-bicyclo[3.2.1]octane Dihydrochloride The title compound was prepared by the methods described in Example 1E starting with 3-bromo-5-(2-trifluoromethyl-phenyl)-pyridine: (data for free base) $^{13}$C NMR (CDCl$_3$, 100 MHz) δ 145.2, 139.9, 138.1, 137.7, 135.6, 132.2, 131.8, 129.0, 128.3, 126.5, 125.5, 122.9, 59.9, 57.1, 53.0, 50.8, 41.9, 29.4; APCI MS m/z 334.2 (M+1).

Example 17

4-[5-(4-Trifluoromethyl-phenyl)-pyridin-3-yl]-1,4-diaza-bicyclo[3.2.1]octane dihydrochloride A) 3-Bromo-5-(4-trifluoromethyl-phenyl)-pyridine The title compound was prepared by the methods described in Example 12A starting with 4-trifluoromethylphenylboronic acid: $^1$H NMR (CDCl$_3$, 400 MHz) δ 8.76 (d, 1H, J=1.7 Hz), 8.71 (d, 1H, J=2.1 Hz), 8.04 (t, 1H, J=2.1 Hz), 7.75 (d, 2H, J=8.3 Hz), 7.67 (d, 2H, J=7.9 Hz); APCI MS m/z 304.0, 302.0 (M+1).

B) 4-[5-(4-Trifluoromethyl-phenyl)-pyridin-3-yl]-1, 4-diaza-bicyclo[3.2.1]octane dihydrochloride The title compound was prepared by the methods described in Example 1E starting with 3-bromo-5-(4-trifluoromethyl-phenyl)-pyridine: (data for free base) $^{13}$C NMR (CDCl$_3$, 100 MHz) δ 146.2, 142.1, 138.7, 138.0, 135.6, 127.8, 126.13, 126.09, 120.7, 60.0, 57.2, 53.0, 50.8, 41.9, 29.6; APCI MS m/z 334.2 (M+1).

Example 18

4-[5-(2-Fluoro-phenyl)-pyridin-3-yl]-1,4-diaza-bicyclo[3.2.1]octane dihydrochloride A) 3-Bromo-5-(2-fluoro-phenyl)-pyridine The title compound was prepared by the methods described in Example 12A starting with 2-fluorophenylboronic acid: $^1$H NMR (CDCl$_3$, 400 MHz) δ 8.73 (d, 1H, J=1.7 Hz), 8.67 (d, 1H, J=2.1 Hz), 7.99 (t, 1H, J=2.1 Hz), 7.48-7.42 (m, 1H), 7.34-7.23 (m, 2H), 7.15-7.10 (m, 1H); APCI MS m/z 252.0, 254.0 (M+1).

B) 4-[5-(2-Fluoro-phenyl)-pyridin-3-yl]-1,4-diaza-bicyclo[3.2.1]octane dihydrochloride The title compound was prepared by the methods described in Example 1E starting with 3-bromo-5-(2-fluoro-phenyl)-pyridine: (data for free base) $^{13}$C NMR (CDCl$_3$, 100 MHz) δ 164.8, 162.1, 146.2, 141.1, 138.7, 137.7, 135.8, 130.8, 130.7, 123.2, 120.6, 115.1, 114.9, 114.5, 114.3, 60.0, 57.2, 53.0, 50.8, 42.0, 29.6; APCI MS m/z 284.3 (M+1).

Example 19

4-[5-(4-Fluoro-phenyl)-pyridin-3-yl]-1,4-diaza-bicyclo[3.2.1]octane dihydrochloride A) 3-Bromo-5-(4-fluoro-phenyl)-pyridine The title compound was prepared by the methods described in Example 12A starting with 4-fluorophenylboronic acid: $^1$H NMR (CDCl$_3$, 400 MHz) δ 8.70 (d, 1H, J=1.7 Hz), 8.64 (d, 1H, J=2.5 Hz), 7.97 (t, 1H, J=2.1 Hz), 7.54-7.46 (m, 2H), 7.20-7.14 (m, 2H); APCI MS m/z 252.0, 254.0 (M+1).

B) 4-[5-(4-Fluoro-phenyl)-pyridin-3-yl]-1,4-diaza-bicyclo[3.2.1]octane dihydrochloride The title compound was prepared by the methods described in Example 1E starting with 3-bromo-5-(4-fluorophenyl)-pyridine: (data for free base) $^{13}$C NMR (CDCl$_3$, 100 MHz) δ 164.2, 161.9, 146.1, 138.8, 137.2, 136.1, 134.6, 129.2, 129.1, 120.6, 116.2, 116.0, 60.1, 57.3, 53.0, 50.8, 42.0, 29.6; APCI MS m/z 284.3 (M+1).

Example 20

3-(1,4-Diaza-bicyclo[3.2.1]oct-4-yl)-quinoline dihydrochloride

The title compound was prepared by the methods described in Example 1E starting with 3-bromoquinoline: (data for free base) $^{13}$C NMR (CDCl$_3$, 100 MHz) δ 145.0, 143.9, 142.8, 129.1, 129.0, 127.2, 126.7, 126.4, 116.7, 60.2, 58.1, 53.0, 50.9, 42.3, 29.0; APCI MS m/z 240.2 (M+1).

Example 21

4-(3-Trifluoromethyl-pyridin-2-yl)-1,4-diaza-bicyclo[3.2.1]octane dihydrochloride The title compound was prepared by the methods described in Example 1E starting with 2-bromo-3-trifluoromethyl-pyridine: (data for free base) $^{13}$C NMR (CDCl$_3$, 100 MHz) δ 158.0, 150.8, 137.82, 137.77, 125.8, 123.0, 115.8, 60.3, 60.0, 53.5, 51.1, 42.9, 30.1; APCI MS m/z 258.2 (M+1).

Example 22

4-(6-Methoxy-pyridin-2-yl)-1,4-diaza-bicyclo[3.2.1]octane dihydrochloride

The title compound was prepared by the methods described in Example 1E starting with 2-bromo-6-methoxy-pyridine: (data for free base) $^{13}$C NMR (CDCl$_3$, 100 MHz) δ 163.2, 157.8, 140.3, 98.6, 98.2, 59.9, 53.8, 53.3, 53.2, 50.7, 40.1, 31.0; APCI MS m/z 220.2 (M+1).

Example 23

4-[5-(2-Methoxy-phenyl)-pyridin-3-yl]-1,4-diaza-bicyclo[3.2.1]octane dihydrochloride A) 3-Bromo-5-(2-methoxy-phenyl)-pyridine The title compound was prepared by the methods described in Example 12A starting with 2-methoxyphenyl-boronic acid: $^1$H NMR (CDCl$_3$, 400 MHz) δ 8.68 (d, 1H, J=1.7 Hz), 8.60 (d, 1H, J=2.5 Hz), 8.02 (t, 1H, J=2.1 Hz), 7.41-7.37 (m, 1H), 7.31-7.28 (m, 1H), 7.07-6.99 (m, 2H), 3.83 (s, 3H); APCI MS m/z 266.1, 264.1 (M+1).

B) 4-[5-(2-Methoxy-phenyl)-pyridin-3-yl]-1,4-diaza-bicyclo[3.2.1]octane dihydrochloride The title compound was prepared by the methods described in Example 1E starting with 3-bromo-5-(2-methoxy-phenyl)-pyridine: (data for free base) $^{13}$C NMR (CDCl$_3$, 100 MHz) δ 156.8, 145.6, 141.2, 136.8, 134.3, 130.9, 129.6, 127.8, 123.7, 121.2, 111.5, 60.1, 57.3, 55.8, 53.1, 50.9, 42.1, 29.4; APCI MS m/z 296.2 (M+1).

Example 24

4-[5-(3-Methoxy-phenyl)-pyridin-3-yl]-1,4-diaza-bicyclo[3.2.1]octane dihydrochloride A) 3-Bromo-5-(3-methoxy-phenyl)-pyridine The title compound was prepared by the methods described in Example 12A starting with 3-methoxyphenyl-boronic acid: $^1$H NMR (CDCl$_3$, 400 MHz) δ 8.74 (d, 1H, J=1.7 Hz), 8.68 (d, 1H, J=2.1 Hz), 8.01 (t, 1H, J=2.1 Hz), 7.39 (t, 1H, J=7.9 Hz), 7.14-7.13 (m, 1H), 7.12-7.11 (m, 1H), 7.06-6.95 (m, 1H), 3.86 (s, 3H); APCI MS m/z 266.1, 264.1 (M+1).

B) 4-[5-(3-Methoxy-phenyl)-pyridin-3-yl]-1,4-diaza-bicyclo[3.2.1]octane dihydrochloride The title compound was prepared by the methods described in Example 1E starting with 3-bromo-5-(2-methoxy-phenyl)-pyridine: (data for free base) $^{13}$C NMR (CDCl$_3$, 100 MHz) δ 160.2, 146.1, 140.3, 139.1, 137.4, 137.0, 130.2, 120.9, 120.0, 113.4, 60.1, 57.3, 55.6, 53.0, 50.8, 42.0, 29.5; APCI MS m/z 296.2 (M+1).

Example 25

4-(5-o-Tolyl-pyridin-3-yl)-1,4-diaza-bicyclo[3.2.1]octane dihydrochloride

A) 3-Bromo-5-o-tolyl-pyridine

The title compound was prepared by the methods described in Example 12A starting with o-tolyl-boronic acid: $^1$H NMR (CDCl$_3$, 400 MHz) δ 8.66 (d, 1H, J=2.1 Hz), 8.51 (d, 1H, J=1.7 Hz), 7.82 (t, 1H, J=2.1 Hz), 7.35-7.26 (m, 3H), 7.20-7.18 (m, 1H), 2.28 (s, 3H); APCI MS m/z 250.1, 248.1 (M+1).

B) 4-(5-o-Tolyl-pyridin-3-yl)-1,4-diaza-bicyclo[3.2.1]octane dihydrochloride

The title compound was prepared by the methods described in Example 1E starting with 3-bromo-5-o-tolyl-pyridine: (data for free base) $^{13}$C NMR (CDCl$_3$, 100 MHz) δ 145.7, 140.5, 138.8, 137.6, 136.9, 135.9, 130.7, 130.0, 128.2, 126.2, 123.0, 60.1, 57.2, 53.1, 50.8, 42.1, 29.5, 20.6; APCI MS m/z 280.3 (M+1).

Example 26

5-(1.4-Diaza-bicyclo[3.2.1]oct-4-yl)-nicotinic acid ethyl ester dihydrochloride

The title compound was prepared by the methods described in Example 1E starting with 5-bromo-nicotinic acid ethyl ester: (data for free base) $^{13}$C NMR (CDCl$_3$, 100 MHz) δ 166.2, 145.8, 141.8, 140.9, 126.4, 122.4, 61.6, 60.0, 57.1, 53.0, 50.8, 41.8, 29.7, 14.5; APCI MS m/z 262.2 (M+1).

Example 27

4-(5-Chloro-pyridin-2-yl)-1,4-diaza-bicyclo[3.2.1]octane dihydrochloride

The title compound was prepared by the methods described in Example 1E starting with 2,5-dichloropyridine:

(data for free base) $^{13}$C NMR (CDCl$_3$, 100 MHz) δ 146.5, 137.4, 108.1, 59.8, 54.0, 53.0, 50.7, 40.1, 31.0; APCI MS m/z 224.1 (M+1).

Example 28

4-(6-Methyl-pyridin-3-yl)-1,4-diaza-bicyclo[3.2.1]octane dihydrochloride

The title compound was prepared by the methods described in Example 1E starting with 2-methyl-5-bromopyridine: (data for free base) $^{13}$C NMR (CDCl$_3$, 100 MHz) δ 137.9, 123.8, 123.3, 60.0, 57.7, 52.9, 50.8, 42.1, 28.8, 23.5; APCI MS m/z204.2 (M+1).

Example 29

4-[5-(3-Trifluoromethyl-phenyl)-pyridin-2-yl]-1,4-diaza-bicyclo[3.2.1]octane dihydrochloride The title compound was prepared by the methods described in Example 2 starting with 3-trifluoromethylphenylboronic acid: (data for the free base) $^{13}$C NMR (CDCl$_3$, 100 MHz) δ 158.1, 146.6, 139.5, 136.3, 132.2, 129.6, 129.5, 125.2, 123.6, 123.0, 107.2, 59.8, 54.0, 53.0, 50.7, 39.9, 31.1; APCI MS m/z 334.2 (M+1).

Example 30

4-[5-(4-Chloro-phenyl)-pyridin-2-yl]-1,4-diaza-bicyclo[3.2.1]octane dihydrochloride The title compound was prepared by the methods described in Example 2 starting with 4-chlorophenylboronic acid: (data for the free base) $^{13}$C NMR (CDCl$_3$, 100 MHz) δ 146.3, 137.2, 136.2, 133.1, 132.2, 129.3, 129.0, 127.6, 125.2, 107.2, 59.8, 54.0, 53.0, 50.7, 40.0, 31.1; APCI MS m/z300.2 (M+1).

Example 31

4-(5-o-Tolyl-pyridin-2-yl)-1,4-diaza-bicyclo[3.2.1]octane dihydrochloride

The title compound was prepared by the methods described in Example 2 starting with 2-methylphenylboronic acid: (data for the free base) $^{13}$C NMR (CDCl$_3$, 100 MHz) δ 157.7, 148.1, 138.8, 138.6, 136.0, 130.7, 130.1, 127.5, 127.1, 126.2, 106.6, 59.9, 53.9, 53.2, 50.8, 40.1, 31.1, 20.8; APCI MS m/z280.3 (M+1).

Example 32

4-[5-(3-Chloro-phenyl)-pyridin-2-yl]-1,4-diaza-bicyclo[3.2.1]octane dihydrochloride The title compound was prepared by the methods described in Example 2 starting with 3-chlorophenylboronic acid: (data for the free base) $^{13}$C NMR (CDCl$_3$, 100 MHz) δ 158.2, 146.4, 140.4, 136.3, 135.0, 130.4, 126.9, 126.4, 125.0, 124.4, 107.2, 59.8, 53.8, 53.0, 50.7, 39.9, 31.1; APCI MS m/z 300.2 (M+1).

Example 33

4-[5-(3-Fluoro-phenyl)-pyridin-2-yl]-1,4-diaza-bicyclo[3.2.1]octane dihydrochloride The title compound was prepared by the methods described in Example 2 starting with 3-fluorophenylboronic acid: (data for the free base) $^{13}$C NMR (CDCl$_3$, 100 MHz) δ 164.7, 158.3, 146.4, 140.84, 140.77, 136.2, 130.64, 130.56, 125.0, 121.9, 113.8, 113.6, 113.2, 113.0, 107.1, 59.8, 53.8, 53.1, 50.7, 40.0, 31.2; APCI MS m/z284.2 (M+1).

Example 34

4-[5-(4-Chloro-phenyl)-pyridin-3-yl]-1,4-diaza-bicyclo[3.2.1]octane dihydrochloride A) 3-Bromo-5-(4-chloro-phenyl)-pyridine The title compound was prepared by the methods described in Example 12A starting with 4-chlorophenylboronic acid: $^1$H NMR (CDCl$_3$, 400 MHz) δ 8.72 (d, 1H, J=2.1 Hz), 8.66 (d, 1H, J=2.1 Hz), 8.00 (t, 1H, J=2.1 Hz), 7.51-7.44 (m, 4H); APCI MS m/z 270.0, 268.0 (M+1).

B) 4-[5-(4-Chloro-phenyl)-pyridin-3-yl]-1,4-diaza-bicyclo[3.2.1]octane Dihydrochloride The title compound was prepared by the methods described in Example 1E starting with 3-bromo-5-(4-chlorophenyl)-pyridine: (data for free base) $^{13}$C NMR (CDCl$_3$, 100 MHz) δ 146.0, 138.8, 137.5, 137.1, 135.8, 134.4, 129.4, 128.7, 120.6, 60.0, 57.3, 53.0, 50.8, 41.9, 29.5; APCI MS m/z 300.2 (M+1).

Example 35

4-[5-(2,4-Dichloro-phenyl)-pyridin-3-yl]-1,4-diaza-bicyclo[3.2.1]octane dihydrochloride A) 3-Bromo-5-(2,4-dichloro-phenyl)-pyridine The title compound was prepared by the methods described in Example 12A starting with 2,4-dichlorophenylboronic acid: $^1$H NMR (CDCl$_3$, 400 MHz) δ 8.70, (d, 1H, J=2.5 Hz), 8.57 (d, 1H, J=1.7 Hz), 7.92 (t, 1H, J=2.1 Hz), 7.53 (d, 1H, J=2.1 Hz), 7.35 (dd, 1H, J=8.3, 2.1 Hz), 7.26 (d, 1H, J=8.3 Hz); APCI MS m/z 308.0, 306.0, 304.0, 302.0 (M+1).

B) 4-[5-(2,4-Dichloro-phenyl)-pyridin-3-yl]-1,4-diaza-bicyclo[3.2.1]octane dihydrochloride The title compound was prepared by the methods described in Example 1E starting with 3-bromo-5-(2,4-dichloro-phenyl)-pyridine: (data for free base) $^{13}$C NMR (CDCl$_3$, 100 MHz) δ 145.3, 140.4, 137.8, 136.2, 135.0, 134.2, 133.8, 132.2, 130.2, 127.6, 123.2, 59.9, 57.2, 52.9, 50.7, 41.9, 29.4; APCI MS m/z 336.2, 334.1 (M+1).

Example 36

4-[5-(3-chloro-phenyl)-pyridin-3-yl]-1,4-diaza-bicyclo[3.2.1]octane dihydrochloride A) 3-Bromo-5-(3-chloro-phenyl)-pyridine The title compound was prepared by the methods described in Example 12A starting with 3-chlorophenylboronic acid: $^1$H NMR (CDCl$_3$, 400 MHz) δ 8.73, (d, 1H, J=2.1 Hz), 8.68 (d, 1H, J=2.5 Hz), 8.00 (t, 1H, J=2.1 Hz), 7.54 (t, 1H, J=1.7 Hz), 7.45-7.41 (m, 3H); APCI MS m/z 270.0, 268.0 (M+1).

B) 4-[5-(3-Chloro-phenyl)-pyridin-3-yl]-1,4-diazabicyclo[3.2.1]octane dihydrochloride The title compound was prepared by the methods described in Example 1E starting with 3-bromo-5-(3-chlorophenyl)-pyridine: (data for free base) $^{13}$C NMR (CDCl$_3$, 100 MHz) δ 146.1, 140.5, 138.8, 137.7, 135.7, 135.1, 130.4, 128.3, 127.6, 125.7, 120.7, 60.0, 57.3, 52.9, 50.8, 41.9, 29.5; APCI MS m/z 302.2, 300.2 (M+1).

Example 37

4-(5-D-Tolyl-pyridin-3-yl)-1,4-diaza-bicyclo[3.2.1]octane dihydrochloride

A) 3-Bromo-5-(D-tolyl)-pyridine

The title compound was prepared by the methods described in Example 12A starting with p-tolylboronic acid: $^1$H NMR (CDCl$_3$, 400 MHz) δ 8.72 (d, 1H, J=2.1 Hz), 8.60 (d, 1H, J=2.1 Hz), 7.96 (t, 1H, J=2.1 Hz), 7.42 (d, 2H, J=8.3 Hz), 7.26 (d, 2H, J=7.9 Hz), 2.39 (s, 3H); APCI MS m/z 250.1, 248.1 (M+1).

B) 4-[5-(p-Tolyl-pyridin-3-yl]-1,4-diaza-bicyclo[3.2.1]octane Dihydrochloride

The title compound was prepared by the methods described in Example 1E starting with 3-bromo-5-(p-tolyl)-pyridine: (data for free base) $^{13}$C NMR (CDCl$_3$, 100 MHz) δ 146.1, 139.0, 138.1, 137.0, 136.9, 135.7, 129.9, 127.3, 120.7, 60.1, 57.3, 53.1, 50.8, 42.0, 29.5, 21.4; APCI MS m/z 280.3 (M+1).

Example 38

4-[5-(4-Methoxy-phenyl)-pyridin-3-yl]-1,4-diazabicyclo[3.2.1]octane dihydrochloride A) 3-Bromo-5-(4-methoxy-phenyl)-pyridine The title compound was prepared by the methods described in Example 12A starting with 4-methoxyphenylboronic acid: $^1$H NMR (CDCl$_3$, 400 MHz) δ 8.72 (d, 1H, J=2.1 Hz), 8.60 (d, 1H, J=2.1 Hz), 8.00 (t, 1H, J=2.1 Hz), 7.50 (d, 2H, J=8.7 Hz), 7.01 (d, 2H, J=8.7 Hz), 3.86 (s, 3H); APCI MS m/z 266.1, 264.1 (M+1).

B) 4-[5-(4-Methoxy-phenyl)-pyridin-3-yl]-1,4-diazabicyclo[3.2.1]octane dihydrochloride The title compound was prepared by the methods described in Example 1E starting with 3-bromo-5-(4-methoxy-phenyl)-pyridine: (data for free base) $^{13}$C NMR (CDCl$_3$, 100 MHz) δ 159.9, 146.1, 138.9, 136.8, 136.6, 131.0, 128.5, 120.5, 114.6, 60.1, 57.3, 55.6, 53.0, 50.8, 42.0, 29.5; APCI MS m/z 296.3 (M+1).

Example 39

4-(5-Methoxy-pyridin-3-yl)-1,4-diaza-bicyclo[3.2.1]octane dihydrochloride

The title compound was prepared by the methods described in Example 1E starting with 3-bromo-5-methoxy-pyridine: (data for free base) $^{13}$C NMR (CDCl$_3$, 100 MHz) δ 156.4, 147.0, 131.5, 127.1, 108.3, 59.9, 57.4, 55.8, 52.9, 50.7, 41.9, 29.4; APCI MS m/z 220.3 (M+1).

Example 40

5-(1,4-Diaza-bicyclo[3.2.1]oct-4-yl)-[3.4']bipyridinyl dihydrochloride

A) 5-Bromo-[3,4']bipyridinyl

The title compound was prepared by the methods described in Example 12A starting with pyridine-4-boronic acid: $^1$H NMR (CDCl$_3$, 400 MHz) δ 8.80 (d, 1H, J=2.1 Hz), 8.75-8.73 (m, 3H), 8.07 (t, 1H, J=2.1 Hz), 7.52-7.50 (m, 2H), 2.71 (br s, 1H); APCI MS m/z 237.1, 235.1 (M+1).

B) 5-(1,4-Diaza-bicyclo[3.2.1]oct-4-yl)-[3.4']bipyridinyl dihydrochloride

The title compound was prepared by the methods described in Example 1E starting with 5-bromo-[3,4']bipyridinyl: (data for free base) $^{13}$C NMR (CDCl$_3$, 100 MHz) δ 150.6, 146.2, 146.1, 138.7, 138.4, 134.1, 122.0, 120.2, 60.0, 57.2, 52.9, 50.8, 41.8, 29.6; APCI MS m/z 267.3 (M+1).

Example 41

4-(2-Methyl-5-trifluoromethyl-pyridin-3-yl)-1,4-diaza-bicyclo[3.2.1]octane dihydrochloride The title compound was prepared by the methods described in Example 1E starting with 3-chloro-2-methyl-5-trifluoromethyl-pyridine: (data for free base) $^{13}$C NMR (CDCl$_3$, 100 MHz) δ 158.0, 146.2, 139.0, 138.9, 125.3, 124.7, 124.4, 122.1, 122.0, 60.7, 59.8, 53.1, 51.1, 43.2, 28.0, 22.5; APCI MS m/z 272.3 (M+1).

What is claimed is:

1. A compound of formula I

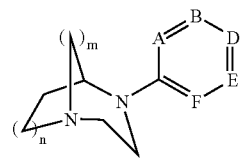

I wherein:
A=CR$^1$ or N,
B=CR$^2$ or N,
D=CR$^3$ or N,
E=CR$^4$ or N and
F=CR$^5$ or N;

and the maximum number of nitrogen atoms amongst A, B, D, E, and F is two;

where m=1 and n=2;

where each $R^1$, $R^2$, $R^3$, $R^4$ and $R^5$ is independently selected from F, Cl, Br, I, nitro, cyano, $CF_3$, —$NR^6R^7$, —$NR^6C(=O)R^7$, —$NR^6C(=O)NR^7R^8$, —$NR^6C(=O)OR^7$, —$OR^6$, —$OC(=O)R^6$, —$OC(=O)OR^6$, —$OC(=O)NR^6R^7$, —$OC(=O)SR^6$, —$C(=O)OR^6$, —$C(=O)R^6$, —$C(=O)NR^6R^7$, —$SR^6$, —$S(=O)R^6$, and a substituent from the definition of $R^6$;

each $R^6$, $R^7$, and $R^8$ is independently selected from H, straight chain or branched ($C_1$-$C_8$)alkyl, straight chain or branched ($C_2$-$C_8$)alkenyl, straight chain or branched ($C_2$-$C_8$)alkynyl, ($C_3$-$C_8$)cycloalkyl, ($C_4$-$C_8$)cycloalkenyl, 3-8 membered heterocycloalkyl, ($C_5$-$C_{11}$)bicycloalkyl, ($C_7$-$C_{11}$)bicycloalkenyl, 5-11 membered heterobicycloalkyl, 5-11 membered heterobicycloalkenyl, ($C_6$-$C_{11}$)aryl, and 5-12 membered heteroaryl; wherein each $R^6$, $R^7$, and $R^8$ is optionally substituted with from one to six substituents, independently selected from F, Cl, Br, I, nitro, cyano, $CF_3$, —$NR^9R^{10}$, —$NR^9C(=O)R^{10}$, —$NR^9C(=O)NR^{10}OR^{11}$, —$NR^9C(=O)OR^{10}$, —$NR^9S(=O)_2R^{10}$, —$NR^9S(=O)_2NR^{10}R^{11}$, —$OR^9$, —$OC(=O)R^9$, —$OC(=O)OR^9$, —$OC(=O)NR^9R^{10}$, —$OC(=O)SR^9$, —$C(=O)OR^9$, —$C(=O)R^9$, —$C(=O)NR^9R^{10}$, —$SR^9$, —$S(=O)R^9$, —$S(=O)_2R^9$, —$S(=O)_2NR^9R^{10}$ and $R^9$;

or $R^1$ and $R^2$, or $R^2$ and $R^3$, or $R^3$ and $R^4$, or $R^4$ and $R^5$, may form another 6-membered aromatic or heteroaromatic ring sharing A and B, or B and D, or D and E, or E and F, respectively, and may be optionally substituted with from one to four substituents independently selected from the group of radicals set forth in the definition of $R^6$, $R^7$ and $R^8$ above;

each $R^9$, $R^{10}$ and $R^{11}$ is independently selected from H, straight chain or branched ($C_1$-$C_8$)alkyl, straight chain or branched ($C_2$-$C_8$)alkenyl, straight chain or branched ($C_2$-$C_8$)alkynyl, ($C_3$-$C_8$)cycloalkyl, ($C_4$-$C_8$)cycloalkenyl, 3-8 membered heterocycloalkyl, ($C_5$-$C_{11}$)bicycloalkyl, ($C_7$-$C_{11}$)bicycloalkenyl, 5-11 membered heterobicycloalkyl, (5-11 membered) heterobicycloalkenyl, ($C_6$-$C_{11}$)aryl or 5-12 membered heteroaryl; wherein each $R^9$, $R^{10}$ and $R^{11}$ is optionally substituted with from one to six substituents independently selected from F, Cl, Br, I, nitro, cyano, $CF_3$, —$NR^{12}R^{13}$, —$NR^{12}C(=O)R^{13}$, —$NR^{12}C(=O)NR^{13}R^{14}$, —$NR^{12}C(=O)OR^{13}$, —$NR^{12}S(=O)_2R^{13}$, —$NR^{12}S(=O)_2NR^{13}R^{14}$, —$OR^{12}$, —$OC(=O)R^{12}$, —$OC(=O)OR^{12}$, —$OC(=O)NR^{12}R^{13}$, —$OC(=O)SR^{12}$, —$C(=O)OR^{12}$, —$C(=O)R^{12}$, —$C(=O)NR^{12}R^{13}$, —$SR^{12}$, —$S(=O)R^{12}$, —$S(=O)_2R^{12}$, —$S(=O)_2NR^{12}R^{13}$ and $R^{12}$;

each $R^{12}$, $R^{13}$, and $R^{14}$ is independently selected from H, straight chain or branched ($C_1$-$C_8$)alkyl, straight chain or branched ($C_2$-$C_8$)alkenyl, straight chain or branched ($C_2$-$C_8$)alkynyl, ($C_3$-$C_8$)cycloalkyl, ($C_4$-$C_8$)cycloalkenyl, 3-8 membered heterocycloalkyl, ($C_5$-$C_{11}$)bicycloalkyl, ($C_7$-$C_{11}$)bicycloalkenyl, 5-11 membered heterobicycloalkyl, 5-11 membered heterobicycloalkenyl, ($C_6$-$C_{11}$)aryl and (5-12 membered) heteroaryl;

or an enantiomeric, diastereomeric, or tautomeric isomers thereof or a pharmaceutically acceptable salts thereof.

2. A compound according to claim 1 wherein one or two of A, B, D or E is N; or a pharmaceutically acceptable salt thereof.

3. A compound according to claim 1 wherein A and B are both N; or a pharmaceutically acceptable salt thereof.

4. A compound according to claim 1 wherein A and E are both N; or a pharmaceutically acceptable salt thereof.

5. A compound according to claim 1 wherein B and E are both N; or a pharmaceutically acceptable salt thereof.

6. A compound according to claim 1 wherein one of A, B or E is N; or a pharmaceutically acceptable salt thereof.

7. A compound according to claim 1 wherein one of A or B is N; or a pharmaceutically acceptable salt thereof.

8. A compound according to claim 1 wherein each $R^1$, $R^2$, $R^3$, $R^4$ and $R^5$ is independently selected from H, halo, ($C_1$-$C_6$)alkyl, ($C_1$-$C_6$)alkoxy, ($C_1$-$C_6$)fluoroalkyl, cyano, ($C_1$-$C_6$)alkoxycarbonyl; phenyl substituted or unsubstituted with halo, ($C_1$-$C_6$)alkyl, ($C_1$-$C_6$)alkoxy, ($C_1$-$C_6$)fluoroalkyl; and heteroaryl; or where any one of the $R^1$ and $R^2$, or $R^2$ and $R^3$, or $R^3$ and $R^4$, or $R^4$ and $R^5$ pairs located on adjacent carbon atoms join to form an unsaturated ($C_4$)alkylene bridge; or a pharmaceutically acceptable salt thereof.

9. A compound according to claim 1 selected from the group consisting of:

4-(5-Bromo-pyridin-3-yl)-1,4-diaza-bicyclo[3.2.1]octane;

4-(5-Phenyl-pyridin-3-yl)-1,4-diaza-bicyclo[3.2.1]octane;

4-Pyridin-2-yl-1,4-diaza-bicyclo[3.2.1]octane;

4-Pyridin-3-yl-1,4-diaza-bicyclo[3.2.1]octane;

4-Pyridin-4-yl-1,4-diaza-bicyclo[3.2.1]octane:

4-(5-Phenyl-pyridazin-3-yl)-1,4-diaza-bicyclo[3.2.1]octane;

4-(5-Bromo-pyridin-2-yl)-1,4-diaza-bicyclo[3.2.1]octane;

4-(6-Phenyl-pyridazin-3-yl)-1,4-diaza-bicyclo[3.2.1]octane;

4-Pyrazin-2-yl-1,4-diaza-bicyclo[3.2.1]octane;

4-Pyrimidin-5-yl-1,4-diaza-bicyclo[3.2.1]octane;

4-(5-Chloro-pyridin-3-yl)-1,4-diaza-bicyclo[3.2.1]octane;

4-[5-(3-Trifluoromethyl-phenyl)-pyridin-3-yl]-1,4-diaza-bicyclo[3.2.1]octane;

4-(3-Bromo-phenyl)-1,4-diaza-bicyclo[3.2.1]octane;

5-(1,4-Diaza-bicyclo[3.2.1]oct-4-yl)-nicotinonitrile;

4-(5-Trifluoromethyl-pyridin-3-yl)-1,4-diaza-bicyclo[3.2.1]octane;

4-[5-(2-Trifluoromethyl-phenyl)-pyridin-3-yl]-1,4-diaza-bicyclo[3.2.1]octane;

4-[5-(4-Trifluoromethyl-phenyl)-pyridin-3-yl]-1,4-diaza-bicyclo[3.2.1]octane;

4-[5-(2-Fluoro-phenyl)-pyridin-3-yl]-1,4-diaza-bicyclo[3.2.1]octane;

4-[5-(4-Fluoro-phenyl)-pyridin-3-yl]-1,4-diaza-bicyclo[3.2.1]octane;

3-(1,4-Diaza-bicyclo[3.2.1]oct-4-yl)-quinoline;

4-(3-Trifluoromethyl-pyridin-2-yl)-1,4-diaza-bicyclo[3.2.1]octane;

4-(6-Methoxy-pyridin-2-yl)-1,4-diaza-bicyclo[3.2.1]octane;

4-[5-(2-Methoxy-phenyl)-pyridin-3-yl]-1,4-diaza-bicyclo[3.2.1]octane;

4-[5-(3-Methoxy-phenyl)-pyridin-3-yl]-1,4-diaza-bicyclo[3.2.1]octane;

4-(5-o-Tolyl-pyridin-3-yl)-1,4-diaza-bicyclo[3.2.1]octane;

5-(1,4-Diaza-bicyclo[3.2.1]oct-4-yl)-nicotinic acid ethyl ester;

4-(5-Chloro-pyridin-2-yl)-1,4-diaza-bicyclo[3.2.1]octane;

4-(6-Methyl-pyridin-3-yl)-1,4-diaza-bicyclo[3.2.1]octane;

4-[5-(3-Trifluoromethyl-phenyl)-pyridin-2-yl]-1,4-diaza-bicyclo[3.2.1]octane;
4-[5-(4-Chloro-phenyl)-pyridin-2-yl]-1,4-diaza-bicyclo[3.2.1]octane;
4-(5-o-Tolyl-pyridin-2-yl)-1,4-diaza-bicyclo[3.2.1]octane;
4-[5-(3-Chloro-phenyl)-pyridin-2-yl]-1,4-diaza-bicyclo[3.2.1]octane;
4-[5-(3-Fluoro-phenyl)-pyridin-2-yl]-1,4-diaza-bicyclo[3.2.1]octane;
4-[5-(4-Chloro-phenyl)-pyridin-3-yl]-1,4-diaza-bicyclo[3.2.1]octane;
4-[5-(2,4-Dichloro-phenyl)-pyridin-3-yl]-1,4-diaza-bicyclo[3.2.1]octane;
4-[5-(3-Chloro-phenyl)-pyridin-3-yl]-1,4-diaza-bicyclo[3.2.1]octane;
4-(5-p-Tolyl-pyridin-3-yl)-1,4-diaza-bicyclo[3.2.1]octane;
4-[5-(4-Methoxy-phenyl)-pyridin-3-yl]-1,4-diaza-bicyclo[3.2.1]octane;
4-(5-Methoxy-pyridin-3-yl)-1,4-diaza-bicyclo[3.2.1]octane;
5-(1,4-Diaza-bicyclo[3.2.1]oct-4-yl)-[3,4']bipyridinyl; and
4-(2-Methyl-5-trifluoromethyl-pyridin-3-yl)-1,4-diaza-bicyclo[3.2.1]octane; or a pharmaceutically acceptable salt thereof.

10. A compound according to claim 1 selected from the group consisting of:
(+)-4-(5-Bromo-pyridin-3-yl)-1,4-diaza-bicyclo[3.2.1]octane;
(+)-4-(5-Phenyl-pyridin-3-yl)-1,4-diaza-bicyclo[3.2.1]octane;
(+)-4-Pyridin-2-yl-1,4-diaza-bicyclo[3.2.1]octane;
(+)-4-Pyridin-3-yl-1,4-diaza-bicyclo[3.2.1]octane;
(+)-4-Pyridin-4-yl-1,4-diaza-bicyclo[3.2.1]octane;
(+)-4-(5-Phenyl-pyridazin-3-yl)-1,4-diaza-bicyclo[3.2.1]octane;
(+)-4-(5-Bromo-pyridin-2-yl)-1,4-diaza-bicyclo[3.2.1]octane;
(+)-4-(6-Phenyl-pyridazin-3-yl)-1,4-diaza-bicyclo[3.2.1]octane;
(+)-4-Pyrazin-2-yl-1,4-diaza-bicyclo[3.2.1]octane;
(+)-4-Pyrimidin-5-yl-1,4-diaza-bicyclo[3.2.1]octane;
(+)-4-(5-Chloro-pyridin-3-yl)-1,4-diaza-bicyclo[3.2.1]octane;
(+)-4-[5-(3-Trifluoromethyl-phenyl)-pyridin-3-yl]-1,4-diaza-bicyclo[3.2.1]octane;
(+)-4-(3-Bromo-phenyl)-1,4-diaza-bicyclo[3.2.1]octane;
(+)-5-(1,4-Diaza-bicyclo[3.2.1]oct-4-yl)-nicotinonitrile;
(+)-4-(5-Trifluoromethyl-pyridin-3-yl)-1,4-diaza-bicyclo[3.2.1]octane;
(+)-4-[5-(2-Trifluoromethyl-phenyl)-pyridin-3-yl]-1,4-diaza-bicyclo[3.2.1]octane;
(+)-4-[5-(4-Trifluoromethyl-phenyl)-pyridin-3-yl]-1,4-diaza-bicyclo[3.2.1]octane;
(+)-4-[5-(2-Fluoro-phenyl)-pyridin-3-yl]-1,4-diaza-bicyclo[3.2.1]octane;
(+)-4-[5-(4-Fluoro-phenyl)-pyridin-3-yl]-1,4-diaza-bicyclo[3.2.1]octane;
(+)-3-(1,4-Diaza-bicyclo[3.2.1]oct-4-yl)-quinoline;
(+)-4-(3-Trifluoromethyl-pyridin-2-yl)-1,4-diaza-bicyclo[3.2.1]octane;
(+)-4-(6-Methoxy-pyridin-2-yl)-1,4-diaza-bicyclo[3.2.1]octane;
(+)-4-[5-(2-Methoxy-phenyl)-pyridin-3-yl]-1,4-diaza-bicyclo[3.2.1]octane;
(+)-4-[5-(3-Methoxy-phenyl)-pyridin-3-yl]-1,4-diaza-bicyclo[3.2.1]octane;
(+)-4-(5-o-Tolyl-pyridin-3-yl)-1,4-diaza-bicyclo[3.2.1]octane;
(+)-5-(1,4-Diaza-bicyclo[3.2.1]oct-4-yl)-nicotinic acid ethyl ester;
(+)-4-(5-Chloro-pyridin-2-yl)-1,4-diaza-bicyclo[3.2.1]octane;
(+)-4-(6-Methyl-pyridin-3-yl)-1,4-diaza-bicyclo[3.2.1]octane;
(+)-4-[5-(3-Trifluoromethyl-phenyl)-pyridin-2-yl]-1,4-diaza-bicyclo[3.2.1]octane;
(+)-4-[5-(4-Chloro-phenyl)-pyridin-2-yl]-1,4-diaza-bicyclo[3.2.1]octane;
(+)-4-(5-o-Tolyl-pyridin-2-yl)-1,4-diaza-bicyclo[3.2.1]octane;
(+)-4-[5-(3-Chloro-phenyl)-pyridin-2-yl]-1,4-diaza-bicyclo[3.2.1]octane;
(+)-4-[5-(3-Fluoro-phenyl)-pyridin-2-yl]-1,4-diaza-bicyclo[3.2.1]octane;
(+)-4-[5-(4-Chloro-phenyl)-pyridin-3-yl]-1,4-diaza-bicyclo[3.2.1]octane;
(+)-4-[5-(2,4-Dichloro-phenyl)-pyridin-3-yl]-1,4-diaza-bicyclo[3.2.1]octane;
(+)-4-[5-(3-Chloro-phenyl)-pyridin-3-yl]-1,4-diaza-bicyclo[3.2.1]octane;
(+)-4-(5-p-Tolyl-pyridin-3-yl)-1,4-diaza-bicyclo[3.2.1]octane;
(+)-4-[5-(4-Methoxy-phenyl)-pyridin-3-yl]-1,4-diaza-bicyclo[3.2.1]octane;
(+)-4-(5-Methoxy-pyridin-3-yl)-1,4-diaza-bicyclo[3.2.1]octane;
(+)-5-(1,4-Diaza-bicyclo[3.2.1]oct-4-yl)-[3,4']bipyridinyl; and
(+)-4-(2-Methyl-5-trifluoromethyl-pyridin-3-yl)-1,4-diaza-bicyclo[3.2.1]octane; or a pharmaceutically acceptable salt thereof.

11. A compound according to claim 1 selected from the group consisting of:
(−)-4-(5-Bromo-pyridin-3-yl)-1,4-diaza-bicyclo[3.2.1]octane;
(−)-4-(5-Phenyl-pyridin-3-yl)-1,4-diaza-bicyclo[3.2.1]octane;
(−)-4-Pyridin-2-yl-1,4-diaza-bicyclo[3.2.1]octane;
(−)-4-Pyridin-3-yl-1,4-diaza-bicyclo[3.2.1]octane;
(−)-4-Pyridin-4-yl-1,4-diaza-bicyclo[3.2.1]octane;
(−)-4-(5-Phenyl-pyridazin-3-yl)-1,4-diaza-bicyclo[3.2.1]octane;
(−)-4-(5-Bromo-pyridin-2-yl)-1,4-diaza-bicyclo[3.2.1]octane;
(−)-4-(6-Phenyl-pyridazin-3-yl)-1,4-diaza-bicyclo[3.2.1]octane;
(−)-4-Pyrazin-2-yl-1,4-diaza-bicyclo[3.2.1]octane;
(−)-4-Pyrimidin-5-yl-1,4-diaza-bicyclo[3.2.1]octane;
(−)-4-(5-Chloro-pyridin-3-yl)-1,4-diaza-bicyclo[3.2.1]octane;
(−)-4-[5-(3-Trifluoromethyl-phenyl)-pyridin-3-yl]-1,4-diaza-bicyclo[3.2.1]octane;
(−)-4-(3-Bromo-phenyl)-1,4-diaza-bicyclo[3.2.1]octane;
(−)-5-(1,4-Diaza-bicyclo[3.2.1]oct-4-yl)-nicotinonitrile;
(−)-4-(5-Trifluoromethyl-pyridin-3-yl)-1,4-diaza-bicyclo[3.2.1]octane;
(−)-4-[5-(2-Trifluoromethyl-phenyl)-pyridin-3-yl]-1,4-diaza-bicyclo[3.2.1]octane;
(−)-4-[5-(4-Trifluoromethyl-phenyl)-pyridin-3-yl]-1,4-diaza-bicyclo[3.2.1]octane;

(−)-4-[5-(2-Fluoro-phenyl)-pyridin-3-yl]-1,4-diaza-bicyclo[3.2.1]octane;
(−)-4-[5-(4-Fluoro-phenyl)-pyridin-3-yl]-1,4-diaza-bicyclo[3.2.1]octane;
(−)-3-(1,4-Diaza-bicyclo[3.2.1]oct-4-yl)-quinoline;
(−)-4-(3-Trifluoromethyl-pyridin-2-yl)-1,4-diaza-bicyclo[3.2.1]octane;
(−)-4-(6-Methoxy-pyridin-2-yl)-1,4-diaza-bicyclo[3.2.1]octane;
(−)-4-[5-(2-Methoxy-phenyl)-pyridin-3-yl]-1,4-diaza-bicyclo[3.2.1]octane;
(−)-4-[5-(3-Methoxy-phenyl)-pyridin-3-yl]-1,4-diaza-bicyclo[3.2.1]octane;
(−)-4-(5-o-Tolyl-pyridin-3-yl)-1,4-diaza-bicyclo[3.2.1]octane;
(−)-5-(1,4-Diaza-bicyclo[3.2.1]oct-4-yl)-nicotinic acid ethyl ester;
(−)-4-(5-Chloro-pyridin-2-yl)-1,4-diaza-bicyclo[3.2.1]octane;
(−)-4-(6-Methyl-pyridin-3-yl)-1,4-diaza-bicyclo[3.2.1]octane;
(−)-4-[5-(3-Trifluoromethyl-phenyl)-pyridin-2-yl]-1,4-diaza-bicyclo[3.2.1]octane;
(−)-4-[5-(4-Chloro-phenyl)-pyridin-2-yl]-1,4-diaza-bicyclo[3.2.1]octane;
(−)-4-(5-o-Tolyl-pyridin-2-yl)-1,4-diaza-bicyclo[3.2.1]octane;
(−)-4-[5-(3-Chloro-phenyl)-pyridin-2-yl]-1,4-diaza-bicyclo[3.2.1]octane;
(−)-4-[5-(3-Fluoro-phenyl)-pyridin-2-yl]-1,4-diaza-bicyclo[3.2.1]octane;
(−)-4-[5-(4-Chloro-phenyl)-pyridin-3-yl]-1,4-diaza-bicyclo[3.2.1]octane;
(−)-4-[5-(2,4-Dichloro-phenyl)-pyridin-3-yl]-1,4-diaza-bicyclo[3.2.1]octane;
(−)-4-[5-(3-Chloro-phenyl)-pyridin-3-yl]-1,4-diaza-bicyclo[3.2.1]octane;
(−)-4-(5-p-Tolyl-pyridin-3-yl)-1,4-diaza-bicyclo[3.2.1]octane;
(−)-4-[5-(4-Methoxy-phenyl)-pyridin-3-yl]-1,4-diaza-bicyclo[3.2.1]octane;
(−)-4-(5-Methoxy-pyridin-3-yl)-1,4-diaza-bicyclo[3.2.1]octane;
(−)-5-(1,4-Diaza-bicyclo[3.2.1]oct-4-yl)-[3,4']bipyridinyl; and
(−)-4-(2-Methyl-5-trifluoromethyl-pyridin-3-yl)-1,4-diaza-bicyclo[3.2.1]octane; or a pharmaceutically acceptable salt thereof.

12. A pharmaceutical composition comprising a therapeutically effective amount of a compound of claim 1 or a pharmaceutically acceptable salt thereof and pharmaceutically acceptable carrier.

* * * * *

UNITED STATES PATENT AND TRADEMARK OFFICE
CERTIFICATE OF CORRECTION

PATENT NO.        : 7,442,694 B2
APPLICATION NO.   : 10/657738
DATED             : October 28, 2008
INVENTOR(S)       : Coe et al.

Page 1 of 1

It is certified that error appears in the above-identified patent and that said Letters Patent is hereby corrected as shown below:

On the cover page,

[*] Notice:   Subject to any disclaimer, the term of this patent is extended or adjusted under 35 USC 154(b) by (280) days Delete the phrase "by 280 days" and insert -- by 243 days --

Signed and Sealed this

Nineteenth Day of May, 2009

JOHN DOLL
*Acting Director of the United States Patent and Trademark Office*